(12) United States Patent
Rowe et al.

(10) Patent No.: US 12,690,815 B2
(45) Date of Patent: Jul. 28, 2026

---

(54) CARDIAC IMPLANT DEVICES WITH INTEGRATED PRESSURE SENSING

(71) Applicant: Edwards Lifesciences Corporation, Irvine, CA (US)

(72) Inventors: Stanton J. Rowe, Newport Coast, CA (US); Arvin T. Chang, Yorba Linda, CA (US); Joseph Arthur Passman, Costa Mesa, CA (US); Scott Louis Pool, Laguna Hills, CA (US); Jinny Lee, Corona del Mar, CA (US); Viral Lalitmohan Gandhi, Costa Mesa, CA (US); Alison S. Curtis, Costa Mesa, CA (US); Gregory Bak-Boychuk, San Clemente, CA (US); Emil Karapetian, Huntington Beach, CA (US); Glen T. Rabito, Lake Forest, CA (US); Cristobal R. Hernandez, Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1250 days.

(21) Appl. No.: 17/413,125

(22) PCT Filed: Dec. 9, 2019

(86) PCT No.: PCT/US2019/065148
§ 371 (c)(1),
(2) Date: Jun. 11, 2021

(87) PCT Pub. No.: WO2020/123338
PCT Pub. Date: Jun. 18, 2020

(65) Prior Publication Data
US 2022/0008014 A1 Jan. 13, 2022

Related U.S. Application Data

(60) Provisional application No. 62/778,561, filed on Dec. 12, 2018.

(51) Int. Cl.
*A61B 5/00* (2006.01)
*A61B 5/0215* (2006.01)
*A61M 25/09* (2006.01)

(52) U.S. Cl.
CPC .......... *A61B 5/6862* (2013.01); *A61B 5/0031* (2013.01); *A61B 5/02158* (2013.01);
(Continued)

(58) Field of Classification Search
CPC . A61B 5/6862; A61B 5/0031; A61B 5/02158; A61B 5/6869; A61B 5/6882;
(Continued)

(56) References Cited

U.S. PATENT DOCUMENTS

| | | | |
|---|---|---|---|
| 3,538,917 A | 11/1970 | Selker | |
| 3,675,656 A | 7/1972 | Hakim | |

(Continued)

FOREIGN PATENT DOCUMENTS

| | | |
|---|---|---|
| CN | 105193529 A | 12/2015 |
| CN | 111317516 A | 6/2020 |

(Continued)

OTHER PUBLICATIONS

Dehennis A.D et al: "A fully integrated multisite pressure sensor for wireless arterial flow characterization", Journal moficroelectromechanical systems, Jun. 1, 2006 (Jun. 1, 2006), pp. 678-685, XP093004369, New York, NY DOI: 0.1109/JMEMS.2006.876668 Retrieved from the Internet : URL :https //ieeexplore.ieee.org/stampPDF/getPDF. jsp?tp=&arnumber=1638495&ref= aHR0cHM6Ly9zY2hvbGFyLmdvb2dsZS5jb20v[retrieved on Dec. 2, 2022]* figure 1 *.

(Continued)

*Primary Examiner* — Jennifer Robertson
*Assistant Examiner* — Elina Sohyun Jang
(74) *Attorney, Agent, or Firm* — Klarquist Sparkman LLP

(57) ABSTRACT

A sensor implant device includes a shunt structure comprising a flow path conduit and a plurality of arms configured to
(Continued)

secure the shunt structure to a tissue wall, and a pressure sensor device attached to one of the plurality of arms of the shunt structure. The pressure sensor device comprises one or more sensor elements, an antenna, control circuitry electrically coupled to the one or more sensor elements and the antenna, and a housing that houses the control circuitry.

23 Claims, 35 Drawing Sheets

(52) U.S. Cl.
CPC .......... *A61B 5/6869* (2013.01); *A61B 5/6882* (2013.01); *A61M 25/09* (2013.01); *A61B 2560/0219* (2013.01); *A61B 2562/0247* (2013.01); *A61M 2205/3344* (2013.01); *A61M 2210/125* (2013.01)

(58) Field of Classification Search
CPC .... A61B 2560/0219; A61B 2562/0247; A61B 2017/00252; A61B 5/6876; A61B 2090/064; A61B 5/0215; A61M 25/09; A61M 2205/3344; A61M 2210/125; A61F 2/2442; A61F 2002/249
See application file for complete search history.

(56) References Cited

U.S. PATENT DOCUMENTS

| | | | |
|---|---|---|---|
| 3,730,186 A | 5/1973 | Edmunds, Jr. et al. | |
| 3,853,126 A | 12/1974 | Schulte | |
| 3,882,862 A | 5/1975 | Berend | |
| 3,882,882 A | 5/1975 | Preisig | |
| 3,903,894 A | 9/1975 | Rosen et al. | |
| 4,256,094 A | 3/1981 | Kapp et al. | |
| 4,428,365 A | 1/1984 | Hakky | |
| 4,556,050 A | 12/1985 | Hodgson et al. | |
| 4,578,061 A | 3/1986 | Lemelson | |
| 4,586,501 A | 5/1986 | Claracq | |
| 4,601,718 A | 7/1986 | Possis et al. | |
| 4,655,777 A | 4/1987 | Dunn et al. | |
| 4,708,140 A | 11/1987 | Baron | |
| 4,712,551 A | 12/1987 | Rayhanabad | |
| 4,739,762 A | 4/1988 | Palmaz | |
| 4,762,128 A | 8/1988 | Rosenbluth | |
| 4,774,949 A | 10/1988 | Fogarty | |
| 4,828,544 A | 5/1989 | Lane et al. | |
| 4,861,336 A | 8/1989 | Helzel | |
| 4,881,939 A | 11/1989 | Newman | |
| 4,946,457 A | 8/1990 | Elliott | |
| 4,950,227 A | 8/1990 | Savin et al. | |
| 4,961,729 A | 10/1990 | Vaillancourt | |
| 4,997,431 A | 3/1991 | Isner et al. | |
| 5,026,377 A | 6/1991 | Burton et al. | |
| 5,054,492 A | 10/1991 | Scribner et al. | |
| 5,108,420 A | 4/1992 | Marks | |
| 5,109,420 A | 4/1992 | Nonaka | |
| 5,114,408 A | 5/1992 | Fleischhaker et al. | |
| 5,167,239 A | 12/1992 | Cohen et al. | |
| 5,190,528 A | 3/1993 | Fonger et al. | |
| 5,193,546 A | 3/1993 | Shaknovich | |
| 5,201,757 A | 4/1993 | Heyn et al. | |
| 5,242,397 A | 9/1993 | Barath et al. | |
| 5,242,410 A | 9/1993 | Melker | |
| 5,258,042 A | 11/1993 | Mehta | |
| 5,267,940 A | 12/1993 | Moulder | |
| 5,287,861 A | 2/1994 | Wilk | |
| 5,320,613 A | 6/1994 | Houge et al. | |
| 5,330,496 A | 7/1994 | Alferness | |
| 5,334,217 A | 8/1994 | Das | |
| 5,345,940 A | 9/1994 | Seward et al. | |
| 5,354,279 A | 10/1994 | Hofling | |
| 5,366,490 A | 11/1994 | Edwards et al. | |
| 5,373,849 A | 12/1994 | Maroney et al. | |
| 5,419,777 A | 5/1995 | Hofling | |
| 5,423,878 A | 6/1995 | Franz | |
| 5,429,634 A | 7/1995 | Narciso, Jr. | |
| 5,431,700 A | 7/1995 | Sloan | |
| 5,443,497 A | 8/1995 | Venbrux | |
| 5,445,600 A | 8/1995 | Abdulla | |
| 5,445,646 A | 8/1995 | Euteneuer et al. | |
| 5,456,284 A | 10/1995 | Ryan et al. | |
| 5,456,712 A | 10/1995 | Maginot | |
| 5,462,523 A | 10/1995 | Samson et al. | |
| 5,464,395 A | 11/1995 | Faxon et al. | |
| 5,491,224 A | 2/1996 | Bittner et al. | |
| 5,492,304 A | 2/1996 | Smith et al. | |
| 5,496,311 A | 3/1996 | Abele et al. | |
| 5,499,630 A | 3/1996 | Hiki et al. | |
| 5,507,724 A | 4/1996 | Hofmann et al. | |
| 5,507,725 A | 4/1996 | Savage et al. | |
| 5,538,504 A | 7/1996 | Linden et al. | |
| 5,551,954 A | 9/1996 | Buscemi et al. | |
| 5,554,182 A | 9/1996 | Dinh et al. | |
| 5,570,693 A | 11/1996 | Jang et al. | |
| 5,571,086 A | 11/1996 | Kaplan et al. | |
| 5,571,151 A | 11/1996 | Gregory | |
| 5,588,960 A | 12/1996 | Edwards et al. | |
| 5,597,146 A | 1/1997 | Putman | |
| 5,597,378 A | 1/1997 | Jervis | |
| 5,599,300 A | 2/1997 | Weaver et al. | |
| 5,614,204 A | 3/1997 | Cochrum | |
| 5,628,784 A | 5/1997 | Strecker | |
| 5,661,133 A | 8/1997 | Leiden et al. | |
| 5,662,609 A | 9/1997 | Slepian | |
| 5,662,711 A | 9/1997 | Douglas | |
| 5,665,077 A | 9/1997 | Rosen et al. | |
| 5,669,880 A | 9/1997 | Solar | |
| 5,682,906 A | 11/1997 | Sterman et al. | |
| 5,690,670 A | 11/1997 | Davidson | |
| 5,693,029 A | 12/1997 | Leonhardt | |
| 5,704,361 A | 1/1998 | Seward et al. | |
| 5,704,926 A | 1/1998 | Sutton | |
| 5,713,363 A | 2/1998 | Seward et al. | |
| 5,713,853 A | 2/1998 | Clark et al. | |
| 5,718,725 A | 2/1998 | Sterman et al. | |
| 5,724,975 A | 3/1998 | Negus et al. | |
| 5,724,977 A | 3/1998 | Yock et al. | |
| 5,728,123 A | 3/1998 | Lemelson et al. | |
| 5,735,847 A | 4/1998 | Gough et al. | |
| 5,738,658 A | 4/1998 | Maus et al. | |
| 5,743,874 A | 4/1998 | Fischell et al. | |
| 5,755,682 A | 5/1998 | Knudson et al. | |
| 5,756,696 A | 5/1998 | Gray et al. | |
| 5,771,895 A | 6/1998 | Slager | |
| 5,772,629 A | 6/1998 | Kaplan | |
| 5,772,632 A | 6/1998 | Forman | |
| 5,807,258 A | 9/1998 | Cimochowski et al. | |
| 5,807,306 A | 9/1998 | Shapland et al. | |
| 5,810,780 A | 9/1998 | Brimhall et al. | |
| 5,814,005 A | 9/1998 | Barra et al. | |
| 5,827,216 A | 10/1998 | Igo et al. | |
| 5,830,222 A | 11/1998 | Makower | |
| 5,830,224 A | 11/1998 | Cohn et al. | |
| 5,836,913 A | 11/1998 | Orth et al. | |
| 5,843,090 A | 12/1998 | Schuetz | |
| 5,843,170 A | 12/1998 | Ahn | |
| 5,944,738 A | 8/1999 | Amplatz et al. | |
| 5,951,569 A | 9/1999 | Tuckey et al. | |
| 5,954,691 A | 9/1999 | Prosl | |
| 5,967,986 A * | 10/1999 | Cimochowski | A61B 5/0031 600/504 |
| 5,989,280 A | 11/1999 | Euteneuer et al. | |
| 6,019,788 A | 2/2000 | Butters et al. | |
| 6,042,589 A | 3/2000 | Marianne | |
| 6,053,891 A | 4/2000 | DeCampli | |
| 6,081,738 A | 6/2000 | Hinohara et al. | |
| 6,086,553 A | 7/2000 | Akbik | |
| 6,092,526 A | 7/2000 | LaFontaine et al. | |
| 6,095,878 A | 8/2000 | Van Balen | |
| 6,113,612 A | 9/2000 | Swanson et al. | |
| 6,120,494 A | 9/2000 | Jonkman | |

(56)                References Cited

U.S. PATENT DOCUMENTS

| | | | |
|---|---|---|---|
| 6,120,522 | A | 9/2000 | Vrba et al. |
| 6,120,534 | A | 9/2000 | Ruiz |
| 6,152,937 | A | 11/2000 | Peterson et al. |
| 6,165,185 | A | 12/2000 | Shennib et al. |
| 6,168,620 | B1 | 1/2001 | Kerr |
| 6,168,820 | B1 | 1/2001 | Garwood et al. |
| 6,174,681 | B1 | 1/2001 | Halling et al. |
| 6,190,353 | B1 | 2/2001 | Makower et al. |
| 6,193,734 | B1 | 2/2001 | Bolduc et al. |
| 6,196,230 | B1 | 3/2001 | Hall et al. |
| 6,241,743 | B1 | 6/2001 | Levin et al. |
| 6,248,117 | B1 | 6/2001 | Blatter |
| 6,251,116 | B1 | 6/2001 | Shennib et al. |
| 6,254,631 | B1 | 7/2001 | Thompson |
| 6,280,412 | B1 | 8/2001 | Pederson, Jr. et al. |
| 6,283,951 | B1 | 9/2001 | Flaherty et al. |
| 6,287,280 | B1 | 9/2001 | Lampropoulos et al. |
| 6,287,332 | B1 | 9/2001 | Bolz et al. |
| 6,290,728 | B1 | 9/2001 | Phelps et al. |
| 6,302,875 | B1 | 10/2001 | Makower et al. |
| 6,302,892 | B1 | 10/2001 | Wilk |
| 6,302,905 | B1 | 10/2001 | Goldsteen et al. |
| 6,309,350 | B1 | 10/2001 | VanTassel et al. |
| 6,309,415 | B1 | 10/2001 | Pulnev et al. |
| 6,315,752 | B1 | 11/2001 | DiMatteo |
| 6,325,798 | B1 | 12/2001 | Edwards et al. |
| 6,361,545 | B1 | 3/2002 | Macoviak et al. |
| 6,375,615 | B1 | 4/2002 | Flaherty et al. |
| 6,387,116 | B1 | 5/2002 | McKenzie et al. |
| 6,387,119 | B2 | 5/2002 | Wolf et al. |
| 6,391,036 | B1 | 5/2002 | Berg et al. |
| 6,402,767 | B1 | 6/2002 | Nash et al. |
| 6,443,158 | B1 | 9/2002 | LaFontaine et al. |
| 6,451,048 | B1 | 9/2002 | Berg et al. |
| 6,458,140 | B2 | 10/2002 | Akin et al. |
| 6,464,665 | B1 | 10/2002 | Heuser |
| 6,468,303 | B1 | 10/2002 | Amplatz et al. |
| 6,475,226 | B1 | 11/2002 | Belef et al. |
| 6,494,889 | B1 | 12/2002 | Fleischman et al. |
| 6,503,247 | B2 | 1/2003 | Swartz et al. |
| 6,506,201 | B2 | 1/2003 | Di Caprio et al. |
| 6,508,824 | B1 | 1/2003 | Flaherty et al. |
| 6,561,998 | B1 | 5/2003 | Roth et al. |
| 6,562,066 | B1 | 5/2003 | Martin |
| 6,565,542 | B2 | 5/2003 | Kumar et al. |
| 6,575,168 | B2 | 6/2003 | LaFontaine et al. |
| 6,579,311 | B1 | 6/2003 | Makower |
| 6,589,251 | B2 | 7/2003 | Yee et al. |
| 6,595,941 | B1 | 7/2003 | Blatter |
| 6,602,241 | B2 | 8/2003 | Makower et al. |
| 6,613,074 | B1 | 9/2003 | Mitelberg et al. |
| 6,616,624 | B1 | 9/2003 | Kieval |
| 6,616,675 | B1 | 9/2003 | Evard et al. |
| 6,620,202 | B2 | 9/2003 | Bottcher et al. |
| 6,623,494 | B1 | 9/2003 | Blatter |
| 6,626,920 | B2 | 9/2003 | Whayne |
| 6,638,293 | B1 | 10/2003 | Makower et al. |
| 6,692,482 | B2 | 2/2004 | Heller et al. |
| 6,695,878 | B2 | 2/2004 | McGuckin, Jr. et al. |
| 6,699,256 | B1 | 3/2004 | Logan et al. |
| 6,702,828 | B2 | 3/2004 | Whayne |
| 6,709,414 | B2 | 3/2004 | Weitzel et al. |
| 6,709,444 | B1 | 3/2004 | Makower |
| 6,712,836 | B1 | 3/2004 | Berg et al. |
| 6,719,804 | B2 | 4/2004 | St. Pierre |
| 6,726,659 | B1 | 4/2004 | Stocking et al. |
| 6,726,677 | B1 | 4/2004 | Flaherty et al. |
| 6,736,825 | B2 | 5/2004 | Blatter et al. |
| 6,740,426 | B2 | 5/2004 | Kawachi et al. |
| 6,743,244 | B2 | 6/2004 | Blatter et al. |
| 6,743,259 | B2 | 6/2004 | Ginn |
| 6,746,426 | B1 | 6/2004 | Flaherty et al. |
| 6,748,484 | B1 | 6/2004 | Henderson et al. |
| 6,758,854 | B1 | 7/2004 | Butler et al. |
| 6,776,785 | B1 | 8/2004 | Yencho et al. |
| 6,797,083 | B2 | 9/2004 | Peterson |
| 6,802,858 | B2 | 10/2004 | Gambale et al. |
| 6,805,706 | B2 | 10/2004 | Solovay et al. |
| 6,808,498 | B2 | 10/2004 | Laroya et al. |
| 6,827,698 | B1 | 12/2004 | Kleinekofort |
| 6,847,348 | B2 | 1/2005 | Rojewski |
| 6,854,172 | B2 | 2/2005 | Kaese et al. |
| 6,858,035 | B2 | 2/2005 | Whayne |
| 6,869,437 | B1 | 3/2005 | Hausen et al. |
| 6,893,413 | B2 | 5/2005 | Martin |
| 6,913,600 | B2 | 7/2005 | Valley et al. |
| 6,913,607 | B2 | 7/2005 | Ainsworth et al. |
| 6,915,154 | B1 | 7/2005 | Docherty et al. |
| 6,926,690 | B2 | 8/2005 | Renati |
| 6,972,023 | B2 | 12/2005 | Whayne et al. |
| 6,979,351 | B2 | 12/2005 | Forsell et al. |
| 6,985,774 | B2 | 1/2006 | Kieval et al. |
| 7,002,491 | B2 | 2/2006 | Robbins |
| 7,008,397 | B2 | 3/2006 | Tweden et al. |
| 7,011,094 | B2 | 3/2006 | Rapacki et al. |
| 7,011,678 | B2 | 3/2006 | Tenerz et al. |
| 7,025,741 | B2 | 4/2006 | Cull |
| 7,025,746 | B2 | 4/2006 | Tal |
| 7,037,329 | B2 | 5/2006 | Martin |
| 7,056,294 | B2 | 6/2006 | Khairkhahan et al. |
| 7,056,320 | B2 | 6/2006 | Utley et al. |
| 7,056,325 | B1 | 6/2006 | Makower et al. |
| 7,077,860 | B2 | 7/2006 | Yan et al. |
| 7,083,631 | B2 | 8/2006 | Houser et al. |
| 7,108,701 | B2 | 9/2006 | Evens et al. |
| 7,115,136 | B2 | 10/2006 | Park et al. |
| 7,118,546 | B2 | 10/2006 | Blatter |
| 7,128,750 | B1 | 10/2006 | Stergiopulos |
| 7,175,644 | B2 | 2/2007 | Cooper et al. |
| 7,182,771 | B1 | 2/2007 | Houser et al. |
| 7,235,095 | B2 | 6/2007 | Haverkost et al. |
| 7,294,115 | B1 | 11/2007 | Wilk |
| 7,316,706 | B2 | 1/2008 | Bloom et al. |
| 7,317,951 | B2 | 1/2008 | Schneider et al. |
| 7,318,804 | B2 | 1/2008 | Weitzel et al. |
| 7,326,221 | B2 | 2/2008 | Sakamoto et al. |
| 7,331,985 | B2 | 2/2008 | Thompson et al. |
| 7,335,220 | B2 | 2/2008 | Khosravi et al. |
| 7,351,247 | B2 | 4/2008 | Kupiecki et al. |
| 7,361,181 | B2 | 4/2008 | Hindrichs et al. |
| 7,374,567 | B2 | 5/2008 | Heuser |
| D581,054 | S | 11/2008 | Moore |
| 7,452,334 | B2 | 11/2008 | Gianchandani et al. |
| 7,462,162 | B2 | 12/2008 | Phan et al. |
| 7,476,200 | B2 | 1/2009 | Tal |
| 7,530,963 | B2 | 5/2009 | Albright |
| 7,563,277 | B2 | 7/2009 | Case et al. |
| 7,623,926 | B2 | 11/2009 | Rossing et al. |
| 7,625,593 | B2 | 12/2009 | Mandrusov et al. |
| 7,628,768 | B2 | 12/2009 | Faul et al. |
| D612,499 | S | 3/2010 | Ondracek et al. |
| 7,691,110 | B2 | 4/2010 | Secrest et al. |
| 7,699,863 | B2 | 4/2010 | Marco et al. |
| 7,722,549 | B2 | 5/2010 | Nakao |
| 7,722,665 | B2 | 5/2010 | Anwar et al. |
| 7,744,621 | B2 | 6/2010 | Paul et al. |
| 7,794,495 | B2 | 9/2010 | Gale et al. |
| 7,807,191 | B2 | 10/2010 | Iyer et al. |
| 7,815,590 | B2 | 10/2010 | Cooper |
| 7,815,656 | B2 | 10/2010 | Rust et al. |
| 7,815,852 | B2 | 10/2010 | Sternby |
| 7,828,814 | B2 | 11/2010 | Brenneman et al. |
| 7,846,179 | B2 | 12/2010 | Belef et al. |
| 7,846,194 | B2 | 12/2010 | Hartley et al. |
| 7,850,705 | B2 | 12/2010 | Bachinski et al. |
| 7,867,547 | B2 | 1/2011 | Tochterman et al. |
| 7,879,367 | B2 | 2/2011 | Heublein et al. |
| 7,892,246 | B2 | 2/2011 | Akin et al. |
| 7,892,247 | B2 | 2/2011 | Conston et al. |
| 7,923,022 | B2 | 4/2011 | Wang et al. |
| 7,951,194 | B2 | 5/2011 | Gueriguian et al. |
| 7,959,603 | B2 | 6/2011 | Wahr et al. |
| 7,964,210 | B2 | 6/2011 | Wang et al. |
| 7,967,769 | B2 | 6/2011 | Faul et al. |

(56) References Cited

U.S. PATENT DOCUMENTS

| | | | |
|---|---|---|---|
| 7,972,346 B2 | 7/2011 | Bachmann et al. |
| 8,002,821 B2 | 8/2011 | Stinson |
| 8,016,782 B2 | 9/2011 | Brenneman et al. |
| 8,029,470 B2 | 10/2011 | Whiting et al. |
| 8,048,150 B2 | 11/2011 | Weber et al. |
| 8,052,751 B2 | 11/2011 | Aklog et al. |
| 8,057,534 B2 | 11/2011 | Boismier et al. |
| 8,070,708 B2 | 12/2011 | Rottenberg et al. |
| 8,088,171 B2 | 1/2012 | Brenneman |
| 8,089,029 B2 | 1/2012 | Flanagan |
| 8,091,556 B2 | 1/2012 | Keren et al. |
| 8,128,689 B2 | 3/2012 | Weber et al. |
| 8,152,773 B2 | 4/2012 | Albrecht et al. |
| 8,182,527 B2 | 5/2012 | Llanos et al. |
| 8,214,015 B2 | 7/2012 | Macaulay et al. |
| 8,221,495 B2 | 7/2012 | Shrivastava et al. |
| 8,226,592 B2 | 7/2012 | Brenneman et al. |
| D665,500 S | 8/2012 | Martin et al. |
| 8,282,591 B2 | 10/2012 | Khan et al. |
| 8,308,682 B2 | 11/2012 | Kramer et al. |
| 8,357,193 B2 | 1/2013 | Phan et al. |
| 8,376,979 B2 | 2/2013 | Kapadia |
| 8,382,697 B2 | 2/2013 | Brenneman et al. |
| D679,015 S | 3/2013 | Nakaji |
| 8,409,167 B2 | 4/2013 | Roschak |
| 8,500,697 B2 | 8/2013 | Kurth et al. |
| 8,506,984 B2 | 8/2013 | Cook et al. |
| 8,518,062 B2 | 8/2013 | Cole et al. |
| 8,518,662 B2 | 8/2013 | Ritzen et al. |
| 8,545,552 B2 | 10/2013 | Garrison et al. |
| 8,641,724 B2 | 2/2014 | Brenneman et al. |
| 8,657,790 B2 | 2/2014 | Tal et al. |
| 8,696,611 B2 | 4/2014 | Nitzan et al. |
| D705,427 S | 5/2014 | Jagger et al. |
| 8,768,487 B2 | 7/2014 | Farnan et al. |
| 8,784,860 B2 | 7/2014 | Falotico et al. |
| 8,882,830 B2 | 11/2014 | Cartledge et al. |
| 8,920,449 B2 | 12/2014 | Wilkinson |
| 8,926,545 B2 | 1/2015 | Brenneman et al. |
| 8,932,341 B2 | 1/2015 | Brenneman |
| D723,166 S | 2/2015 | Igaki et al. |
| 8,951,276 B2 | 2/2015 | Kellerman et al. |
| 9,005,155 B2 | 4/2015 | Sugimoto |
| 9,044,588 B2 | 6/2015 | Conn |
| 9,061,115 B2 | 6/2015 | Ward et al. |
| 9,067,050 B2 | 6/2015 | Gallagher et al. |
| 9,198,756 B2 | 12/2015 | Aklog et al. |
| 9,232,997 B2 | 1/2016 | Sugimoto et al. |
| 9,277,995 B2 | 3/2016 | Celermajer et al. |
| 9,345,485 B2 | 5/2016 | Dakin et al. |
| 9,439,746 B2 | 9/2016 | Bell et al. |
| 9,456,812 B2 | 10/2016 | Finch et al. |
| 9,550,022 B2 | 1/2017 | Brenneman et al. |
| 9,649,480 B2 | 5/2017 | Sugimoto et al. |
| 9,662,021 B2 | 5/2017 | Chow et al. |
| 9,681,948 B2 | 6/2017 | Levi et al. |
| 9,693,800 B2 | 7/2017 | Aman et al. |
| 9,775,636 B2 | 10/2017 | Fazio et al. |
| 9,789,294 B2 | 10/2017 | Taft et al. |
| 9,814,483 B2 | 11/2017 | Vardi |
| 9,827,404 B2 | 11/2017 | Nance et al. |
| 9,839,517 B2 | 12/2017 | Centola et al. |
| 9,872,981 B2 | 1/2018 | Sparks et al. |
| 9,980,815 B2 | 5/2018 | Nitzan et al. |
| 9,999,528 B2 | 6/2018 | Kim et al. |
| 10,076,403 B1 | 9/2018 | Eigler et al. |
| 10,130,371 B2 | 11/2018 | Dehdashtian et al. |
| 10,272,230 B2 | 4/2019 | Malek et al. |
| 10,292,690 B2 | 5/2019 | Celermajer et al. |
| 10,327,746 B2 | 6/2019 | Glimsdale et al. |
| 10,413,284 B2 | 9/2019 | McNamara et al. |
| 10,426,482 B2 | 10/2019 | Rafiee et al. |
| 10,426,497 B2 | 10/2019 | Chou et al. |
| 10,433,851 B2 | 10/2019 | Adams et al. |
| 10,456,259 B2 | 10/2019 | Subramanian et al. |
| 10,543,113 B2 | 1/2020 | Vong et al. |
| 10,561,423 B2 | 2/2020 | Sharma |
| 10,565,835 B2 | 2/2020 | Harrington et al. |
| 10,568,751 B2 | 2/2020 | McNamara |
| 10,595,999 B2 | 3/2020 | Vettukattil et al. |
| 10,709,451 B2 | 7/2020 | Gronberg et al. |
| 10,835,394 B2 | 11/2020 | Nae et al. |
| 10,898,698 B1 | 1/2021 | Eigler et al. |
| 10,912,585 B2 | 2/2021 | Kleyman |
| 10,925,731 B2 | 2/2021 | Bishop et al. |
| 10,925,756 B2 | 2/2021 | Perszyk |
| 10,940,296 B2 | 3/2021 | Keren |
| 11,135,054 B2 | 10/2021 | Nitzan et al. |
| 11,135,410 B2 | 10/2021 | Finch et al. |
| 11,234,702 B1 | 2/2022 | Eigler et al. |
| 11,291,807 B2 | 4/2022 | Eigler et al. |
| 11,298,117 B2 | 4/2022 | Hariton et al. |
| 11,304,698 B2 | 4/2022 | Sharma |
| 11,395,644 B2 | 7/2022 | Alanbaei |
| 11,420,034 B2 | 8/2022 | Solomon et al. |
| 2001/0000041 A1 | 3/2001 | Selmon et al. |
| 2001/0025643 A1 | 10/2001 | Foley |
| 2001/0035183 A1 | 11/2001 | Sexton et al. |
| 2001/0045698 A1 | 11/2001 | Lo |
| 2002/0013616 A1 | 1/2002 | Carter et al. |
| 2002/0029079 A1 | 3/2002 | Kim et al. |
| 2002/0062146 A1 | 5/2002 | Makower et al. |
| 2002/0128546 A1 | 9/2002 | Silver |
| 2002/0138009 A1 | 9/2002 | Brockway et al. |
| 2002/0169466 A1 | 11/2002 | Peterson et al. |
| 2002/0193751 A1 | 12/2002 | Theeuwes et al. |
| 2002/0198501 A1 | 12/2002 | Kumar et al. |
| 2003/0017150 A1 | 1/2003 | Torphy |
| 2003/0060876 A1 | 3/2003 | Loshakove et al. |
| 2003/0065345 A1 | 4/2003 | Weadock |
| 2003/0181928 A1 | 9/2003 | Vidlund et al. |
| 2003/0225425 A1 | 12/2003 | Kupiecki et al. |
| 2004/0064081 A1 | 4/2004 | Stanish |
| 2004/0082738 A1 | 4/2004 | Dolle et al. |
| 2004/0087997 A1 | 5/2004 | Brenneman |
| 2004/0092879 A1 | 5/2004 | Kraus et al. |
| 2004/0098105 A1 | 5/2004 | Stinson et al. |
| 2004/0158143 A1 | 8/2004 | Flaherty et al. |
| 2004/0215168 A1 | 10/2004 | Verrier et al. |
| 2004/0215220 A1 | 10/2004 | Dolan et al. |
| 2004/0215323 A1 | 10/2004 | Stiger |
| 2004/0230156 A1 | 11/2004 | Schreck et al. |
| 2004/0260318 A1 | 12/2004 | Hunter et al. |
| 2005/0021085 A1 | 1/2005 | Abrams et al. |
| 2005/0033239 A1 | 2/2005 | Argentine |
| 2005/0038501 A1 | 2/2005 | Moore et al. |
| 2005/0043708 A1 | 2/2005 | Gleeson et al. |
| 2005/0049675 A1 | 3/2005 | Wallace |
| 2005/0060041 A1 | 3/2005 | Phan et al. |
| 2005/0065469 A1 | 3/2005 | Tal |
| 2005/0075655 A1 | 4/2005 | Bumbalough et al. |
| 2005/0075656 A1 | 4/2005 | Beaupre |
| 2005/0082226 A1 | 4/2005 | Bene et al. |
| 2005/0107723 A1 | 5/2005 | Wehman et al. |
| 2005/0149096 A1 | 7/2005 | Hilal et al. |
| 2005/0165344 A1 | 7/2005 | Dobak |
| 2005/0228402 A1 | 10/2005 | Hofmann |
| 2005/0249770 A1 | 11/2005 | Hunter |
| 2005/0249776 A1 | 11/2005 | Chen et al. |
| 2005/0267490 A1 | 12/2005 | Secrest et al. |
| 2005/0272806 A1 | 12/2005 | Falotico et al. |
| 2005/0277965 A1 | 12/2005 | Brenneman et al. |
| 2006/0020324 A1 | 1/2006 | Schmid et al. |
| 2006/0024359 A1 | 2/2006 | Walker et al. |
| 2006/0034466 A1 | 2/2006 | Form et al. |
| 2006/0041270 A1 | 2/2006 | Lenker et al. |
| 2006/0074398 A1 | 4/2006 | Whiting et al. |
| 2006/0111704 A1 | 5/2006 | Brenneman et al. |
| 2006/0130591 A1 | 6/2006 | Perkins |
| 2006/0130767 A1 | 6/2006 | Herchen |
| 2006/0182536 A1 | 8/2006 | Rice et al. |
| 2006/0198869 A1 | 9/2006 | Furst et al. |
| 2006/0241342 A1 | 10/2006 | Macaulay et al. |
| 2006/0264801 A1 | 11/2006 | Bolling et al. |

(56) References Cited

U.S. PATENT DOCUMENTS

| | | | |
|---|---|---|---|
| 2006/0265042 A1 | 11/2006 | Catanese et al. |
| 2006/0271196 A1 | 11/2006 | Saal et al. |
| 2006/0293701 A1 | 12/2006 | Ainsworth et al. |
| 2007/0021730 A1 | 1/2007 | Flaherty et al. |
| 2007/0083258 A1 | 4/2007 | Falotico et al. |
| 2007/0173787 A1 | 7/2007 | Huang et al. |
| 2007/0179426 A1 | 8/2007 | Selden |
| 2007/0213750 A1 | 9/2007 | Weadock |
| 2008/0021485 A1 | 1/2008 | Catanese et al. |
| 2008/0027532 A1 | 1/2008 | Boylan et al. |
| 2008/0051883 A1 | 2/2008 | Llanos et al. |
| 2008/0071178 A1 | 3/2008 | Greenland et al. |
| 2008/0091264 A1 | 4/2008 | Machold et al. |
| 2008/0109069 A1 | 5/2008 | Coleman et al. |
| 2008/0161904 A1 | 7/2008 | Heuser et al. |
| 2008/0167595 A1 | 7/2008 | Porter et al. |
| 2008/0234842 A1 | 9/2008 | Zhang |
| 2009/0005656 A1 | 1/2009 | Najafi et al. |
| 2009/0105654 A1 | 4/2009 | Kurth et al. |
| 2009/0125097 A1 | 5/2009 | Bruszewski et al. |
| 2009/0143713 A1 | 6/2009 | Van Dam et al. |
| 2009/0149947 A1 | 6/2009 | Frohwitter |
| 2009/0187116 A1 | 7/2009 | Noishiki et al. |
| 2009/0187131 A1 | 7/2009 | Fitzgerald et al. |
| 2009/0234293 A1 | 9/2009 | Albrecht et al. |
| 2009/0281379 A1 | 11/2009 | Binmoeller et al. |
| 2010/0016797 A1 | 1/2010 | Rockrohr |
| 2010/0030321 A1 | 2/2010 | Mach |
| 2010/0106171 A1 | 4/2010 | Arepally et al. |
| 2010/0130810 A1 | 5/2010 | Mohl |
| 2010/0198041 A1 | 8/2010 | Christian et al. |
| 2010/0217382 A1 | 8/2010 | Chau et al. |
| 2010/0262036 A1* | 10/2010 | Najafi ................... A61B 5/031 |
| | | 600/561 |
| 2010/0298930 A1 | 11/2010 | Orlov |
| 2011/0096036 A1 | 4/2011 | McIntosh et al. |
| 2011/0106118 A1 | 5/2011 | Son et al. |
| 2011/0251482 A1 | 10/2011 | Kellerman et al. |
| 2011/0306916 A1 | 12/2011 | Nitzan et al. |
| 2012/0029598 A1 | 2/2012 | Zhao |
| 2012/0041544 A1 | 2/2012 | Wolf |
| 2012/0053686 A1 | 3/2012 | McNamara et al. |
| 2012/0108986 A1 | 5/2012 | Beasley et al. |
| 2012/0143141 A1 | 6/2012 | Verkaik et al. |
| 2012/0265229 A1 | 10/2012 | Rottenberg et al. |
| 2012/0265296 A1* | 10/2012 | McNamara ............ A61B 17/11 |
| | | 604/503 |
| 2013/0022214 A1 | 1/2013 | Dickins et al. |
| 2013/0030521 A1 | 1/2013 | Nitzan et al. |
| 2013/0046152 A1 | 2/2013 | Najafi et al. |
| 2013/0178750 A1* | 7/2013 | Sheehan .............. A61B 5/0215 |
| | | 604/9 |
| 2013/0178784 A1 | 7/2013 | McNamara et al. |
| 2013/0225997 A1 | 8/2013 | Dillard et al. |
| 2013/0253342 A1 | 9/2013 | Griswold et al. |
| 2013/0281988 A1 | 10/2013 | Magnin et al. |
| 2014/0094836 A1 | 4/2014 | Feng et al. |
| 2014/0183828 A1 | 7/2014 | Xu et al. |
| 2014/0203939 A1 | 7/2014 | Harrington et al. |
| 2014/0222040 A1 | 8/2014 | Park et al. |
| 2014/0276395 A1 | 9/2014 | Wilson et al. |
| 2014/0277054 A1 | 9/2014 | McNamara et al. |
| 2014/0278442 A1 | 9/2014 | Hong et al. |
| 2014/0350523 A1 | 11/2014 | Dehdashtian et al. |
| 2015/0119796 A1 | 4/2015 | Finch |
| 2015/0148731 A1 | 5/2015 | McNamara et al. |
| 2015/0151101 A1 | 6/2015 | Bonnette et al. |
| 2015/0157268 A1 | 6/2015 | Winshtein et al. |
| 2015/0238729 A1 | 8/2015 | Jenson et al. |
| 2016/0022293 A1 | 1/2016 | Dubrul et al. |
| 2016/0022970 A1 | 1/2016 | Forcucci et al. |
| 2016/0045165 A1* | 2/2016 | Braido .................. A61F 2/2412 |
| | | 623/2.1 |
| 2016/0058452 A1 | 3/2016 | Brenneman et al. |
| 2016/0120550 A1 | 5/2016 | McNamara et al. |

| | | | |
|---|---|---|---|
| 2016/0151615 A1 | 6/2016 | Overtoom |
| 2016/0198996 A1 | 7/2016 | Dullen |
| 2016/0220357 A1 | 8/2016 | Anand et al. |
| 2016/0256107 A1 | 9/2016 | Gupta et al. |
| 2016/0270810 A1 | 9/2016 | Vardi et al. |
| 2016/0296317 A1 | 10/2016 | Timmermans et al. |
| 2016/0323977 A1 | 11/2016 | Sun et al. |
| 2016/0331468 A1 | 11/2016 | Lee et al. |
| 2016/0338823 A1 | 11/2016 | Akingba |
| 2016/0346448 A1 | 12/2016 | Kaiser et al. |
| 2017/0090865 A1 | 3/2017 | Armstrong-Muntner et al. |
| 2017/0105839 A1 | 4/2017 | Subramanian et al. |
| 2017/0106176 A1* | 4/2017 | Taft ..................... A61M 27/008 |
| 2017/0113026 A1 | 4/2017 | Finch |
| 2017/0128705 A1 | 5/2017 | Forcucci et al. |
| 2017/0196565 A1 | 7/2017 | Tuseth et al. |
| 2017/0258585 A1 | 9/2017 | Marquez et al. |
| 2017/0303959 A1 | 10/2017 | Feng et al. |
| 2017/0319823 A1 | 11/2017 | Yacoby et al. |
| 2017/0340460 A1 | 11/2017 | Rosen et al. |
| 2018/0035971 A1 | 2/2018 | Brenner et al. |
| 2018/0140444 A1 | 5/2018 | Neuss et al. |
| 2018/0177516 A1 | 6/2018 | Vardi et al. |
| 2018/0185153 A1 | 7/2018 | Bishop et al. |
| 2018/0207412 A1 | 7/2018 | Malek et al. |
| 2018/0214269 A1 | 8/2018 | Wilson et al. |
| 2018/0243071 A1 | 8/2018 | Eigler et al. |
| 2018/0256865 A1 | 9/2018 | Finch et al. |
| 2019/0008628 A1 | 1/2019 | Eigler et al. |
| 2019/0083228 A1 | 3/2019 | Dickinson et al. |
| 2019/0134350 A1 | 5/2019 | Crisco et al. |
| 2019/0269392 A1 | 9/2019 | Celermajer et al. |
| 2019/0298909 A1 | 10/2019 | Cully et al. |
| 2019/0336339 A1 | 11/2019 | Reo et al. |
| 2019/0351210 A1 | 11/2019 | Solomon et al. |
| 2020/0054867 A1 | 2/2020 | Schwartz et al. |
| 2020/0085600 A1 | 3/2020 | Schwartz et al. |
| 2020/0101270 A1 | 4/2020 | Sutherland |
| 2020/0170662 A1 | 6/2020 | Vardi et al. |
| 2020/0187945 A1 | 6/2020 | Rowe et al. |
| 2020/0230362 A1 | 7/2020 | Basude |
| 2020/0254228 A1 | 8/2020 | Taft et al. |
| 2020/0261704 A1 | 8/2020 | Wang et al. |
| 2020/0289196 A1 | 9/2020 | Arevalos et al. |
| 2020/0315599 A1 | 10/2020 | Nae et al. |
| 2020/0368505 A1 | 11/2020 | Nae et al. |
| 2020/0391016 A1 | 12/2020 | Passman et al. |
| 2021/0007790 A1 | 1/2021 | Takahashi et al. |
| 2021/0007791 A1 | 1/2021 | Takahashi et al. |
| 2021/0007800 A1 | 1/2021 | Takahashi et al. |
| 2021/0022855 A1 | 1/2021 | Tegels et al. |
| 2021/0045691 A1 | 2/2021 | Zou et al. |
| 2021/0052877 A1 | 2/2021 | Muldoon et al. |
| 2021/0059650 A1 | 3/2021 | Eidenschink et al. |
| 2021/0077186 A1 | 3/2021 | Pate et al. |
| 2021/0085935 A1 | 3/2021 | Fahey et al. |
| 2021/0092522 A1 | 3/2021 | Draper et al. |
| 2021/0113824 A1 | 4/2021 | Chng et al. |
| 2021/0121179 A1 | 4/2021 | Ben-David et al. |
| 2021/0137635 A1 | 5/2021 | Gomez et al. |
| 2021/0153776 A1 | 5/2021 | Minar et al. |
| 2021/0161637 A1 | 6/2021 | Eigler et al. |
| 2021/0177508 A1 | 6/2021 | Kellerman |
| 2021/0213269 A1 | 7/2021 | Venskytis et al. |
| 2021/0236138 A1 | 8/2021 | Perszyk et al. |
| 2021/0259671 A1 | 8/2021 | DiCicco et al. |
| 2021/0290214 A1 | 9/2021 | Cole et al. |
| 2021/0361238 A1 | 11/2021 | Bak-Boychuk et al. |
| 2021/0369321 A1 | 12/2021 | Yang et al. |
| 2021/0401494 A1 | 12/2021 | Passman et al. |
| 2022/0001154 A1 | 1/2022 | Rowe et al. |
| 2022/0008014 A1 | 1/2022 | Rowe et al. |
| 2022/0031327 A1 | 2/2022 | Manash et al. |
| 2022/0039667 A1 | 2/2022 | Schmitt et al. |
| 2022/0039671 A1 | 2/2022 | Fahey |
| 2022/0039833 A1 | 2/2022 | Thai et al. |
| 2022/0088355 A1 | 3/2022 | Rabito et al. |
| 2022/0096087 A1 | 3/2022 | Valdez |
| 2022/0110679 A1 | 4/2022 | Wang et al. |

(56)  References Cited

U.S. PATENT DOCUMENTS

| | | |
|---|---|---|
| 2022/0142652 A1 | 5/2022 | Alexander et al. |
| 2022/0151784 A1 | 5/2022 | Eigler et al. |
| 2022/0168015 A1 | 6/2022 | Murray et al. |
| 2022/0184356 A1 | 6/2022 | Nae et al. |
| 2022/0202443 A1 | 6/2022 | Thai et al. |
| 2022/0203077 A1 | 6/2022 | Folan |
| 2022/0203078 A1 | 6/2022 | May |
| 2022/0211380 A1 | 7/2022 | Pate |
| 2022/0218352 A1 | 7/2022 | O'Halloran et al. |
| 2022/0218964 A1 | 7/2022 | Fahey et al. |
| 2022/0241564 A1 | 8/2022 | Shang et al. |
| 2022/0241565 A1 | 8/2022 | Nae et al. |
| 2022/0249285 A1 | 8/2022 | Chang et al. |
| 2022/0257904 A1 | 8/2022 | Passman et al. |
| 2022/0273279 A1 | 9/2022 | Valdez et al. |
| 2022/0280160 A1 | 9/2022 | Sharma |
| 2022/0280760 A1 | 9/2022 | Thai et al. |
| 2022/0296865 A1 | 9/2022 | Rafiee et al. |
| 2022/0313234 A1 | 10/2022 | McNamara et al. |
| 2022/0323012 A1 | 10/2022 | Pool et al. |
| 2022/0323196 A1 | 10/2022 | Rafiee et al. |
| 2022/0346936 A1 | 11/2022 | Scutti et al. |
| 2022/0347446 A1 | 11/2022 | Fahey et al. |
| 2022/0370120 A1 | 11/2022 | Yang et al. |
| 2022/0379100 A1 | 12/2022 | Gutierrez et al. |
| 2022/0387009 A1 | 12/2022 | Bukhdruker et al. |
| 2023/0099410 A1 | 3/2023 | Primeaux |
| 2023/0165672 A1 | 6/2023 | Fahey et al. |
| 2023/0181214 A1 | 6/2023 | Vardi et al. |
| 2023/0191093 A1 | 6/2023 | Nae et al. |
| 2023/0233255 A1 | 7/2023 | Takahashi |
| 2023/0263949 A1 | 8/2023 | Passman et al. |
| 2023/0285133 A1 | 9/2023 | Eigler et al. |
| 2023/0330398 A1 | 10/2023 | Nae et al. |
| 2023/0404659 A1 | 12/2023 | Akerele-Ale et al. |
| 2024/0000404 A1 | 1/2024 | Robertson et al. |

FOREIGN PATENT DOCUMENTS

| | | | |
|---|---|---|---|
| CN | 113367839 A | 9/2021 | |
| CN | 113397762 A | 9/2021 | |
| EP | 0904009 A1 | 3/1999 | |
| KR | 20200145957 A | 12/2020 | |
| WO | WO-2005006963 A2 | 1/2005 | |
| WO | 2007028035 A2 | 3/2007 | |
| WO | 2012016157 A1 | 2/2012 | |
| WO | WO-2014150106 A1 | 9/2014 | |
| WO | WO-2015052235 A1 | 4/2015 | |
| WO | 2016178171 A1 | 11/2016 | |
| WO | 2017156175 A2 | 9/2017 | |
| WO | WO-2019035993 A1 | 2/2019 | |
| WO | 2020215090 A1 | 10/2020 | |
| WO | WO-2020232384 A1 | 11/2020 | |
| WO | 2021091566 A1 | 5/2021 | |
| WO | 2022031317 A1 | 2/2022 | |
| WO | 2022060630 A1 | 3/2022 | |
| WO | WO-2022071179 A1 | 4/2022 | |
| WO | 2022133070 A1 | 6/2022 | |
| WO | 2022169865 A1 | 8/2022 | |
| WO | 2022177737 A1 | 8/2022 | |
| WO | 2022197454 A1 | 9/2022 | |
| WO | 2022197455 A1 | 9/2022 | |
| WO | 2022232133 A1 | 11/2022 | |
| WO | 2022246158 A1 | 11/2022 | |
| WO | 2022246166 A1 | 11/2022 | |
| WO | 2022271473 A1 | 12/2022 | |
| WO | 2023022883 A1 | 2/2023 | |
| WO | 2023027926 A1 | 3/2023 | |
| WO | 2023079498 A1 | 5/2023 | |
| WO | 2023081127 A1 | 5/2023 | |
| WO | 2023081129 A1 | 5/2023 | |
| WO | 2023154235 A1 | 8/2023 | |
| WO | 2023154308 A1 | 8/2023 | |
| WO | 2023172435 A1 | 9/2023 | |
| WO | 2023172436 A1 | 9/2023 | |
| WO | 2023196243 A1 | 10/2023 | |
| WO | 2023239784 A1 | 12/2023 | |
| WO | 2023239785 A1 | 12/2023 | |
| WO | 2023239788 A2 | 12/2023 | |
| WO | WO-2024076579 A1 | 4/2024 | |

OTHER PUBLICATIONS

Emil Mantini, MD, et al., Title: Congenital Anomalies Involving the Coronary Sinus, Circulation, Journal of the American Heart Association, vol. XXXIII, Feb. 1966, pp. 317-327.

Kong, et al.—Creation of an Intra-atrial Communication With a New Amplatzer Shunt Prosthesis, Catheterization and Cardiovascular Interventions 56:267-271 (2002).

P.K. Kong, et al., Title: Unroofed Coronary Sinus and Persistent Left Superior Vena Cava, The European Society of Cardiology, 2006, pp. 398401.

Ruebben et al., "Arteriovenous fistulas induced by femoral arterial catheterization: percuntaneous treatment," Radiology, 209:729, 1998.

Vandhana Scheller, et al., Title: Coronary Sinus to Left Atrial Communication, Case Report in Medicine, Ohio Heart and Vascular Center, vol. 2009, Article ID 790715, pp. 13.

Chow et al, "Toward an Implantable Wireless Cardiac Monitoring Platform Integrated with an FDA-Approved Cardiovascular Stent", Journal of Interventional Cardiology, vol. 22, No. 5, 2009, pp. 479-487, Wiley Periodicals, Inc., Hoboken, NJ, USA.

Bechtold C., et al., "Method for Fabricating Miniaturized NiTi Self-Expandable Thin Film Devices with Increased Radiopacity", Shape Memory and Superelasticity, 2016, vol. 2, pp. 391-398.

Chao-Chi Y., et al., "Fabrication of a Flexible Wireless Pressure Sensor for Intravascular Blood Pressure Monitoring," Microelectronic Engineering Elsevier Publishers Bv, Amsterdam, NL, Apr. 11, 2019, vol. 213, pp. 55-61, ISSN 0167-9317, XP085679189, Retrieved from URL: http://dx.doi.Org/10.1016/j.mee.2019.04.009.

Justaniah A., et al., "Coronary Sinus to Left Atrium Communication," Journal of Radiology Case Reports, Dec. 1, 2013, vol. 7, No. 12, pp. 16-20, PMID: 24421933, PMCID: PMC3888326, DOI: 10.3941/jrcr.v7i12.1678.

Mahmud E., et al., "Dilation of the Coronary Sinus on Echocardiogram: Prevalence and Significance in Patients with Chronic Pulmonary Hypertension," Journal of the American Society of Echocardiography, Jan. 2001, vol. 14, No. 1, pp. 44-49, PMID: 11174433, DOI: 10.1067/mje.2001.108538.

* cited by examiner

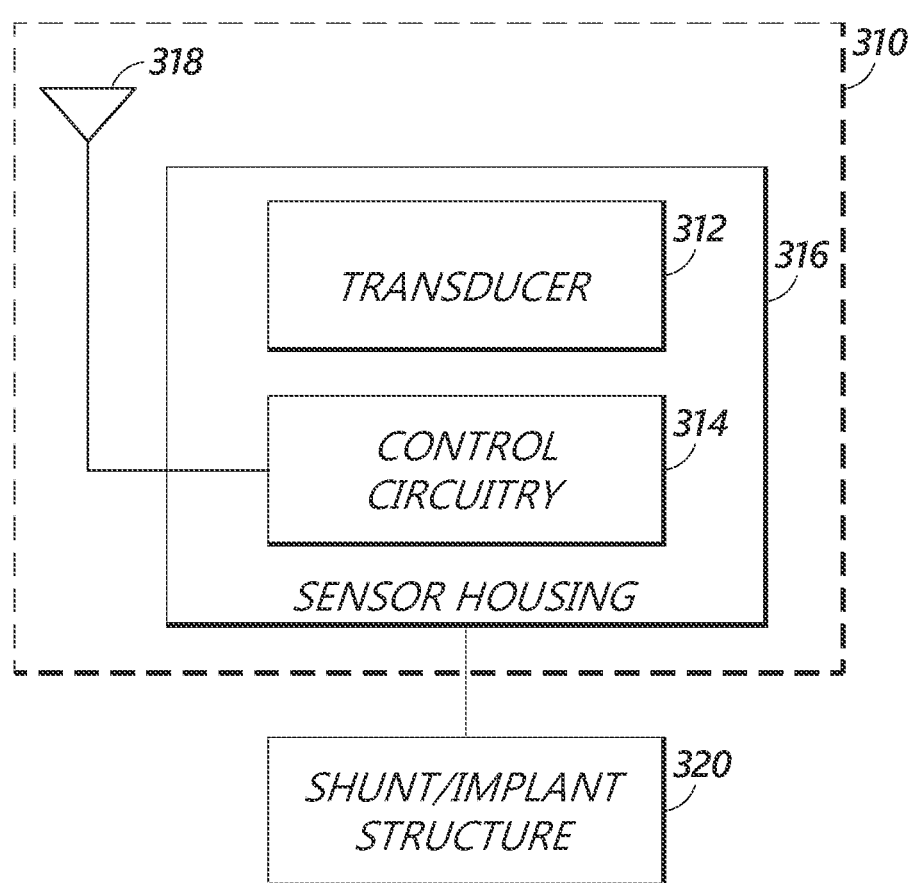
*FIG. 3*

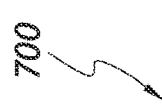
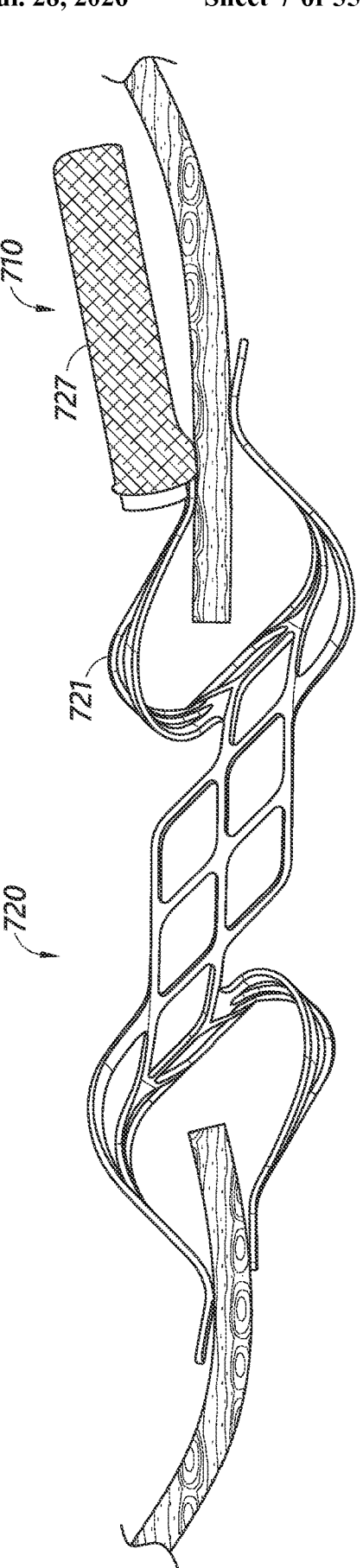
*FIG. 7*

1301

1300

1322

1320

1321

1312

1318

CARDIAC IMPLANT DEVICES WITH INTEGRATED PRESSURE SENSING

RELATED APPLICATION

This application is a National Stage of International Patent Application No. PCT/US2019/065148, filed Dec. 9, 2019, which claims the benefit of U.S. Provisional Application No. 62/778,561, filed on Dec. 12, 2018, entitled CARDIAC IMPLANT DEVICES WITH INTEGRATED PRESSURE SENSING, the disclosures of which are hereby incorporated by reference in their entirety.

BACKGROUND

Field

The present disclosure generally relates to the field of medical implant devices.

Description of Related Art

Various medical procedures involve the implantation of medical implant devices within the anatomy of the heart. Certain physiological parameters associated with such anatomy, such as fluid pressure, can have an impact on patient health prospects.

SUMMARY

Described herein are one or more methods and/or devices to facilitate pressure sensing in cardiac anatomy.

In some implementations, the present disclosure relates to a sensor implant device comprising a shunt structure comprising a flow path conduit and a plurality of arms configured to secure the shunt structure to a tissue wall and a pressure sensor device attached to one of the plurality of arms of the shunt structure. The pressure sensor device comprises one or more sensor elements, an antenna, control circuitry electrically coupled to the one or more sensor elements and the antenna, and a housing that houses the control circuitry.

The sensor implant device can further comprise a pouch attached to the one of the plurality of arms, the pouch at least partially containing the pressure sensor device. In some embodiments, the one of the plurality of arms has a support extension and the pressure sensor device is attached to the support extension. For example, the support extension can have one or more retention features that wrap at least partially around the pressure sensor device.

In some embodiments, the housing has a cylindrical form with a proximal end portion and a distal end portion, and the one or more sensor elements comprises a first sensor element disposed at the proximal end and a second sensor element disposed at the distal end. In some embodiments, the housing has a cylindrical form, the antenna comprises a cylindrical ferrite core and a conductive wire coil wrapped around the ferrite core, and the antenna is housed within the housing.

The antenna can be electrically coupled to the control circuitry via a tether. For example, the antenna can be a flat spiral antenna. In some embodiments, the antenna is disposed at least partially within a hermetically-sealed flexible membrane. The antenna may be wrapped around the flow path conduit of the shunt structure.

In some implementations, the present disclosure relates to a sensor implant device comprising a shunt structure comprising a flow path conduit and a plurality of arms configured to secure the shunt structure to a tissue wall, a netting attached to the shunt structure and at least partially covering a flow path of the flow path conduit, and a sensor device attached to the netting at an attachment point. The sensor device may be attached to a distal side of the netting, such that the sensor device is contained within the netting when the netting is drawn through the flow path conduit and at least partially outside of the netting when the attachment point is disposed on a distal side of the flow path conduit.

In some embodiments, the netting comprises a memory metal mesh having openings therein to allow fluid flow therethrough. The netting may be configured to contain the sensor device and pull the sensor device behind the shunt structure when passed through a lumen of a delivery catheter. In some embodiments, the attachment point is associated with a first end of the sensor device and the sensor device comprises a sensor element associated with a second end of the sensor device that is opposite the first end. The netting may be configured to be cinched, wherein cinching of the netting reduces a distance between the sensor device and the flow path conduit.

In some implementations, the present disclosure relates to a sensor implant device comprising a shunt structure comprising a flow path conduit and a sensor device attached to the flow path conduit. The sensor device comprises a first sensor element disposed a first end of the sensor device that is disposed on a first side of the flow path conduit with respect to a flow path axis, a second sensor element disposed at a second end of the sensor device that is disposed on a second side of the flow path conduit with respect to the flow path axis, a housing, an antenna disposed within the housing, and control circuitry electrically coupled to the first sensor element, the second sensor element, and the antenna, the control circuitry being disposed within the housing. In some embodiments, the sensor device is secured within a receptacle associated with an outside surface of the flow path conduit.

In some implementations, the present disclosure relates to a method of implanting a pressure sensor device. The method comprises implanting a stent in a coronary sinus of a heart, forming an opening in a tissue wall separating the coronary sinus from a left atrium of the heart, passing a pressure sensor device through the opening, and securing the pressure sensor device to the stent. In some embodiments, after securing the pressure sensor device, the pressure sensor device extends substantially orthogonally with respect to a flow path axis of the stent.

In some implementations, the present disclosure relates to a method of implanting a pressure sensor device. The method comprises advancing a guide wire into a right atrium of a heart, through a coronary sinus of the heart, and into a left atrium of the heart via an opening in a tissue wall separating the coronary sinus from the left atrium, approximating the guide wire to a target tissue wall within the left atrium, deploying a shunt structure in the tissue wall separating the coronary sinus from the left atrium using the guide wire, advancing a delivery catheter at least partially containing a pressure sensor device into the left atrium using the guide wire, approximating the pressure sensor device to the target tissue wall within the left atrium, and attaching the pressure sensor device to the target tissue wall. In some embodiments, the delivery catheter comprises a side-running guide-wire-engagement feature.

In some implementations, the present disclosure relates to a method of implanting a pressure sensor device. The method comprises advancing a guide wire into a right atrium of a heart, through a coronary sinus of the heart, and into a left atrium of the heart via an opening in a tissue wall separating the coronary sinus from the left atrium, the guide wire having a sensor device attached thereto, deploying a shunt structure in the tissue wall using the guide wire, the shunt structure having a sensor engagement feature, and after said deploying the shunt structure, pulling the guide wire to engage the sensor device with the sensor engagement feature, thereby securing the sensor device to the shunt structure. In some embodiments, the sensor device has a corresponding engagement feature configured to mate with the engagement feature of the shunt structure.

For purposes of summarizing the disclosure, certain aspects, advantages and novel features have been described herein. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements. However, it should be understood that the use of similar reference numbers in connection with multiple drawings does not necessarily imply similarity between respective embodiments associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some embodiments or configurations.

FIG. 3 is a block diagram of an implant device in accordance with one or more embodiments.

FIG. 7 illustrates a sensor implant device having an integrated sensor in accordance with one or more embodiments.

DETAILED DESCRIPTION

Figure 1:
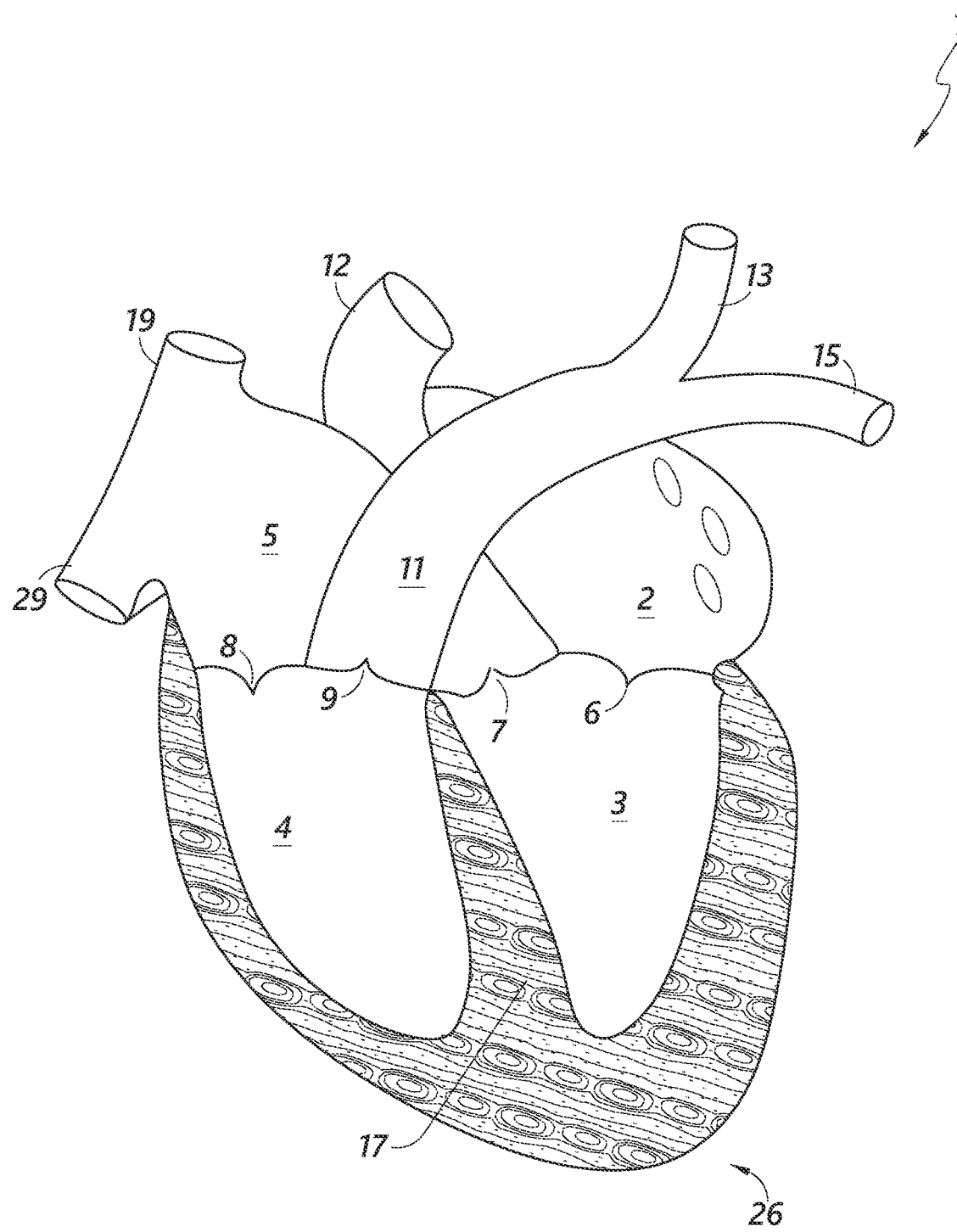
FIG. 1 is a cross-sectional view of a human heart.

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/ element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Furthermore, references may be made herein to certain anatomical planes, such as the sagittal plane, or median plane, or longitudinal plane, referring to a plane parallel to the sagittal suture, and/or other sagittal planes (i.e., para-sagittal planes) parallel thereto. In addition, "frontal plane," or "coronal plane." may refer to an X-Y plane that is perpendicular to the ground when standing, which divides the body into back and front, or posterior and anterior, portions. Furthermore, a "transverse plane," or "cross-sectional plane," or horizontal plane, may refer to an X-Z plane that is parallel to the ground when standing, that divides the body in upper and lower portions, such as superior and inferior. A "longitudinal plane" may refer to any plane perpendicular to the transverse plane. Furthermore, various axes may be described, such as a longitudinal axis, which may refer to an axis that is directed towards head of a human in the cranial direction and/or directed towards inferior of a human in caudal direction. A left-right or horizontal axis, which may refer to an axis that is directed towards the left-hand side and/or right-hand side of a patient. An antero-posterior axis which may refer to an axis that is directed towards the belly of a human in the anterior direction and/or directed towards the back of a human in the posterior direction.

The present disclosure relates to systems, devices, and methods for telemetric pressure monitoring in connection with cardiac shunts and/or other medical implant devices and/or procedures. Such pressure monitoring may be performed using cardiac implant devices having integrated pressure sensors and/or associated components. For example, in some implementations, the present disclosure relates to cardiac shunts and/or other cardiac implant devices that incorporate or are associated with pressure sensors or other sensor devices. Certain embodiments are disclosed herein in the context of cardiac implant devices. However, although certain principles disclosed herein are particularly applicable to the anatomy of the heart, it should be understood that sensor implant devices in accordance with the present disclosure may be implanted in, or configured for implantation in, any suitable or desirable anatomy.

The anatomy of the heart is described below to assist in the understanding of certain inventive concepts disclosed herein. In humans and other vertebrate animals, the heart generally comprises a muscular organ having four pumping chambers, wherein the flow thereof is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.). The contraction of the various heart muscles may be prompted by signals generated by the electrical system of the heart, which is discussed in detail below. Certain embodiments disclosed herein relate to conditions of the heart, such as atrial fibrillation and/or complications or solutions associated therewith. However, embodiments of the present disclosure relate more generally to any health complications relating to fluid overload in a patient, such as may result post-operatively after any surgery involving fluid supplementation. That is, detection of atrial stretching as described herein may be implemented to detect/determine a fluid-overload condition, which may direct treatment or compensatory action relating to atrial fibrillation and/or any other condition caused at least in part by fluid overloading.

FIG. 1 illustrates an example representation of a heart 1 having various features relevant to certain embodiments of the present inventive disclosure. The heart 1 includes four chambers, namely the left atrium 2, the left ventricle 3, the right ventricle 4, and the right atrium 5. In terms of blood flow, blood generally flows from the right ventricle 4 into the pulmonary artery via the pulmonary valve 9, which separates the right ventricle 4 from the pulmonary artery 11 and is configured to open during systole so that blood may be pumped toward the lungs and close during diastole to prevent blood from leaking back into the heart from the pulmonary artery 11. The pulmonary artery 11 carries deoxygenated blood from the right side of the heart to the lungs. The pulmonary artery 11 includes a pulmonary trunk and left 15 and right 13 pulmonary arteries that branch off of the pulmonary trunk, as shown. In addition to the pulmonary valve 9, the heart 1 includes three additional valves for aiding the circulation of blood therein, including the tricuspid valve 8, the aortic valve 7, and the mitral valve 6. The tricuspid valve 8 separates the right atrium 5 from the right ventricle 4. The tricuspid valve 8 generally has three cusps or leaflets and may generally close during ventricular contraction (i.e., systole) and open during ventricular expansion (i.e., diastole). The mitral valve 6 generally has two cusps/leaflets and separates the left atrium 2 from the left ventricle 3. The mitral valve 6 is configured to open during diastole so that blood in the left atrium 2 can flow into the left ventricle 3, and, when functioning properly, closes during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

The heart valves may generally comprise a relatively dense fibrous ring, referred to herein as the annulus, as well as a plurality of leaflets or cusps attached to the annulus. Generally, the size of the leaflets or cusps may be such that when the heart contracts the resulting increased blood pressure produced within the corresponding heart chamber forces the leaflets at least partially open to allow flow from the heart chamber. As the pressure in the heart chamber subsides, the pressure in the subsequent chamber or blood vessel may become dominant and press back against the leaflets. As a result, the leaflets/cusps come in apposition to each other, thereby closing the flow passage. Disfunction of a heart valve and/or associated leaflets (e.g., pulmonary valve disfunction) can result in valve leakage and/or other health complications.

The atrioventricular (i.e., mitral and tricuspid) heart valves may further comprise a collection of chordae tendineae and papillary muscles (not shown) for securing the leaflets of the respective valves to promote and/or facilitate proper coaptation of the valve leaflets and prevent prolapse thereof. The papillary muscles, for example, may generally comprise finger-like projections from the ventricle wall. The valve leaflets are connected to the papillary muscles by the chordae tendineae. A wall of muscle 17, referred to as the septum, separates the left 2 and right 5 atria and the left 3 and right 4 ventricles.

Congestive Heart Failure

As referenced above, certain physiological conditions or parameters associated with the cardiac anatomy can impact the health of a patient. For example, congestive heart failure is a condition associated with the relatively slow movement of blood through the heart and/or body, which causes the fluid pressure in one or more chambers of the heart to increase. As a result, the heart does not pump sufficient oxygen to meet the body's needs. The various chambers of the heart may respond to pressure increases by stretching to hold more blood to pump through the body or by becoming relatively stiff and/or thickened. The walls of the heart can eventually weaken and become unable to pump as efficiently. In some cases, the kidneys may respond to cardiac inefficiency by causing the body to retain fluid. Fluid build-up in arms, legs, ankles, feet, lungs, and/or other organs can cause the body to become congested, which is referred to as congestive heart failure. Acute decompensated congestive heart failure is a leading cause of morbidity and mortality, and therefore treatment and/or prevention of congestive heart failure is a significant concern in medical care.

The treatment and/or prevention of heart failure (e.g., congestive heart failure) can advantageously involve the monitoring of pressure in one or more chambers or regions of the heart or other anatomy. As described above, pressure buildup in one or more chambers or areas of the heart can be associated with congestive heart failure. Without direct or indirect monitoring of cardiac pressure, it can be difficult to infer, determine, or predict the presence or occurrence of congestive heart failure. For example, treatments or approaches not involving direct or indirect pressure monitoring may involve measuring or observing other present physiological conditions of the patient, such as measuring body weight, thoracic impedance, right heart catheterization, or the like. In some solutions, pulmonary capillary wedge pressure can be measured as a surrogate of left atrial pressure. For example, a pressure sensor may be disposed or implanted in the pulmonary artery, and readings associated therewith may be used as a surrogate for left atrial pressure. However, with respect to catheter-based pressure measurement in the pulmonary artery or certain other chambers or regions of the heart, use of invasive catheters may be required to maintain such pressure sensors, which may be uncomfortable or difficult to implement. Furthermore, certain lung-related conditions may affect pressure readings in the pulmonary artery, such that the correlation between pulmonary artery pressure and left atrial pressure may be undesirably attenuated. As an alternative to pulmonary artery pressure measurement, pressure measurements in the right ventricle outflow tract may relate to left atrial pressure as well. However, the correlation between such pressure readings and left atrial pressure may not be sufficiently strong to be utilized in congestive heart failure diagnostics, prevention, and/or treatment.

Additional solutions may be implemented for deriving or inferring left atrial pressure. For example, the F/A ratio, which is a marker of the function of the left ventricle of the heart representing the ratio of peak velocity blood flow from gravity in early diastole (the E wave) to peak velocity flow in late diastole caused by atrial contraction (the A wave), can be used as a surrogate for measuring left atrial pressure. The F/A ratio may be determined using echocardiography or other imaging technology; generally, abnormalities in the F/A ratio may suggest that the left ventricle cannot fill with blood properly in the period between contractions, which may lead to symptoms of heart failure, as explained above. However, E/A ratio determination generally does not provide absolute pressure measurement values.

Various methods for identifying and/or treating congestive heart failure involve the observation of worsening congestive heart failure symptoms and/or changes in body weight. However, such signs may appear relatively late and/or be relatively unreliable. For example, daily body-weight measurements may vary significantly (e.g., up to 9% or more) and may be unreliable in signaling heart-related complications. Furthermore, treatments guided by monitoring signs, symptoms, weight, and/or other biomarkers have not been shown to substantially improve clinical outcomes. In addition, for patients that have been discharged, such treatments may necessitate remote telemedicine systems.

The present disclosure provides systems, devices, and methods for guiding the administration of medication relating to the treatment of congestive heart failure at least in part by directly monitoring pressure in the left atrium, or other chamber or vessel for which pressure measurements are indicative of left atrial pressure, in congestive heart failure patients in order to reduce hospital readmissions, morbidity, and/or otherwise improve the health prospects of the patient.

Cardiac Pressure Monitoring

Cardiac pressure monitoring in accordance with embodiments the present disclosure may provide a proactive intervention mechanism for preventing or treating congestive heart failure. Generally, increases in ventricular filling pressures associated with diastolic and/or systolic heart failure can occur prior to the occurrence of symptoms that lead to hospitalization. For example, cardiac pressure indicators may present weeks prior to hospitalization with respect to some patients. Therefore, pressure monitoring systems in accordance with embodiments the present disclosure may advantageously be implemented to reduce instances of hospitalization by guiding the appropriate or desired titration and/or administration of medications before the onset of heart failure.

Dyspnea represents a cardiac pressure indicator characterized by shortness of breath or the feeling that one cannot breathe well enough. Dyspnea may result from elevated atrial pressure, which may cause fluid buildup in the lungs from pressure back-up. Pathological dyspnea can result from congestive heart failure. However, a significant amount of time may elapse between the time of initial pressure elevation and the onset of dyspnea, and therefore symptoms of dyspnea may not provide sufficiently-early signaling of elevated atrial pressure. By monitoring pressure directly according to embodiments of the present disclosure, normal ventricular filling pressures may advantageously be maintained, thereby preventing or reducing effects of heart failure, such as dyspnea.

Figure 2:
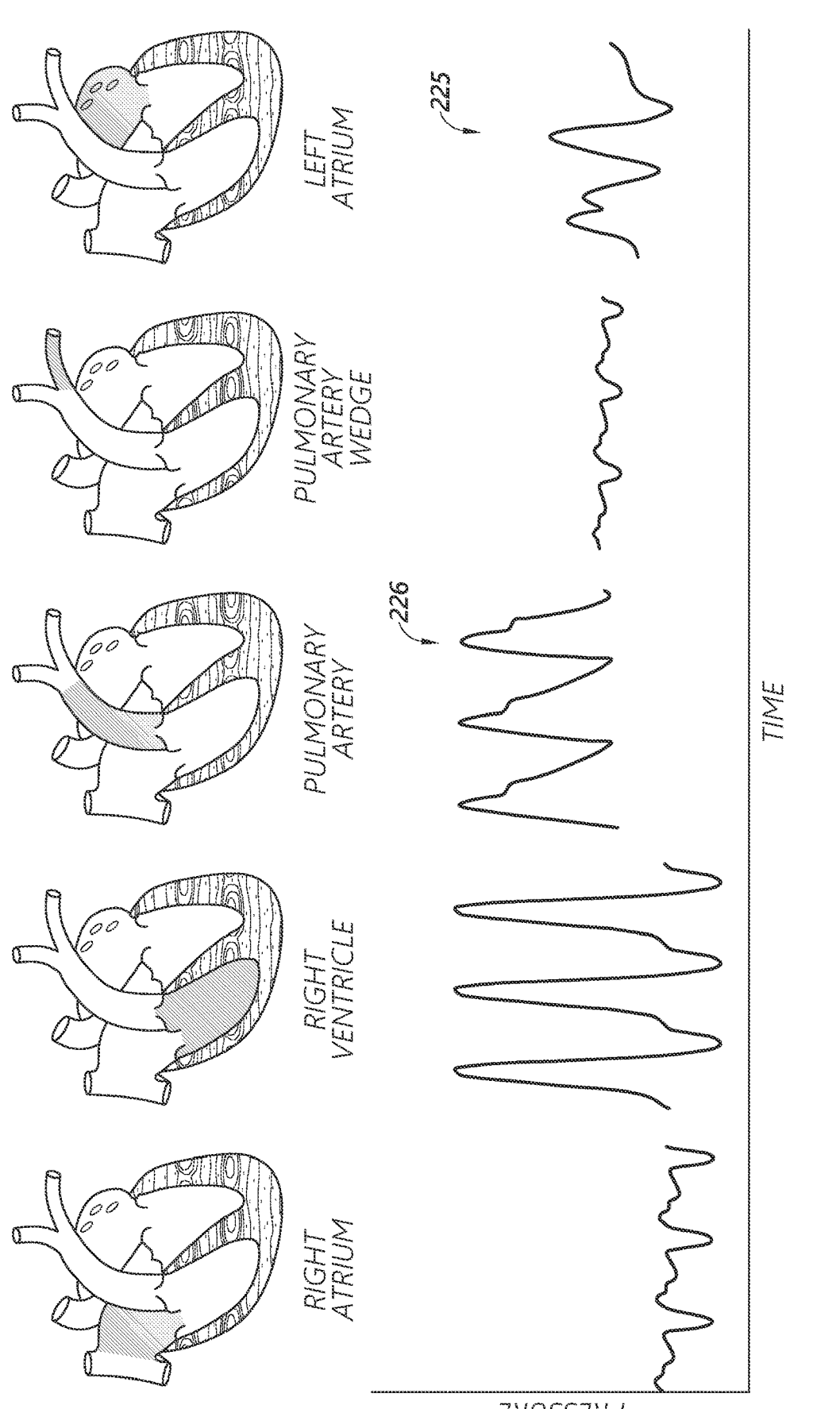
FIG. 2 illustrates example pressure waveforms associated with various chambers and vessels of the heart according to one or more embodiments.

As referenced above, with respect to cardiac pressures, pressure elevation in the left atrium may be particularly correlated with heart failure. FIG. 2 illustrates example pressure waveforms associated with various chambers and vessels of the heart according to one or more embodiments. The various waveforms illustrated in FIG. 2 may represent waveforms obtained using right heart catheterization to advance one or more pressure sensors to the respective illustrated and labeled chambers or vessels of the heart. As illustrated in FIG. 2, the waveform 225, which represents left atrial pressure, may be considered to provide the best feedback for early detection of congestive heart failure. Furthermore, there may generally be a relatively strong correlation between increases and left atrial pressure and pulmonary congestion.

Left atrial pressure may generally correlate well with left ventricular end-diastolic pressure. However, although left atrial pressure and end-diastolic pulmonary artery pressure can have a significant correlation, such correlation may be weakened when the pulmonary vascular resistance becomes elevated. That is, pulmonary artery pressure generally fails to correlate adequately with left ventricular end-diastolic pressure in the presence of a variety of acute conditions, which may include certain patients with congestive heart failure. For example, pulmonary hypertension, which affects approximately 25% to 83% of patients with heart failure, can affect the reliability of pulmonary artery pressure measurement for estimating left-sided filling pressure. Therefore, pulmonary artery pressure measurement alone, as represented by the waveform 226, may be an insufficient or inaccurate indicator of left ventricular end-diastolic pressure, particularly for patients with comorbidities, such as lung disease and/or thromboembolism. Left atrial pressure may further be correlated at least partially with the presence and/or degree of mitral regurgitation.

Left atrial pressure readings may be relatively less likely to be distorted or affected by other conditions, such as respiratory conditions or the like, compared to the other pressure waveforms shown in FIG. 2. Generally, left atrial pressure may be significantly predictive of heart failure, such as up two weeks before manifestation of heart failure. For example, increases in left atrial pressure, and both diastolic and systolic heart failure, may occur weeks prior to hospitalization, and therefore knowledge of such increases may be used to predict the onset of congestive heart failure, such as acute debilitating symptoms of congestive heart failure.

Cardiac pressure monitoring, such as left atrial pressure monitoring, can provide a mechanism to guide administration of medication to treat and/or prevent congestive heart failure. Such treatments may advantageously reduce hospital readmissions and morbidity, as well as provide other benefits. An implanted pressure sensor in accordance with embodiments the present disclosure may be used to predict heart failure up two weeks or more before the manifestation of symptoms or markers of heart failure (e.g., dyspnea). When heart failure predictors are recognized using cardiac pressure sensor embodiments in accordance with the present disclosure, certain prophylactic measures may be implemented, including medication intervention, such as modification to a patient's medication regimen, which may help prevent or reduce the effects of cardiac dysfunction. Direct pressure measurement in the left atrium can advantageously provide an accurate indicator of pressure buildup that may lead to heart failure or other complications. For example, trends of atrial pressure elevation may be analyzed or used to determine or predict the onset of cardiac dysfunction, wherein drug or other therapy may be augmented to cause reduction in pressure and prevent or reduce further complications.

Sensor Implant Devices with Integrated Pressure Sensors

In some implementations, the present disclosure relates to pressure sensors associated or integrated with cardiac shunts or other implant devices. Such integrated devices may be used to provide controlled and/or more effective therapies for treating and preventing heart failure. FIG. 3 is a block diagram illustrating an implant device 300 comprising a shunt (or other type of implant) structure 320. In some embodiments, the shunt structure 320 is physically integrated with and/or connected to a sensor device 310. The sensor device 310 may be, for example, a pressure sensor, or other type of sensor. In some embodiments, the sensor 310 comprises a transducer 312, such as a pressure transducer, as well as certain control circuitry 314, which may be embodied in, for example, an application-specific integrated circuit (ASIC). The control circuitry 314 may be configured to process signals received from the transducer 312 and/or communicate signals associated therewith wirelessly through biological tissue using the antenna 318. The antenna 318 may comprise one or more coils or loops of conductive material, such as copper wire or the like. In some embodiments, at least a portion of the transducer 312, control circuitry 314, and/or the antenna 318 are at least partially disposed or contained within a sensor housing 316, which may comprise any type of material, and may advantageously be at least partially hermetically sealed. For example, the housing 316 may comprise glass or other rigid material in some embodiments, which may provide mechanical stability and/or protection for the components housed therein. In some embodiments, the housing 316 is at least partially flexible. For example, the housing may comprise polymer or other flexible structure/material, which may advantageously allow for folding, bending, or collapsing of the sensor 310 to allow for transportation thereof through a catheter or other introducing means.

The transducer 312 may comprise any type of sensor means or mechanism. For example, the transducer 312 may be a force-collector-type pressure sensor. In some embodiments, the transducer 312 comprises a diaphragm, piston, bourdon tube, bellows, or other strain- or deflection-measuring component(s) to measure strain or deflection applied over an area/surface thereof. The transducer 312 may be associated with the housing 316, such that at least a portion thereof is contained within or attached to the housing 316. The term "associated with" is used herein according to its broad and ordinary meaning. With respect to sensor devices/ components being "associated with" a stent or other implant structure, such terminology may refer to a sensor device or component being physically coupled, attached, or connected to, or integrated with, the implant structure.

In some embodiments, the transducer 312 comprises or is a component of a piezoresistive strain gauge, which may be configured to use a bonded or formed strain gauge to detect strain due to applied pressure, wherein resistance increases as pressure deforms the component/material. The transducer 312 may incorporate any type of material, including but not limited to silicon (e.g., monocrystalline), polysilicon thin film, bonded metal foil, thick film, silicon-on-sapphire, sputtered thin film, and/or the like.

In some embodiments, the transducer 312 comprises or is a component of a capacitive pressure sensor including a diaphragm and pressure cavity configured to form a variable capacitor to detect strain due to pressure applied to the diaphragm. The capacitance of the capacitive pressure sensor may generally decrease as pressure deforms the diaphragm. The diaphragm may comprise any material(s), including but not limited to metal, ceramic, silicon, and the like. In some embodiments, the transducer 312 comprises or is a component of an electromagnetic pressure sensor, which may be configured to measures the displacement of a diaphragm by means of changes in inductance, linear variable displacement transducer (LVDT) functionality, Hall Effect, or eddy current sensing. In some embodiments, the transducer 312 comprises or is a component of a piezoelectric strain sensor. For example, such a sensor may determine strain (e.g., pressure) on a sensing mechanism based on the piezoelectric effect in certain materials, such as quartz. This technology is commonly employed for the measurement of highly dynamic pressures.

In some embodiments, the transducer 312 comprises or is a component of a strain gauge. For example, a strain gauge embodiment may comprise a pressure sensitive element on or associated with an exposed surface of the transducer 312. In some embodiments, a metal strain gauge is adhered to the sensor surface, or a thin-film gauge may be applied on the sensor by sputtering or other technique. The measuring element or mechanism may comprise a diaphragm or metal foil. The transducer 312 may comprise any other type of sensor or pressure sensor, such as optical, potentiometric, resonant, thermal, ionization, or other types of strain or pressure sensors.

Figure 4:
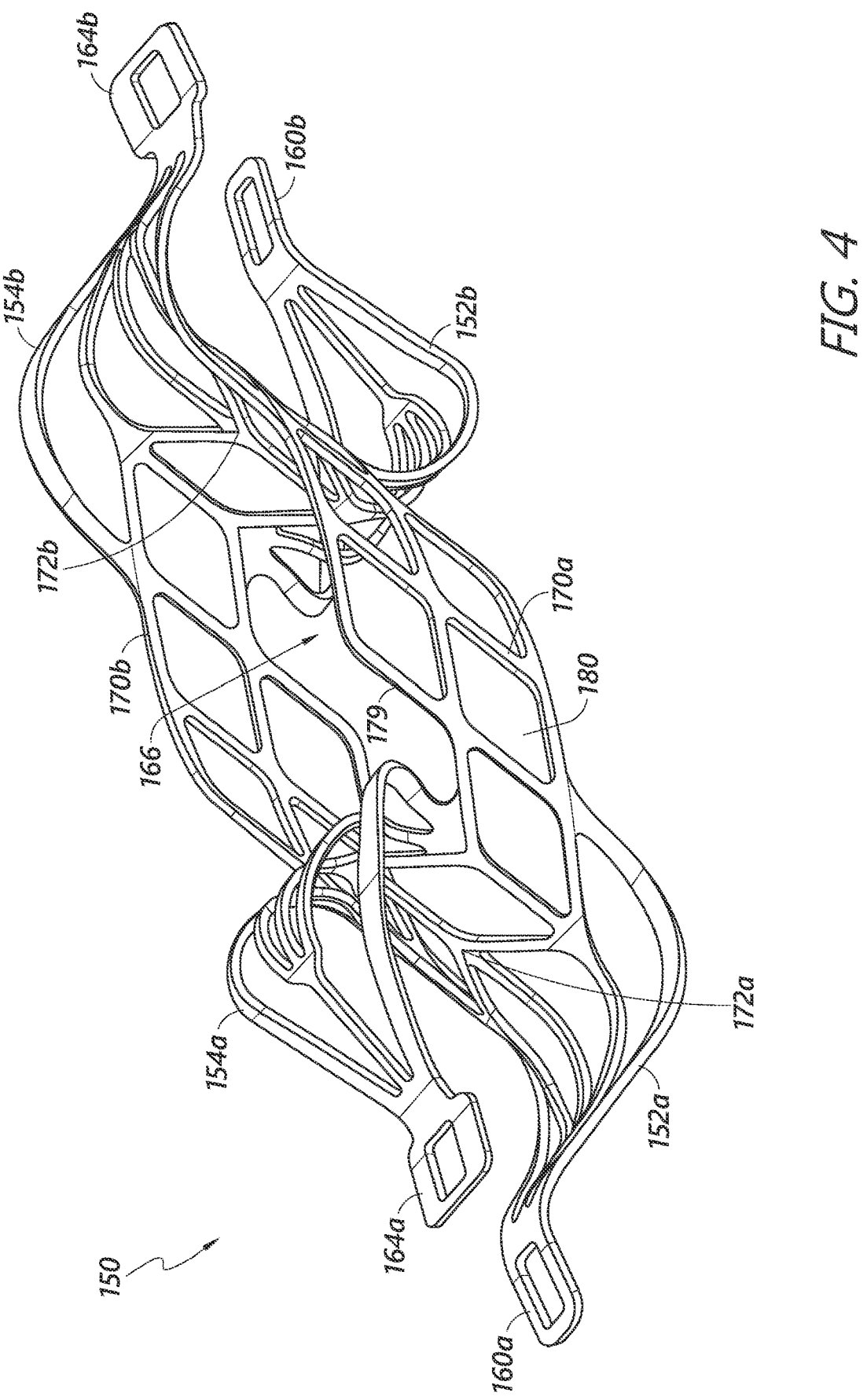
FIG. 4 illustrates an example shunt structure in accordance with one or more embodiments.

FIG. 4 illustrates an example shunt structure 150 in accordance with one or more embodiments. The shunt structure 150 may represent an embodiment of a cardiac implant device that may be integrated with pressure sensor functionality in accordance with certain embodiments disclosed herein. The shunt structure 150 may be an expandable shunt. When expanded, a central flow channel 166 of the shunt 150 may define a generally circular or oval opening. The channel 166 may be configured to hold the sides of a puncture opening in a tissue wall to form a blood flow path between chamber(s) or vessel(s) of the heart that are separated by the tissue wall. For example, the shunt 150 may be configured to be implanted in the wall separating the coronary sinus and the left atrium. The central flow channel 166 may be partly formed by a pair of side walls 170a, 170b defined by a generally parallelogram arrangement of thin struts 179 that forms an array of parallelogram-shaped cells or openings 180. In some embodiments, substantially the entire shunt 150 is formed by super-elastic struts that are configured to be compressed and fit into a catheter (not shown) and subsequently expanded back to the relaxed shape as shown in FIG. 4.

Formation of the shunt 150 using a plurality of interconnected struts forming cells therebetween may serve to at least partially increase the flexibility of the shunt, thereby enabling compression thereof and expansion at the implant site. The interconnected struts around the central flow channel 166 advantageously provide a cage having sufficient rigidity and structure to hold the tissue at the puncture in an open position. End walls 172a, 172b of the central flow channel 166 can serve to connect the side walls 170a, 170b and extend between distal and proximal flanges, or arms, 152, 154 on each side. The side walls 170a, 170b and end walls 172a, 172b together may define a tubular lattice, as shown. The end walls 172a, 172b can comprise thin struts 179 extending at a slight angle from a central flow axis of the shunt 150.

Although the illustrated shunt 150 comprises struts that define a tubular or circular lattice of open cells forming the central flow channel 166, in some embodiments, the structure that makes up the channel forms a substantially contiguous wall surface through at least a portion of the channel 166. In the illustrated embodiment, the tilt of the shunt structure 150 may facilitate collapse of the shunt into a delivery catheter (not shown), as well as the expansion of the flanges/arm 152, 154 on both sides of a target tissue wall. The central flow channel 166 may remain essentially unchanged between the collapsed and expanded states of the shunt 150, whereas the flanges/arms 152, 154 may transition in and out of alignment with the angled flow channel.

Although certain embodiments of shunts disclosed herein comprise flow channels having substantially circular cross-sections, in some embodiments, shunt structures in accordance with the present disclosure have oval-shaped, rectangular, diamond-shaped, or elliptical flow channel configuration. For example, relatively elongated side walls compared to the illustrated configuration of FIG. 4 may produce a rectangular or oval-shaped flow channel. Such shapes of shunt flow channels may be desirable for larger punctures, while still being configured to collapse down to a relatively small delivery profile.

In some embodiments, each of the distal and proximal flanges/arms 152, 154 is configured to curl outward from the end walls 172a, 172b and be set to point approximately radially away from the central flow channel 166 in the expanded configuration. The expanded flanges/arms may serve to secure the shunt 150 to a target tissue wall. Additional aspects and features of shunt structures that may be integrated with sensor devices/functionality in accordance with embodiments of the present disclosure are disclosed in U.S. Pat. No. 9,789,294, entitled "Expandable Cardiac Shunt." issued on Oct. 17, 2017, the disclosure of which is hereby expressly incorporated by reference in its entirety. Although certain embodiments are disclosed herein in the context of shunt structures similar to that shown in FIG. 4 and described above, it should be understood that shunt structures or other implant devices integrated with pressure sensor functionality in accordance with embodiments the present disclosure may have any type, form, structure, configuration, and/or may be used or configured to be used for any purpose, whether for shunting or other purpose or functionality.

Figure 5:
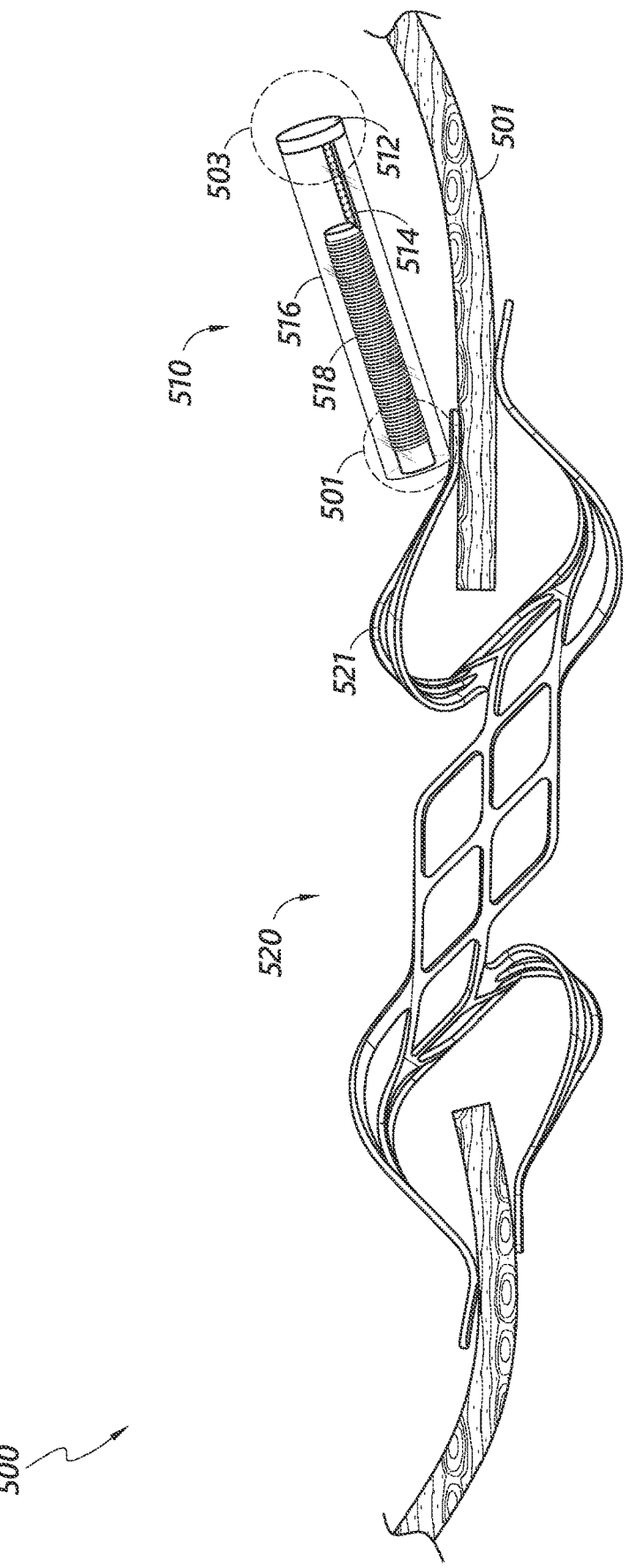
FIG. 5 illustrates a sensor implant device comprising a shunt structure and an integrated sensor in accordance with one or more embodiments.

Sensor devices in accordance with embodiments the present disclosure may be integrated with cardiac shunt structures/devices or other implant devices using any suitable or desirable attachment or integration mechanism or configuration. FIG. 5 illustrates a sensor implant device 500 comprising a shunt structure 520 and an integrated sensor 510 in accordance with one or more embodiments. In some embodiments, the sensor 510 may be built or manufactured into the shunt structure 520 to form a unitary structure. In some embodiments, the sensor 510 may be attached to or integrated with an arm member 521 of the shunt structure 520.

The sensor 510 includes a sensor element 512, such as a pressure sensor transducer. Relative to the arm member 521 of the shunt structure 520, the transducer element 512 (e.g., pressure transducer) may be oriented/positioned at a distal 503 or proximal 501 end or area of the sensor 510. For example, the illustrated embodiment of FIG. 5 includes the transducer 512 disposed at the distal end 503 of the sensor 510. In some embodiments, readings acquired by the sensor may be used to guide titration of medication for treatment of a patient in whom the implant device 520 is implanted.

As described herein, the sensor 510 may be configured to implement wireless data and/or power transmission. The sensor 510 may include an antenna component 518 and control circuitry 514 configured to facilitate wireless data and/or power communication functionality. In some embodiments, the antenna 518 comprises one or more conductive coils, which may facilitate inductive powering and/or data transmission.

The sensor 510 may advantageously be biocompatible. For example, the sensor 510 may comprise a biocompatible housing 516, such as a cylindrical or other-shaped housing comprising glass or other biocompatible material. The circuitry 514, sensor element 512, and/or antenna 518 may be at least partially contained within the housing 516, wherein the housing 516 is sealed to prevent exposure to such components to the external environment. However, at least a portion of the sensor element 512, such as a diaphragm or other component, may be exposed to the external environment in some embodiments in order to allow for pressure readings, or other parameter sensing, to be implemented. The housing 516 may comprise an at least partially rigid cylindrical or tube-like form, such as a glass cylinder form, wherein the sensing probe 512 is disposed at one or both ends 501, 503 of the sensor assembly 510. In some embodiments, the sensor assembly is approximately 3 mm or less in diameter and/or approximately 20 mm or less in length. The sensor element 512 may comprise a pressure transducer, as described herein.

The sensor assembly 510 may be configured to communicate with an external system when implanted in a heart or other area of a patient's body. For example, the sensor 510 may receive power wirelessly from the external system and/or communicate sensed data or waveforms to and/or from the external system. The sensor assembly 510 may be attached to, or integrated with, the shunt structure 520 in any suitable or desirable way. For example, in some implementations, the sensor 510 may be attached or integrated with the shunt structure 520 using mechanical attachment means. In some embodiments, as described in detail below, the sensor assembly 510 may be contained in a pouch or other receptacle that is attached to the shunt structure 520.

The sensor element 512 may comprise a pressure transducer. For example, the pressure transducer may be a microelectromechanical system (MEMS) transducer comprising a semiconductor diaphragm component. In some embodiments, the transducer may include an at least partially flexible or compressible diaphragm component, which may be made from silicone or other flexible material. The diaphragm component may be configured to be flexed or compressed in response to changes in environmental pressure. The control circuitry 514 may be configured to process signals generated in response to said flexing/compression to provide pressure readings. In some embodiments, the diaphragm component is associated with a biocompatible layer on the outside surface thereof, such as silicon nitride (e.g., doped silicon nitride) or the like. The diaphragm component and/or other components of the pressure transducer 512 may advantageously be fused or otherwise sealed to/with the housing 516 in order to provide hermetic sealing of at least some of the sensor assembly components.

The control circuitry 514 may comprise one or more electronic application-specific integrated circuit (ASIC) chips or die, which may be programmed and/or customized or configured to perform monitoring functionality as described herein and/or facilitate transmission of sensor signals wirelessly. The antenna 518 may comprise a ferrite core wrapped with conductive material in the form of a plurality of coils (e.g., wire coil). In some embodiments, the coils comprise copper or other metal. The antenna 518 may advantageously be configured with coil geometry that does not result in substantial displacement or heating in the presence of magnetic resonance imaging. In some implementations, the sensor implant device 500 may be delivered to a target implant site using a delivery catheter (not shown), wherein the delivery catheter includes a cavity or channel configured to accommodate the advancement of the sensor assembly 510 therethrough.

Figure 6:
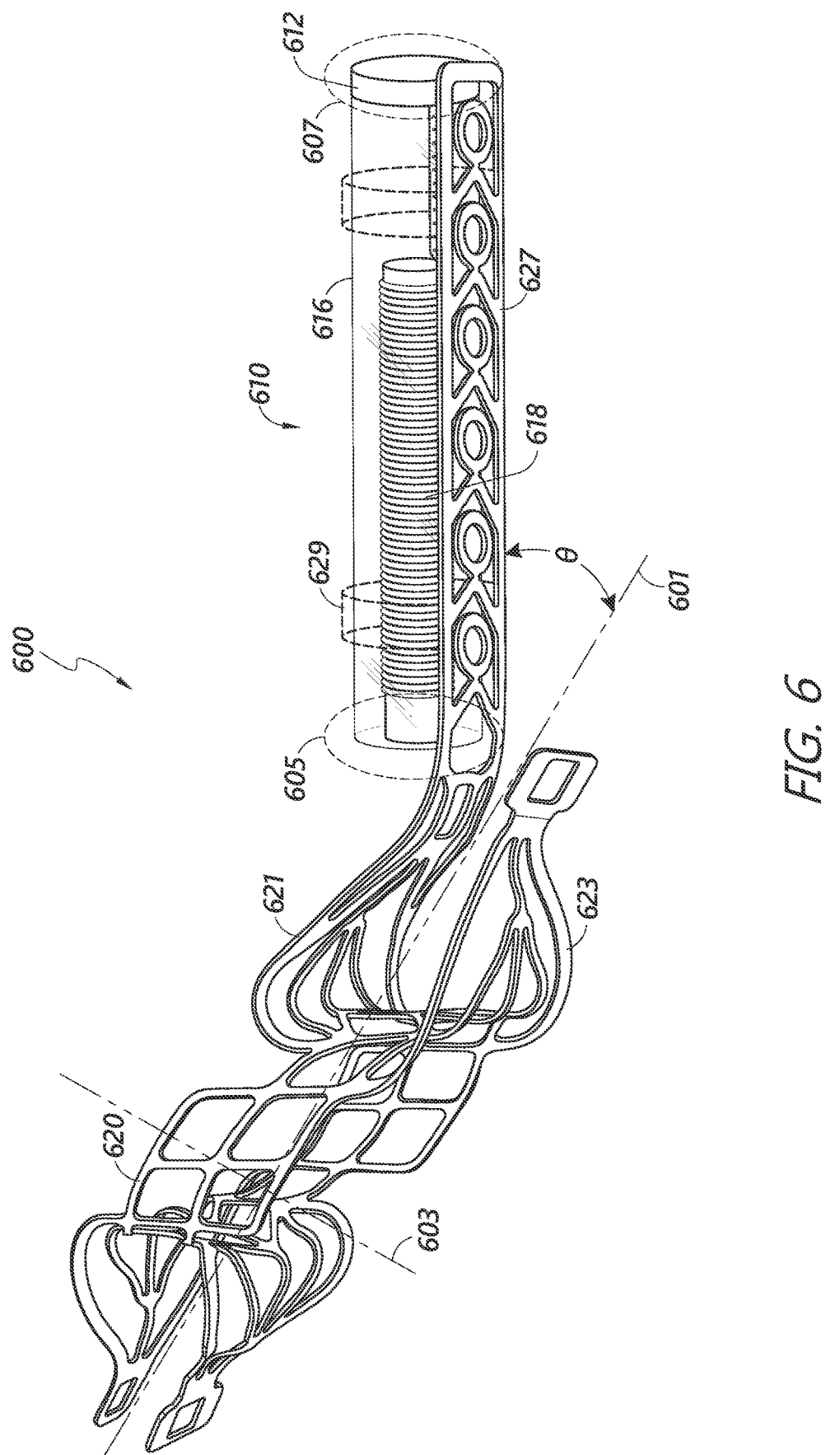
FIG. 6 illustrates a sensor implant device having an integrated sensor in accordance with one or more embodiments.

FIG. 6 illustrates a sensor implant device 600 having an integrated sensor 610 that is mechanically attached or fastened to a portion of a shunt structure 620. The shunt structure 620 comprises a sensor support 627, which may be a unitary form with this shunt structure 620. In some embodiments, the support 627 is an extension of, or otherwise associated with, an arm member 621 of the shunt structure 620. The sensor 610 may be attached to the support 627 by any suitable or desirable attachment means, including adhesive attachment, or mechanical engagement. For example, the sensor support 627 may comprise or be associated with one or more retention features 629, which may comprise one or more clamps, straps, ties, sutures, collars, clips, tabs, or the like. Such retention features 629 may circumferentially encase or retain the sensor 610, or a portion thereof. In some embodiments, the sensor 610 may be attached to the sensor support 627 through the application of mechanical force, either through sliding the sensor 610 through the retention features 629 or through clipping, locking, or otherwise engaging the sensor 610 with the sensor support 627 by pressing or applying other mechanical force thereto. In some embodiments, the retention features 629 comprise one or more tabs that may be configured to pop-up or extend on one or more sides of the sensor support 627 for mechanical fastening. Such tabs may comprise memory metal (e.g., Nitinol) or other at least partially rigid material. In some embodiments, the sensor support 627 is at least partially non-rigid. For example, the sensor support 627 may comprise a non-rigid tether configured to float the sensor 610. Such configurations may advantageously allow for the sensor 610 to move with the blood flow.

In some embodiments, the sensor 610 is pre-attached to the sensor support 627 and/or integrated therewith prior to implantation. For example, in some embodiments, the sensor support 627 forms at least a portion of the housing of the sensor 610, such that the sensor support 627 and at least a portion of the housing of the sensor 610 are a unitary form.

In some embodiments, the angle or position of the sensor support 627 and/or sensor 610 relative to a longitudinal axis 601 of the shunt structure 620 is such that the sensor projects away from the longitudinal axis 601. For example, where the shunt structure 620 is engaged with biological tissue along the dimension of the longitudinal axis 601, the sensor 610 may advantageously project at least partially away from the biological tissue, such as into a chamber cavity (e.g., atrium of a heart). In some embodiments, the sensor support 627 is configured, or can be configured, substantially at a right angle or 90° orientation with respect to the axis 601, such that the sensor is substantially orthogonal to the longitudinal axis of the shunt. Such configurations may advantageously allow for the sensor element to be positioned a desirable distance away from the shunted flow flowing through the flow path axis 603.

The sensor element 612 of the sensor 610 may be disposed or positioned at any location of the sensor 610. For example, the sensor element 612 may advantageously be disposed at or near a distal portion 607 of the sensor 610. Alternatively or additionally, a sensor element may be disposed or positioned at or near a proximal portion 605 of the sensor 610.

FIG. 7 illustrates a sensor implant device 700 having an integrated sensor 710 that is attached to a portion of a shunt structure 720 in accordance with one or more embodiments. The sensor 710 is attached to, or held within, a pouch 727 that is attached to or otherwise associated with an arm/flange member 721 or another portion of a shunt structure 720. For example, the pouch 727 may be a suture-based or cloth-based pouch, wrapping, or other retention form. In some embodiments, the sensor 710 is configured to be slidingly disposed within the pouch 727, wherein tension and/or compression of the pouch 727 serves to retain the sensor 710 in a fixed position within the pouch 727. Although a pouch is illustrated in FIG. 7 that envelops at least a portion of the sensor 710 in a sock-like manner, in some embodiments, the pouch 727 comprises a band or other non-enveloping retention means. In some embodiments, the sensor 710 may be sutured or otherwise attached or fixed to the pouch 727. Furthermore, the pouch 727 may be sutured or otherwise fixed or attached to the arm member 721 of the shunt structure 720.

In some implementations, embodiments of the present disclosure provide for a sensor attached to a flexible netting that is connected to at least a portion of a shunt structure such that the netting at least partially covers, or lies in, the flow path when deployed and allows flow through openings in the netting. Such embodiments may advantageously allow for deployment in accordance with FIGS. 8A-8D.

Figure 8A:
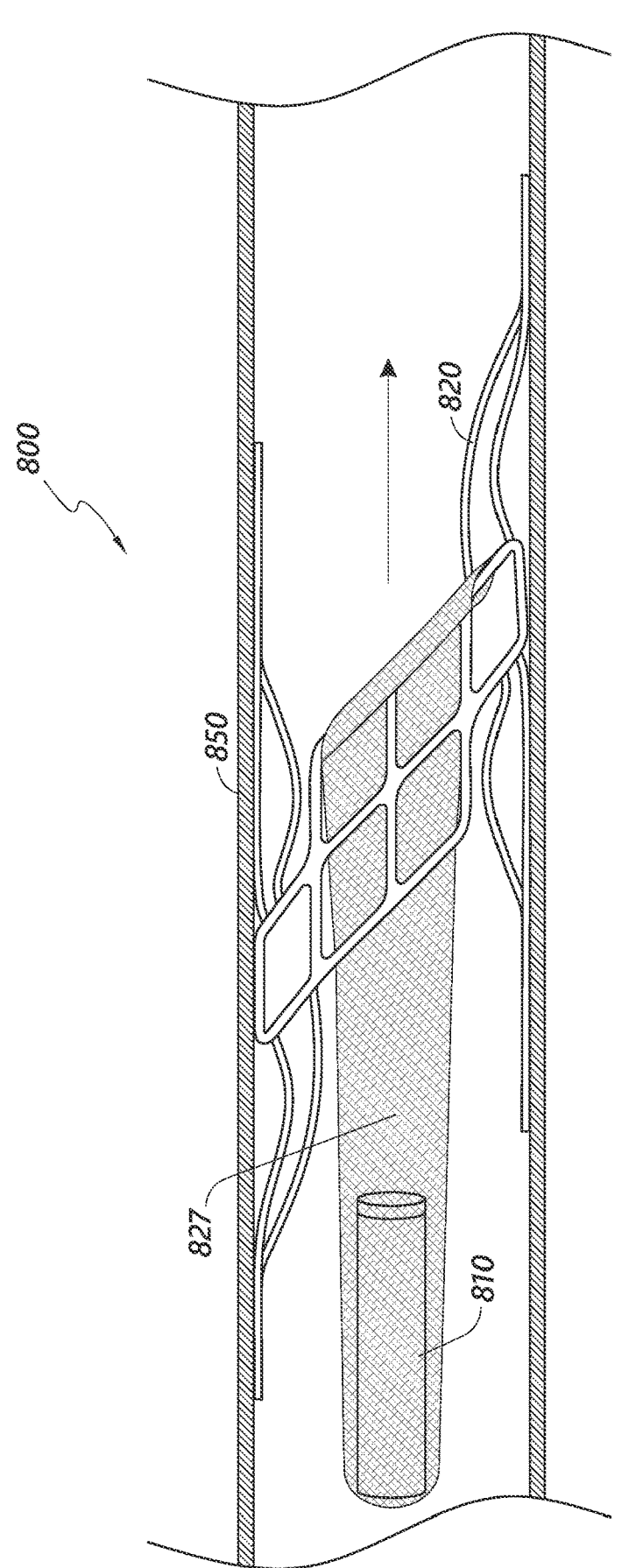
FIGS. 8A-8D illustrate stages of processes for implanting a sensor implant device in accordance with one or more embodiments.

FIG. 8A shows a sensor implant device 800 in a delivery configuration within a delivery catheter 850. In the illustrated delivery configuration, FIG. 8A shows a shunt structure 820 of the sensor implant device 800 in a collapsed/delivery configuration within the catheter 850, wherein the shunt structure 820 is attached to a netting 827 that is in turn attached to or otherwise associated with a sensor 810. The sensor implant device 800 may be deployed within/from the catheter 850 and the direction shown, wherein the shunt structure 820 leads the sensor 810, which is pulled behind the shunt structure 820 by the tethered netting 827. The netting 827 may comprise braided memory metal (e.g., Nitinol), or other type of braid or mesh that is at least partially flexible. The netting advantageously has openings therein sufficiently large and configured to allow for the flow of fluid therethrough with relatively little or no obstruction or alteration of fluid flow through the flow path of the shunt structure 820.

Figure 8B:
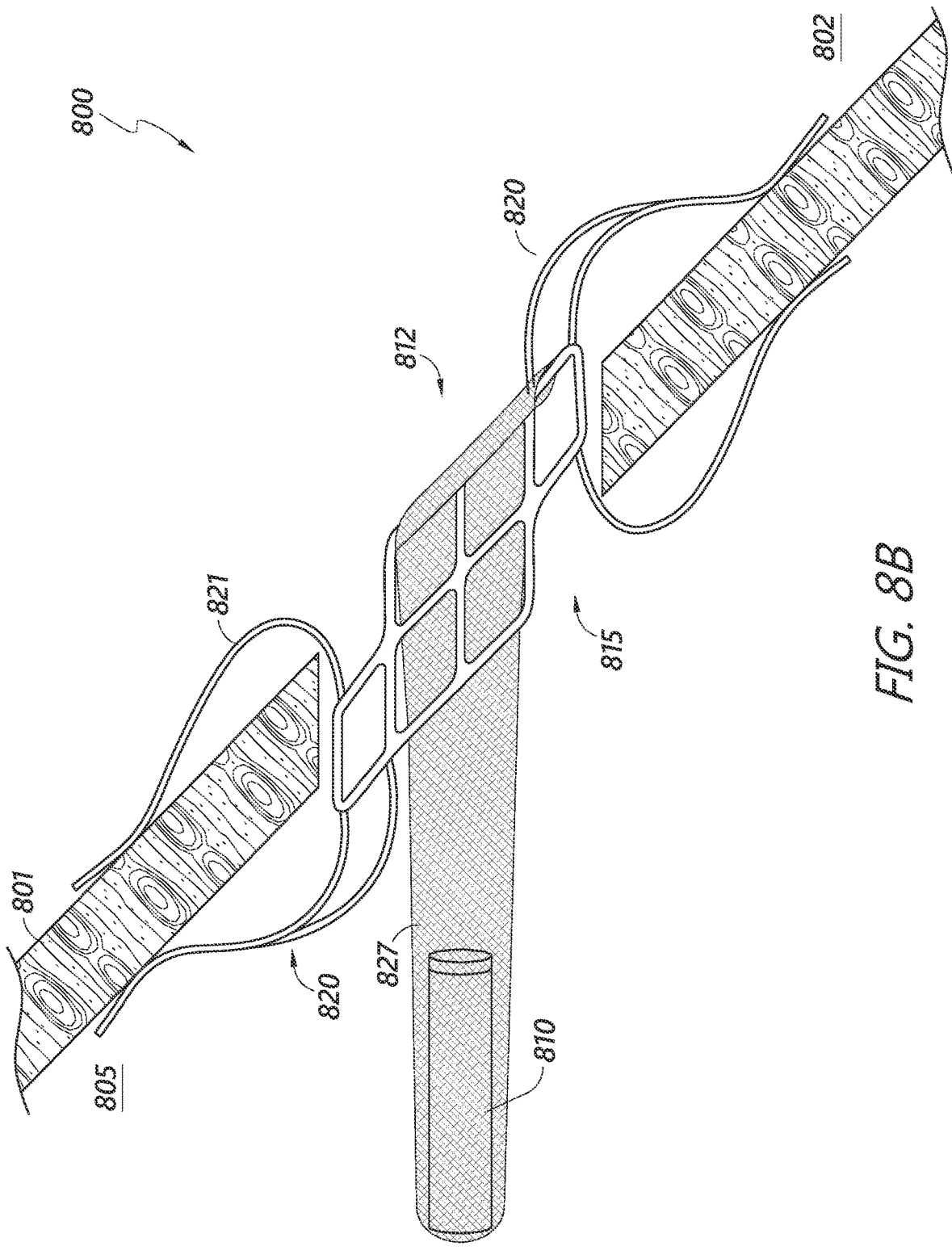

FIG. 8B shows the shunt structure 820 in a deployed configuration and coupled to a biological tissue wall 801 via one or more arm members 821, as described herein. In the state of FIG. 8B, the sensor 810 has not yet been fully deployed, and trails the shunt structure 820 and is tethered thereto by the netting 827. For example, in the state shown in FIG. 8B, the sensor 810 may be positioned on a proximal side 805 of the tissue wall 801, wherein it is desirable for the sensor to be deployed in a chamber or area associated with the distal side 802 of the tissue wall 801 when implanted. The netting 827 may be attached to the shunt structure 820 at a distal side 812 of the shunt structure, such as at a circumferential portion of a flow path channel defined by the shunt structure. Additionally or alternatively, the netting 827 may be coupled to the shunt structure 820 at or near a circumferential portion of a proximal side 815 of the shunt structure 820. In some embodiments, the netting 827 may be coupled to one or more arm members of the shunt structure 820. In the partially deployed state shown in FIG. 8B, the sensor 810 may be positioned in the coronary sinus, which may correspond to the proximal side 805 of the tissue wall 801, whereas the distal side 802 of the tissue wall may correspond to the left atrium.

Figure 8C:
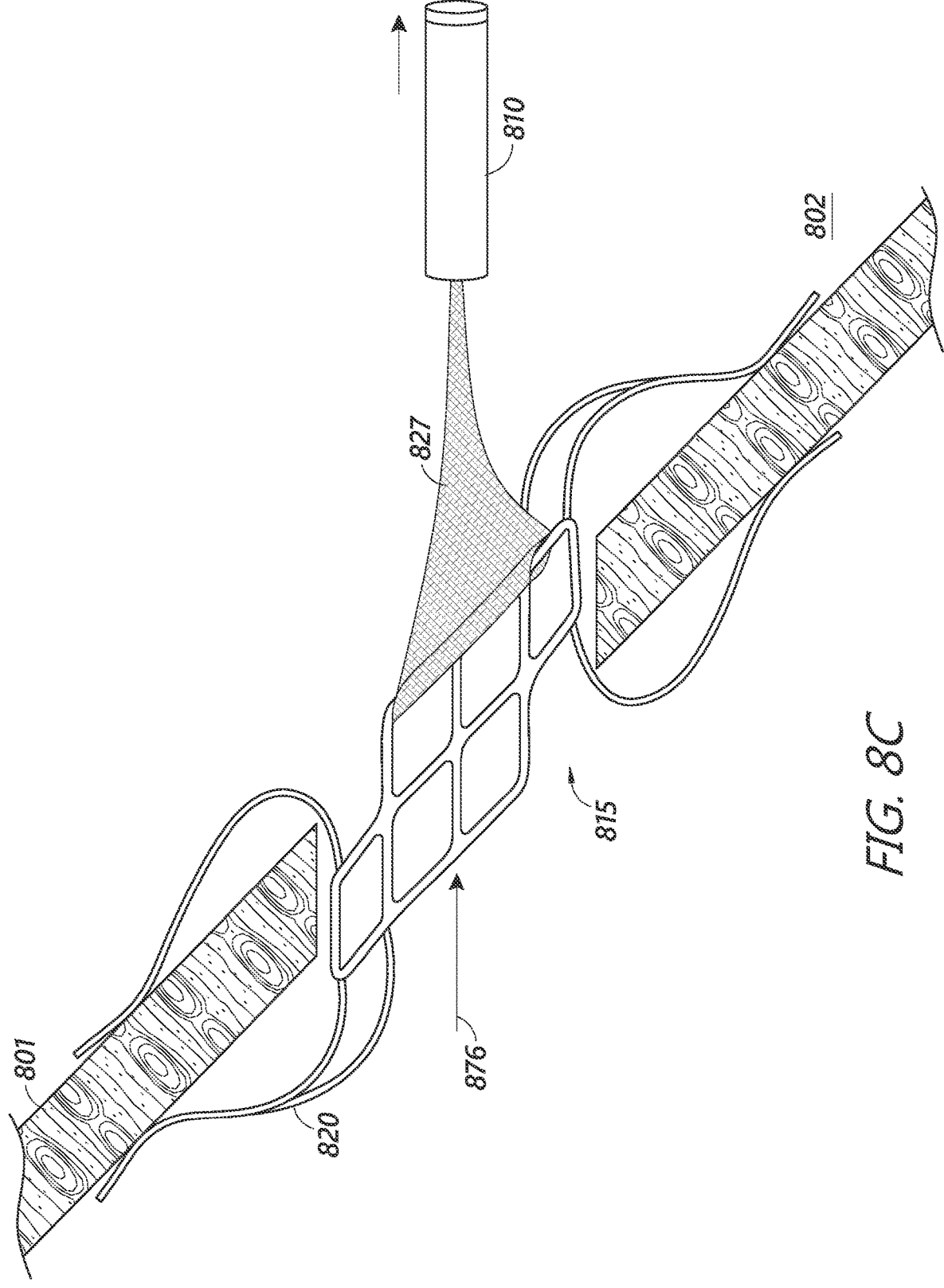

FIG. 8C shows the sensor 810 fully deployed on the distal side 802 of the tissue wall 801, which may be achieved by passing the sensor 810 through the flow path 876 of the shunt structure 820 and thereby introducing the sensor 810 into the chamber or area associated with the distal side 802 of the tissue wall 801, wherein the sensor 810 is at least partially captured by, or attached to, the netting, which tethers the sensor 810 to the shunt structure 820. As the sensor 810 is passed through the flow path 876 of the shunt structure 820, the netting 827 may become at least partially inverted and/or folded, such that the sensor 810 exposed in the target area 802, as shown, whereas in the pre-deployed configuration shown in FIGS. 8A and 8B, the sensor was held within the netting 827. Alternatively, the sensor 810 may be captured or held within the netting 827 when in the deployed configuration shown in FIG. 8C and attached outside the netting 827 in the pre-deployed configuration. That is, although FIG. 8A shows the sensor 810 contained within that netting 827 in the pre-deployed configuration, and FIG. 8C shows the sensor outside of the netting in the deployed configuration, in some embodiments, the sensor is initially attached outside the netting 827 in the pre-deployed configuration of FIG. 8A, whereas when the netting becomes inverted as the sensor passes through the flow path 876 in FIG. 8C, the sensor may be drawn into the netting, such that it is substantially enclosed therein. The sensor 810 may be attached or fixed to the netting 827 using any suitable or desirable attachment means or mechanism. By inverting the netting 827, as shown in FIG. 8C, the sensor 810 may be projected into the left atrium, or other chamber.

Figure 8D:
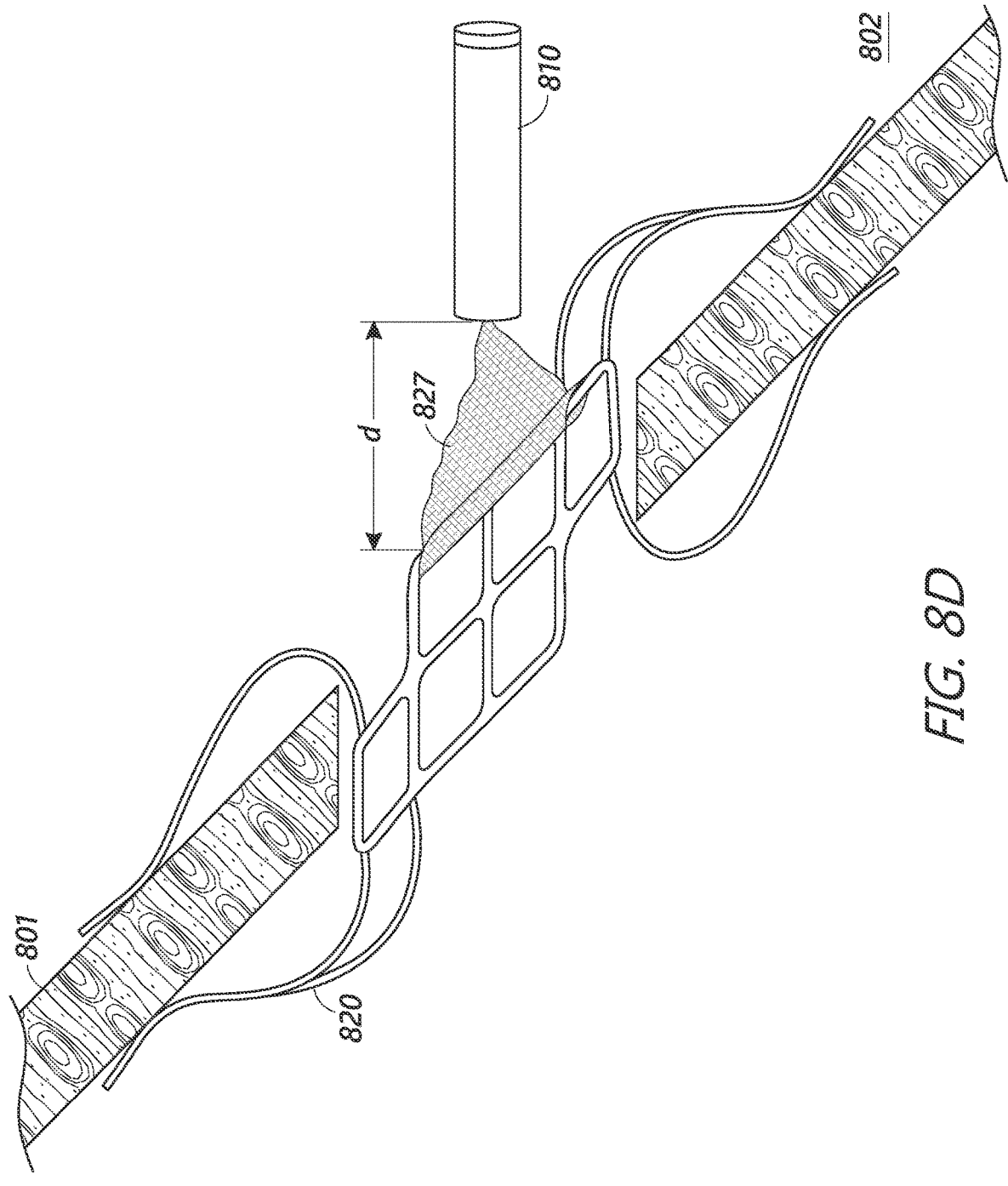

FIG. 8D shows the deployed sensor implant device 800 and a retracted state, wherein the netting 827 has been cinched or retracted to some degree in order to reduce the distance 'd' and/or position of the sensor 810 relative to the shunt structure 820. For example, as referenced above, the netting 827 may comprise memory metal, or other material that may be manipulated or formed to a suitable or desirable form in response to a certain stimulus or force, such as the cinched form of FIG. 8D. The netting 827 may advantageously comprise weaved or braided memory metal (e.g., Nitinol) that has flexibility and/or elasticity characteristics that allow for the sensor to pull the netting at least partially through the flow path 876 of the shunt structure 820. In some embodiments, the netting 827 comprises re-flowed Carbothane, or polyurethane. In some embodiments, the netting is laser bonded. In some embodiments, the netting comprises holes sufficiently large to reduce the risk of clogging.

Sensor-integrated shunt implant devices in accordance with embodiments of the present disclosure may be implanted in any suitable or desirable tissue wall. For example, in some implementations, a sensor-integrated shunt device in accordance with embodiments of the present disclosure is implanted in the interatrial septal wall. Although certain embodiments are disclosed herein in the context of interatrial shunt implants incorporating pressure sensor functionality, it should be understood that embodiments of the present disclosure may comprise any type of cardiac shunt or implant device implanted in any location of the heart or body and incorporating any type of telemetric monitoring functionality.

Figure 9:
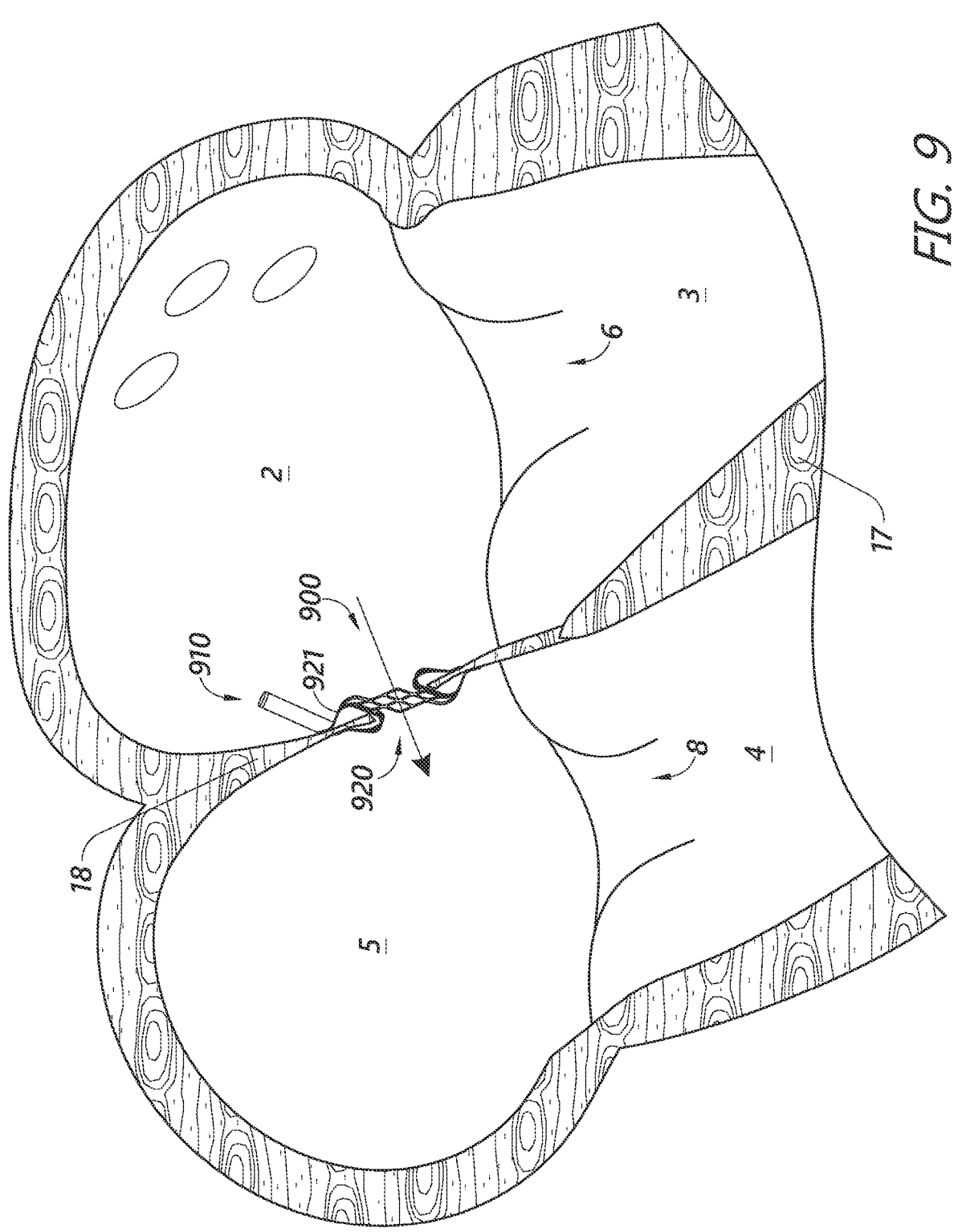
FIG. 9 shows a sensor implant device implanted in an atrial septum in accordance with one or more embodiments.

FIG. 9 shows a sensor implant device 900 implanted in an atrial septum 18 in accordance with one or more embodiments. The particular position in the interatrial septum wall may be selected or determined in order to provide a relatively secure anchor location for the shunt structure 920, as well as to provide a relatively low risk of thrombus. Furthermore, the sensor implant device 900 may be implanted at a position that is desirable in consideration of future re-crossing of the septal wall for future interventions. Implantation of the sensor implant device 900 in the interatrial septum wall may advantageously allow for communication between the left 2 and right 5 atria. With the device 900 in the atrial septum 18, the sensor 910 of the sensor implant device 900 may advantageously be configured to measure pressure in the right atrium 5, the left atrium 2, or both atria. For example, in some embodiments, the device 900 comprises a plurality of sensors, wherein one sensor is disposed in each of the right atrium 5 and the left atrium 2. With pressure sensor functionality for measuring pressure in both atria, the sensor implant device 900 may advantageously be configured to provide sensor signals that may be used to determine differential pressure between the atria. Differential pressure determination may be useful for monitoring fluid build-up in the lungs, which may be associated with congestive heart failure.

Interatrial shunting using the sensor implant device 900, which integrates pressure monitoring functionality, may advantageously be well-suited for patients that are relatively highly sensitive to atrial pressure increases. For example, as pressure increases in the ventricles and/or atria and is applied against the myocardial cells, the muscles of the heart may generally be prone to contract relatively harder according to process the excess blood. Therefore, as the ventricle dilates or stretches, for patients with compromised contractility of the ventricle, such patients may become more sensitive to higher pressures in the ventricle and/or atria because the heart may be unable to adequately respond or react thereto. Furthermore, increases in left atrial pressure can results in dyspnea, and therefore reduction in left atrial pressure to reduce dyspnea and/or reduce incidences of hospital readmission may be desirable through interatrial shunting. For example, when the ventricle experiences dysfunction such that is unable to accommodate build-up in fluid pressure, such fluid may backup into the atria, thereby increasing atrial pressure. With respect to heart failure, minimization of left ventricular end-diastolic pressure may be paramount. Because left ventricular end-diastolic pressure can be related to left atrial pressure, backup of fluid in the atrium can cause backup of fluid in the lungs, thereby causing undesirable and/or dangerous fluid buildup in the lungs. Interatrial shunting, such as using shunt devices in accordance with embodiments of the present disclosure, can divert extra fluid in the left atrium to the right atrium, which may be able to accommodate the additional fluid due to the relatively high compliance in the right atrium.

In some situations, interatrial shunting may not be sufficiently effective due to the patient being subject to a drug regimen designed to control the patient's fluid output and/or pressure. For example, diuretic medications may be used to cause the patient to expel excess fluid. Therefore, use of pressure-sensor-integrated implants in accordance with embodiments the present disclosure may provide a mechanism to inform technicians or doctors/surgeons with respect to how to titrate such medications to adjust/modify fluid status. Therefore, embodiments the present disclosure may advantageously serve to direct medication intervention to reduce or prevent & the undesirable increase in left atrial pressure.

Figure 10:
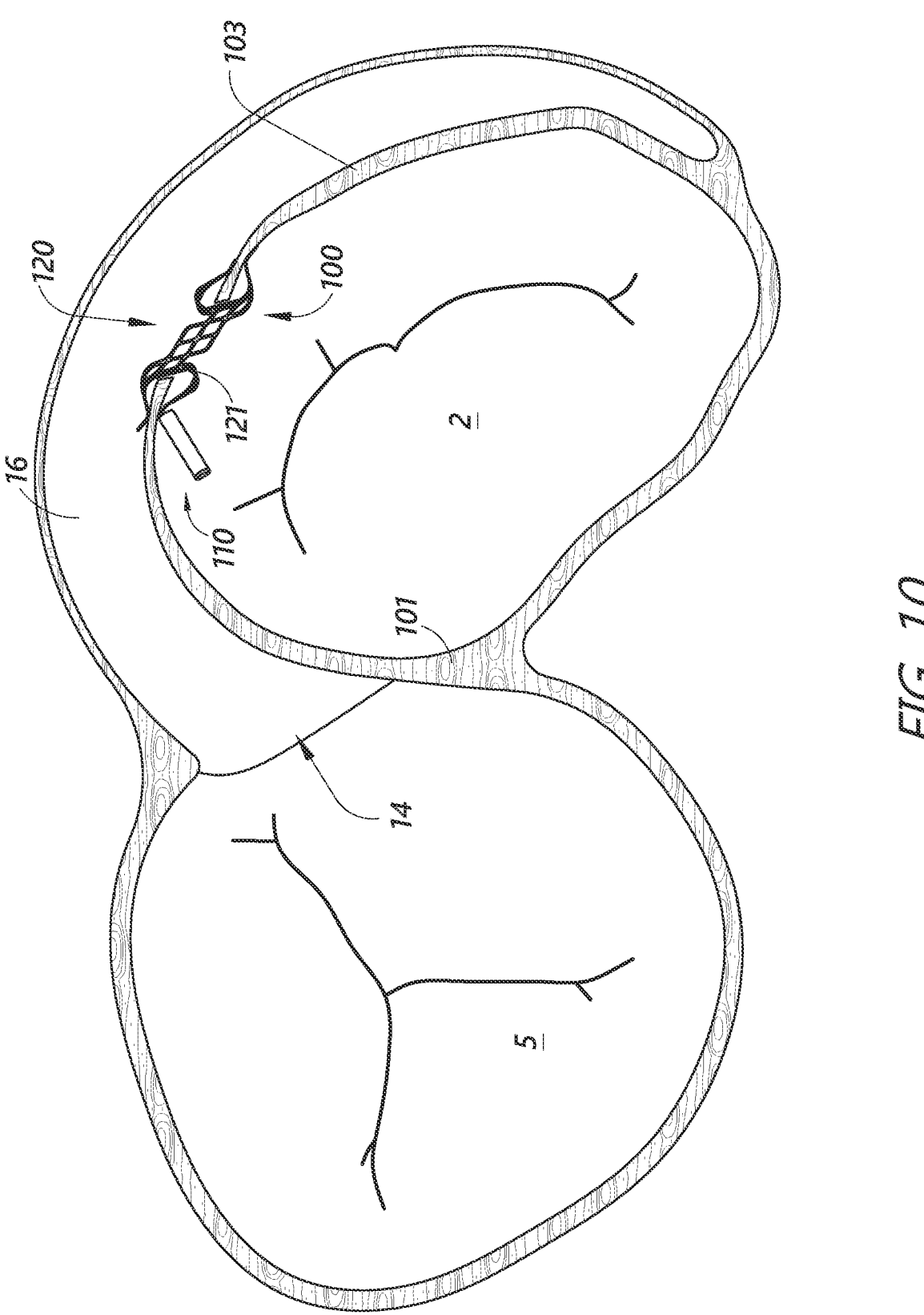
FIG. 10 shows a sensor implant device implanted in a tissue wall between the coronary sinus and the left atrium in accordance with one or more embodiments.

In some implementations, sensor-integrated shunt implant devices in accordance with embodiments of the present disclosure may be implanted in the wall separating the coronary sinus from the left atrium. For example, interatrial shunting may be achieved through the coronary sinus. FIG. 10 shows a sensor implant device 100 implanted in a tissue wall 103 between the coronary sinus 16 and the left atrium 2. FIG. 10, as well as a number of the following figures, shows a section of the heart from a top-down perspective with the posterior aspect oriented at the top of the page.

Interatrial shunting through implantation of the shunt device 100 in the wall 103 between the left atrium 2 and the coronary sinus 16 can be preferable to shunting through the interatrial septum 101 in some situations. For example, shunting through the coronary sinus 16 can provide reduced risk of thrombus and embolism. The coronary sinus is less likely to have thrombus/emboli present for several reasons. First, the blood draining from the coronary vasculature into the right atrium has just passed through capillaries, so it is essentially filtered blood. Second, the ostium of the coronary sinus in the right atrium is often partially covered by a pseudo-valve called the Thebesian Valve. The Thebesian Valve is not always present, but some studies show it is present in most hearts and can block thrombus or other emboli from entering in the event of a spike in right atrium pressure. Third, the pressure gradient between the coronary sinus and the right atrium into which it drains is generally relatively low, such that thrombus or other emboli in the right atrium is likely to remain there. Fourth, in the event that thrombus/emboli do enter the coronary sinus, there will be a much greater gradient between the right atrium and the coronary vasculature than between the right atrium and the left atrium. Most likely, thrombus/emboli would travel further down the coronary vasculature until right atrium pressure returned to normal and then the emboli would return directly to the right atrium.

Some additional advantages to locating the shunt structure 120 between the left atrium and the coronary sinus is that this anatomy is generally more stable than the interatrial septal tissue. By diverting left atrial blood into the coronary sinus, sinus pressures may increase by a small amount. This would cause blood in the coronary vasculature to travel more slowly through the heart, increasing perfusion and oxygen transfer, which would be more efficient and also could help a dying heart muscle to recover.

In addition to the above-mentioned benefits, by implanting the shunt device 100 in the wall of the coronary sinus 103, damage to the interatrial septum 101 may be prevented. Therefore, the interatrial septum may be preserved for later transseptal access for alternate therapies. The preservation of transseptal access may be advantageous for various reasons. For example, heart failure patients often have a number of other comorbidities, such as atrial fibrillation and/or mitral regurgitation; certain therapies for treating these conditions require a transseptal access.

It should be noted, that in addition to the various benefits of placing the implant 100 between the coronary sinus 16 and the left atrium 2, certain drawbacks may be considered. For example, by shunting blood from the left atrium 2 to the coronary sinus 16, oxygenated blood from the left atrium 2 may be passed to the right atrium 5 and/or non-oxygenated blood from the right atrium 5 may be passed to the left atrium 2, both of which may be undesirable with respect to proper functioning of the heart.

Access to the target wall 103 and left atrium 2 via the coronary sinus 16 may be achieved using any suitable or desirable procedure. For example, various access pathways may be utilized in maneuvering guidewires and catheters in and around the heart to deploy an expandable shunt integrated or associated with a pressure sensor in accordance with embodiments of the present disclosure. In some embodiments, access may be achieved through the subclavian or jugular veins into the superior vena cava (not shown), right atrium 5 and from there into the coronary sinus 16. Alternatively, the access path may start in the femoral vein and through the inferior vena cava (not shown) into the heart. Other access routes may also be used, each of which may typically utilize a percutaneous incision through which the guidewire and catheter are inserted into the vasculature, normally through a sealed introducer, and from there the system may be designed or configured to allow the physician to control the distal ends of the devices from outside the body.

In some embodiments of procedures for advancing implant devices in accordance with aspects of the present disclosure, a guidewire is introduced through the subclavian or jugular vein, through the superior vena cava and into the coronary sinus. Once the guidewire provides a path, an introducer sheath may be routed along the guidewire and into the patient's vasculature, typically with the use of a dilator. The delivery catheter may be advanced through the superior vena cava to the coronary sinus of the heart, wherein the introducer sheath may provide a hemostatic valve to prevent blood loss. In some embodiments, a deployment catheter may function to form and prepare an opening in the wall of the left atrium, and a separate placement or delivery catheter will be used for delivery of an expandable shunt. In other embodiments, the deployment catheter may be used as the both the puncture preparation and implant delivery catheter with full functionality. In the present application, the terms "deployment catheter" or "delivery catheter" are used to represent a catheter or introducer with one or both of these functions.

As illustrated in FIG. 10, the coronary sinus is generally contiguous around the left atrium 2, and therefore there are a variety of possible acceptable placements for the implant device 100 and/or shunt structure 120. The target site selected for placement of the shunt structure 120, may be made in an area where the tissue of the particular patient is less thick or less dense, as determined beforehand by non-invasive diagnostic means, such as a CT scan or radiographic technique, such as fluoroscopy or intravascular coronary echo (IVUS).

Additional aspects and features of processes for delivering shunt structures that may be integrated with sensor devices/functionality in accordance with embodiments of the present disclosure for implantation in the wall between the coronary sinus and the left atrium are disclosed in U.S. Pat. No. 9,789,294, entitled "Expandable Cardiac Shunt," issued on Oct. 17, 2017, the disclosure of which is hereby expressly incorporated by reference in its entirety. Although the implant device 100 is shown in the left atrium/coronary sinus wall, the implant device 100 may be positioned between other cardiac chambers, such as between the pulmonary artery and right atrium.

Figure 11:
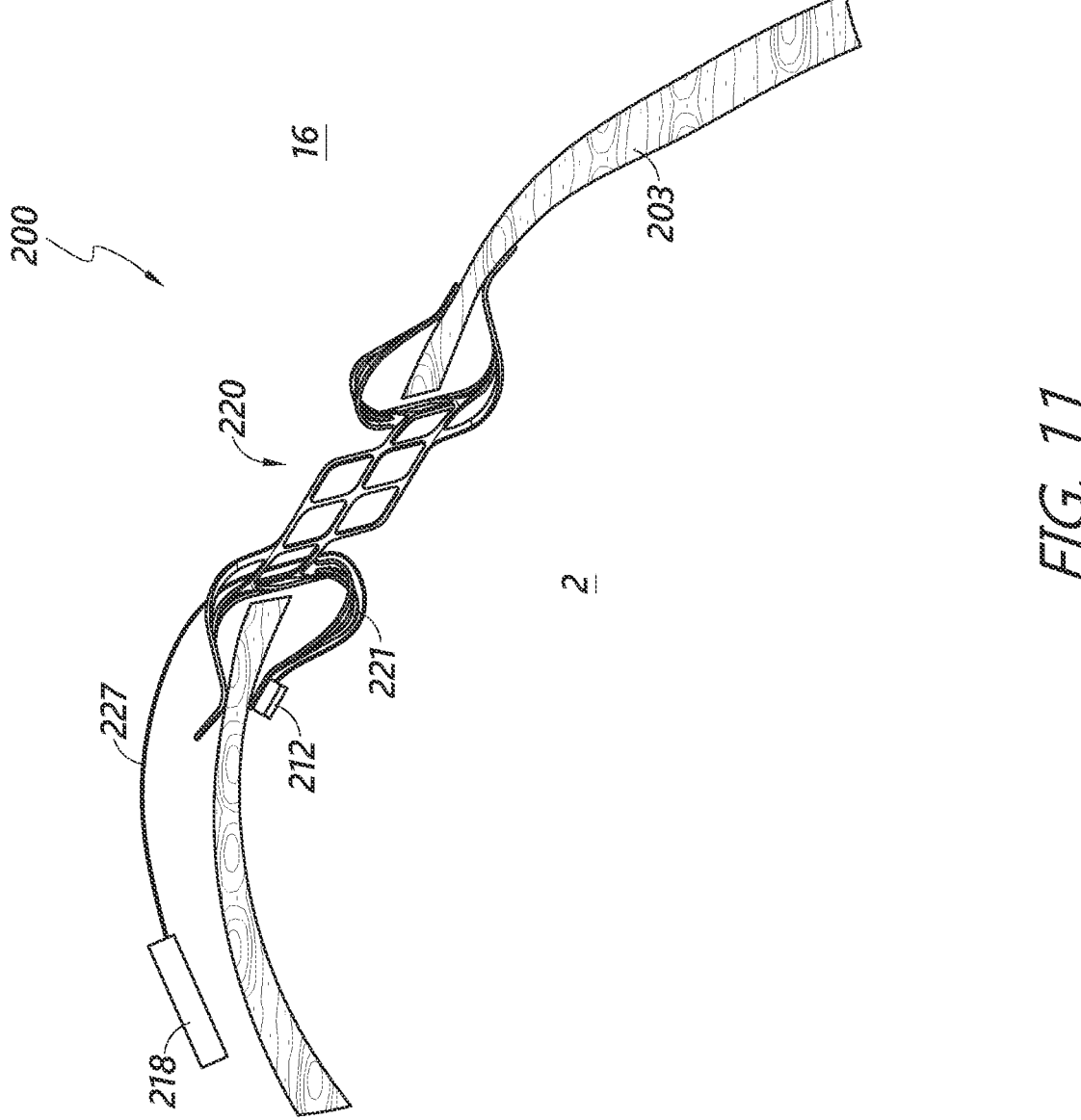
FIG. 11 illustrates a sensor implant device comprising a tethered antenna in accordance with one or more embodiments.

Sensor components of sensor-functionality-integrated shunt implant devices in accordance with embodiments of the present disclosure may have any suitable or desirable configuration. For example, sensors in accordance with embodiments of the present disclosure may comprise an antenna that is tethered in some manner to sensor circuitry and/or shunt or implant structure. For sensor implant devices comprising shunt structure as well as sensor components, in some embodiments, the profile of the sensor implant device may be undesirably large, such that delivery of the device to the target location through transcatheter access may be difficult or untenable. Some embodiments of the present disclosure relate to the sensor implant devices comprising sensor assemblies that have separate components separated by a coupling tether or the like, wherein such devices may assume a relatively smaller profile in a pre-deployed configuration within the delivery catheter. FIG. 11 illustrates a sensor implant device 200 comprising a tethered antenna 218, which may advantageously have relatively small profile for transcatheter delivery. The antenna 218 is advantageously electrically coupled to a senor element 212, such as a pressure transducer and/or associated control circuitry.

The sensor element 212, which may comprise one or more of the transducer and/or control circuitry (e.g., application-specific integrated circuit) of the sensor may be attached or otherwise integrated onto an arm 221 of the shunt structure 220. For example, the sensing element 212 may be attached to shunt structure that is disposed at least partially within the left atrium 2, as shown. Although the sensing element 212 is shown as attached or integrated with the arm 221, it should be understood that the sensor element 212 may be attached to any other arm or flange of the shunt structure 220, or to any other portion or feature of the shunt structure 220, such as within the flow path of the shunt structure 220.

While the sensing element 212 may be disposed within the left atrium after implantation of the device 200, the antenna associated with the sensing element 212 may be positioned or disposed in a different area or region of the heart anatomy or shunt structure 220. For example, as shown in FIG. 11, the antenna 218 may be tethered to the shunt structure 220 and/or sensing element 212 via an electrical coupling tether 227. The tether 227 may serve to both physically couple the antenna to the device 200 to maintain the antenna 218 in a certain position and/or within a certain distance or orientation with respect to the shunt structure 220, and may further serve to provide electrical signal transmission between the antenna 218 and the sensing element 212. For example, the sensing elements 212 may be configured to generate electrical signals indicative of, or relating to, pressure in at least a portion of the left atrium 2, wherein such signals may be transmitted via the tether 227 to the antenna 218, which may wirelessly transmit the signals. In some embodiments, the antenna 218 is configured to receive power inductively from an external power source through biological tissue separating the device 200 from the external system.

The antenna 218 may comprise any suitable or desirable conductive material and/or configuration that is compatible with the relevant anatomy and/or procedure. In some embodiments, the antenna 218 comprises a plurality of coils that are hermetically sealed to provide biocompatibility. By locating the antenna 218 in the coronary sinus 16, the sensor implant device 200 may advantageously provide a reduced effect or obstruction at or near the area of the shunt structure 220 relative to certain other sensor implant devices disclosed herein. In some embodiments, a delivery catheter used to deliver the device 200 to the target location may be modified to have a cavity that accommodates the presence of the antenna 218 therein.

Although illustrated in the coronary sinus, the antenna 218 may be tethered to the device 200 in any other location or position. For example, the antenna may be disposed or positioned in the left atrium 2 when deployed and tethered to the device 200. Alternatively, the tether 227 may be sufficiently long to allow for the antenna 218 to be disposed within the right atrium (not shown) when the shunt structure 220 is implanted in the wall separating the coronary sinus from the left atrium. Placement or maintenance of the antenna 218 in the right atrium rather than the coronary sinus 16 may be preferable due to the relatively greater volume of space available to the antenna 218 in the right atrium. In some embodiments, the antenna 218 represents the largest component of the sensor implant device 200 with respect to at least one dimension thereof. In some implementations, the antenna 218 is configured to be disposed in an area of the coronary sinus that is relatively wide or large (e.g., having a relatively large cross-sectional area). In some embodiments, the antenna 218 is encased in glass, polymer, or other biocompatible material.

The tether 227 may comprise an insulated wire. In some embodiments, the tether is at least partially rigid or stiff, such that the geometry and/or positioning of the antenna 218 may not readily change in response to cardiac cycles. For example, where the antenna 218 is permitted to move and/or shift freely are readily, such movement affect the frequency of transmitted signals, which may result in signal transmission error. In some embodiments, the device 200 comprises matching circuitry configured to account for or cancel out signal noise due to movement of the antenna 218.

Figure 12B:
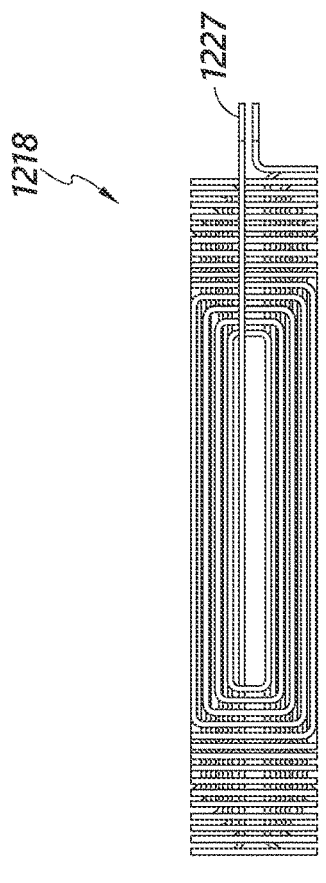
FIGS. 12A and 12B illustrate a flat spiral antenna in accordance with one or more embodiments.
Figure 12A:
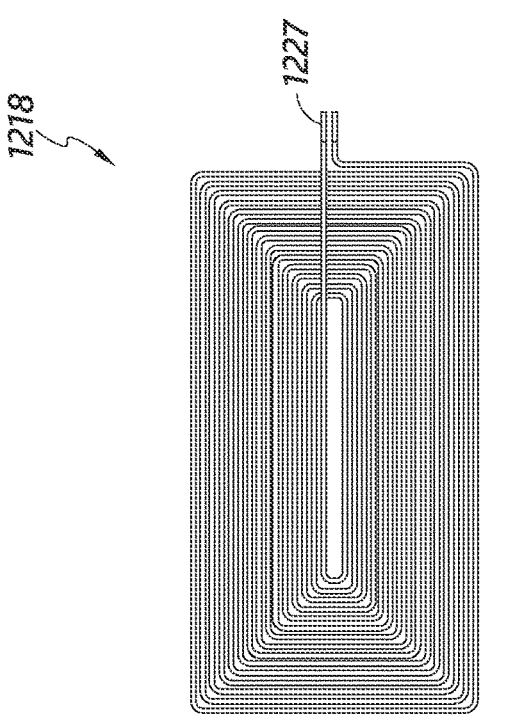

As described above, the antenna 218 of the sensor implant device 200 may be used to power the sensing element 212 and/or transmit data from the device 200 to an external system (not shown). In some embodiments, the antenna of a sensor implant device has a flat shape or form when deployed. For example, the antenna may comprise winds of conductor in a spiral inductor configuration/geometry, as shown in FIG. 12A. The flat spiral antenna 1218 of FIG. 12A may be sealed in a biocompatible tape or membrane, such as polydimethylsiloxane or another biocompatible elastomer. The flat antenna 1218 may advantageously be at least partially flexible to allow for folding, rolling, or compression thereof for fitting within a delivery catheter as described herein. For example, FIG. 12B shows the flat spiral antenna 1218 in a rolled or folded delivery configuration, which may provide a relatively smaller profile with respect to one or more dimensions of the antenna 1218. The flat antenna 1218 may be sutured to a wall of an atrium or coronary sinus or may be freely disposed in, or wedged or positioned in, an atrium or coronary sinus.

Figure 13:
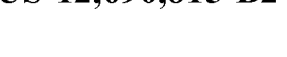
FIG. 13 illustrates a sensor implant device having a wrapped antenna in accordance with one or more embodiments.

In some implementations, the present disclosure provides sensor implant devices having a shunt structure and a power and/or data transmission antenna wrapped around at least a portion of the shunt structure. For example, as shown in FIG. 13, a sensor implant device 1300 may comprise a shunt structure 1320 including one or more arms 1321 and a flow path conduit or barrel portion 1322. With respect to shunt structures disclosed herein, the term "conduit" is used according to its broad and ordinary meaning, and may refer to any channel, duct, aperture, canal, pipe, tube, or similar structure, whether solid or having openings or mesh-type form.

The pressure sensor element 1312 may comprise a pressure transducer configured to convert environmental pressure into electrical signals. The sensor element 1312 may further be integrated with control circuitry for processing and/or transforming pressure-based signals. Although the sensor elements 1312 is illustrated as being attached to or integrated with an arm member 1321 of the sensor implant device 1300, it should be understood that the sensor element 1312 may be attached to or associated with any portion or member, or feature of the shunt structure 1320, as described in detail herein.

The antenna 1318 may comprise a conductive wire or wire loops that is/are insulated in some manner. For example, in some embodiments, the antenna 3018 may comprise wire incorporated in an insulated preformed tape, or other flexible insulating membrane. The antenna 1318 may be used to wirelessly communicate with an external system when the sensor implant device 1300 is implanted in the patient. Furthermore, the antenna 1318 may be configured to receive inductive power transfer from an external system, as described herein. The sensor implant device 1300 may be delivered in a collapsed state, wherein the shunt structure is at least partially collapsed, as described herein. In order to accommodate such compression, the antenna 1318 may be incorporated in a carrier tape or other membrane that is configured to fold and be delivered within the catheter. When the shunt structure 1320 expands, the antenna may also be designed or configured to expand to assume a deployed state.

Figures 14A, 14B:
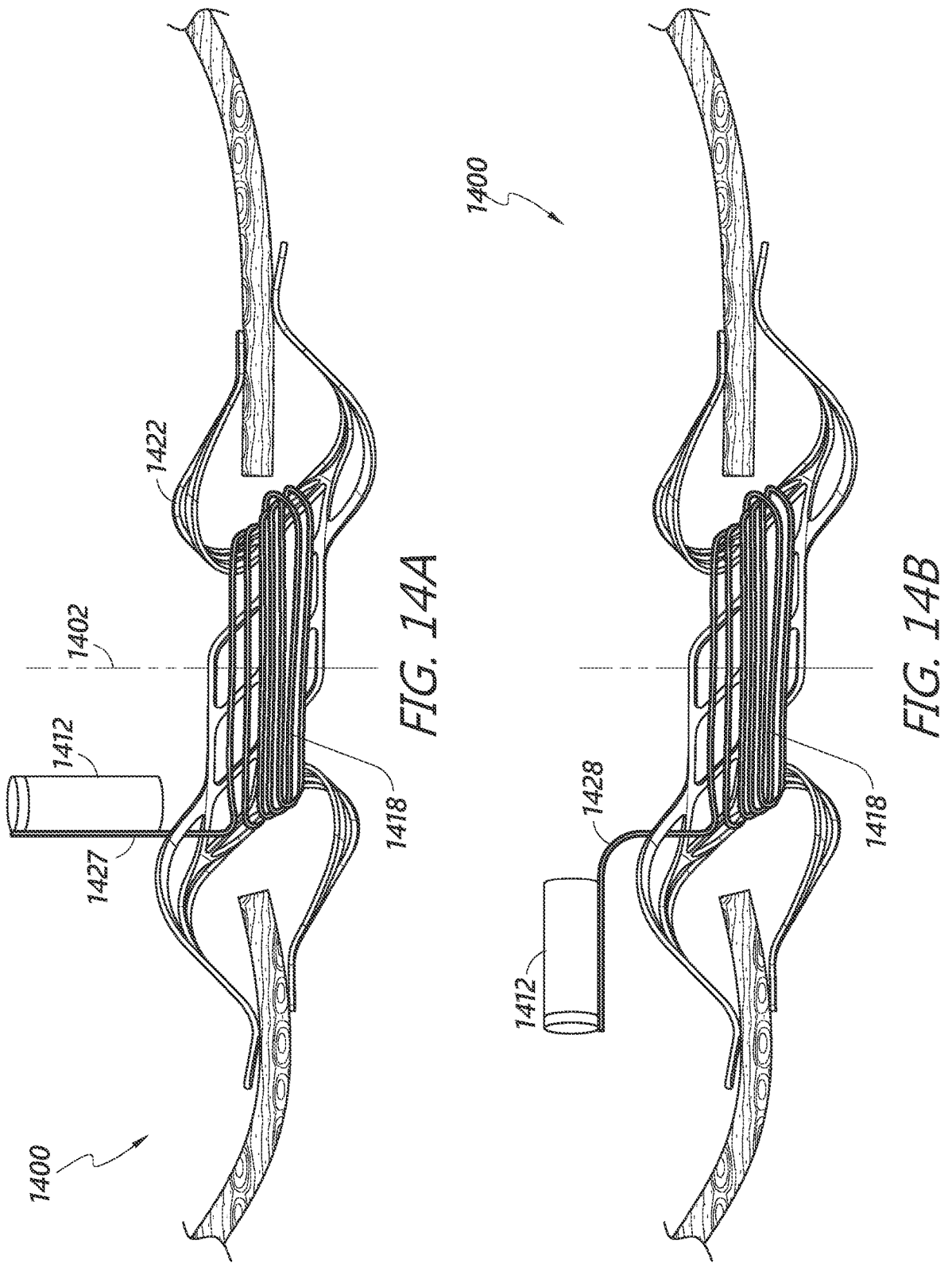
FIGS. 14A and 14B illustrate sensor implant devices in accordance with certain embodiments.

In the illustrated embodiment of FIG. 13, the sensor element 1312 is attached to or integrated with an arm member 1321, which extends generally along a longitudinal dimension or axis 1301 of the shunt structure 1320. However, in certain embodiments, as shown in FIGS. 14A and 14B, a sensor implant device 1400 including an antenna 1418 wrapped around a flow path structure or conduit 1322 may be coupled to a sensor element 1412 that extends away from the antenna along a dimension parallel to the flow path axis 1402. For example, in the embodiment of FIG. 14A, the sensor element 1412 may be connected to the antenna 1418 via a conductor 1427 that extends generally parallel with the flow path axis, such that the sensor element 1412 is disposed within or near the flow path 1402 of fluid through the shunt. Alternatively, the sensor element 1412 may be coupled to the antenna 1418 via a shape-set conductor 1428 configured to hold or maintain the sensor element 1412 away from the flow path of the shunt, as shown.

Figure 15:
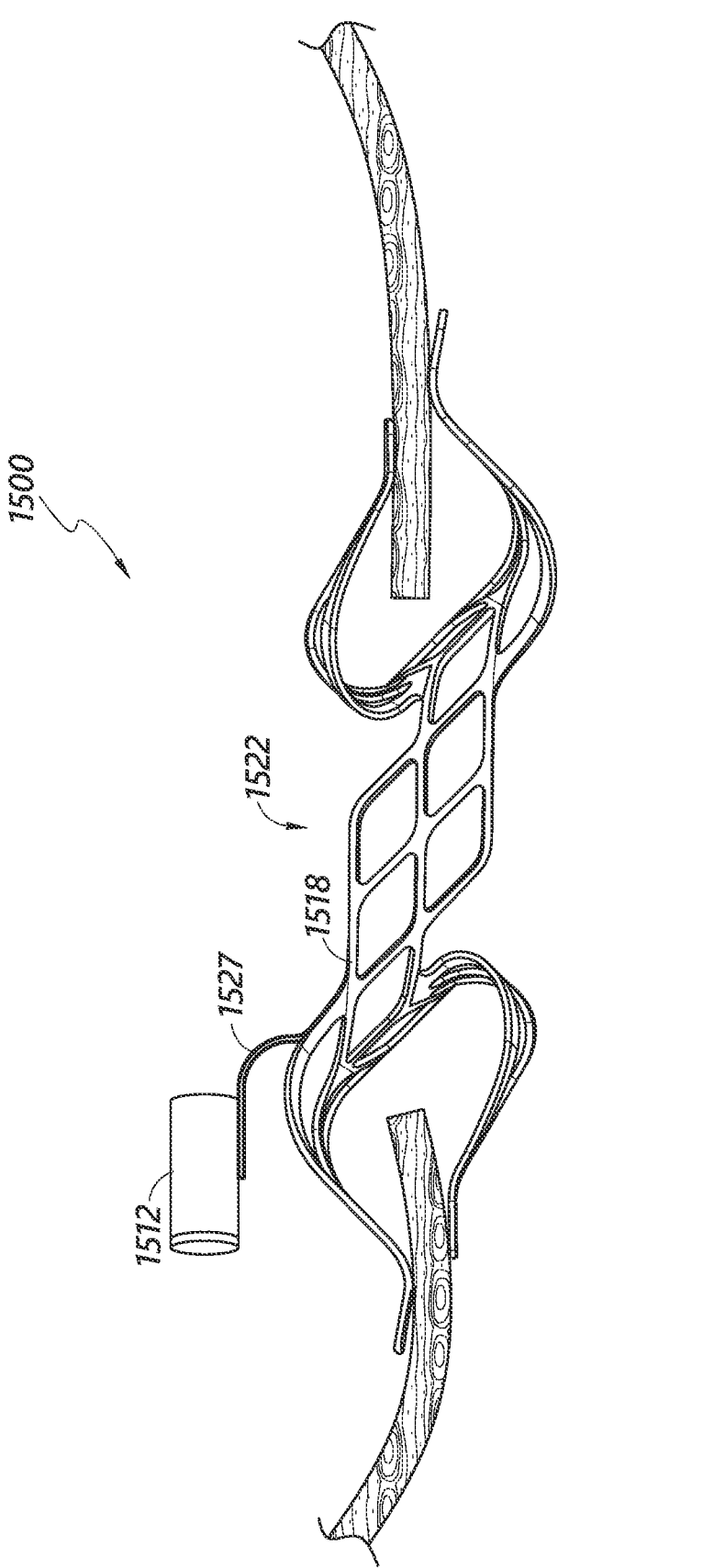
FIG. 15 illustrates a sensor implant device having a shunt structure configured to operate as an antenna in accordance with one or more embodiments.

In some implementations, the present disclosure provides sensor implant devices having a shunt structure and a power and/or data transmission antenna integrated with at least a portion of the shunt structure. For example, as shown in FIG. 15, a sensor implant device 1500 may comprise a shunt structure 1520 coupled to a sensor element 1512 via a connector 1527. The shunt structure may be metal or comprise other conductive materials. The shunt structure 1518 comprises conductive material, such as memory metal (e.g. Nitinol), wherein the shunt structure 1518 also serve as an antenna for data and/or power transmission in accordance with principles disclosed herein. The sensor element 1512 may comprise a pressure sensor. In some embodiments, the connector 1527 comprises an at least partially rigid wire or structure configured to allow for the transmission of electrical signals, such as electrical signals indicating pressure readings obtained by the sensor element 1512, from the sensor element 1512 to the antenna shunt body 1518. The antenna shunt structure 1518 can transmit such signals wirelessly for reception external to the patient in whom the sensor implant device 1500 is implanted.

The conductive shunt body 1518 of the implant device 1500 may further serve to receive wireless power from an external power source through biological tissue of the patient. In some embodiments, at least a portion of the shunt structure 1518 is coated with an insulating material and/or a conductive material, such as gold. The conductive shunt structure 1518 may comprise titanium. Although certain shunt structure/form is illustrated FIG. 15, it should be understood that the conductive shunt structure 1518 may have any form or shape. For example, in one embodiment, the flow path conduit or barrel portion 1522 of the shunt structure 1518 has a coil-/spring-type shape, wherein arm members of the device are attached to the barrel/conduit portion and electrically isolated therefrom in some manner. The coil/spring shape of the barrel/conduit portion may serve as an inductive antenna and may function according to principles and embodiments disclosed herein with respect to wireless data and/or power transfer.

Figure 16A:
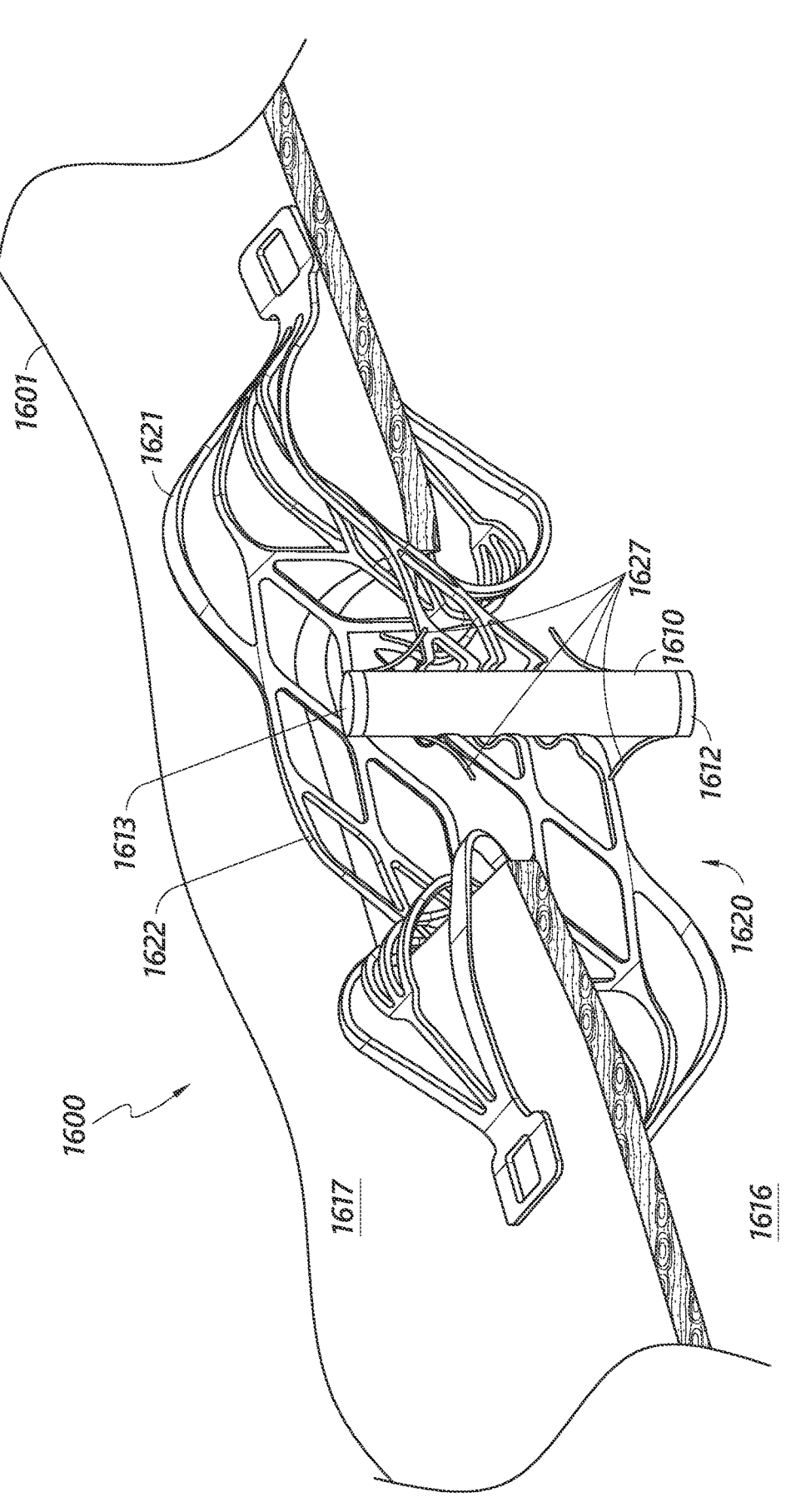
FIG. 16A-16C illustrate a sensor implant device in accordance with one or more embodiments.
Figures 16B, 16C:
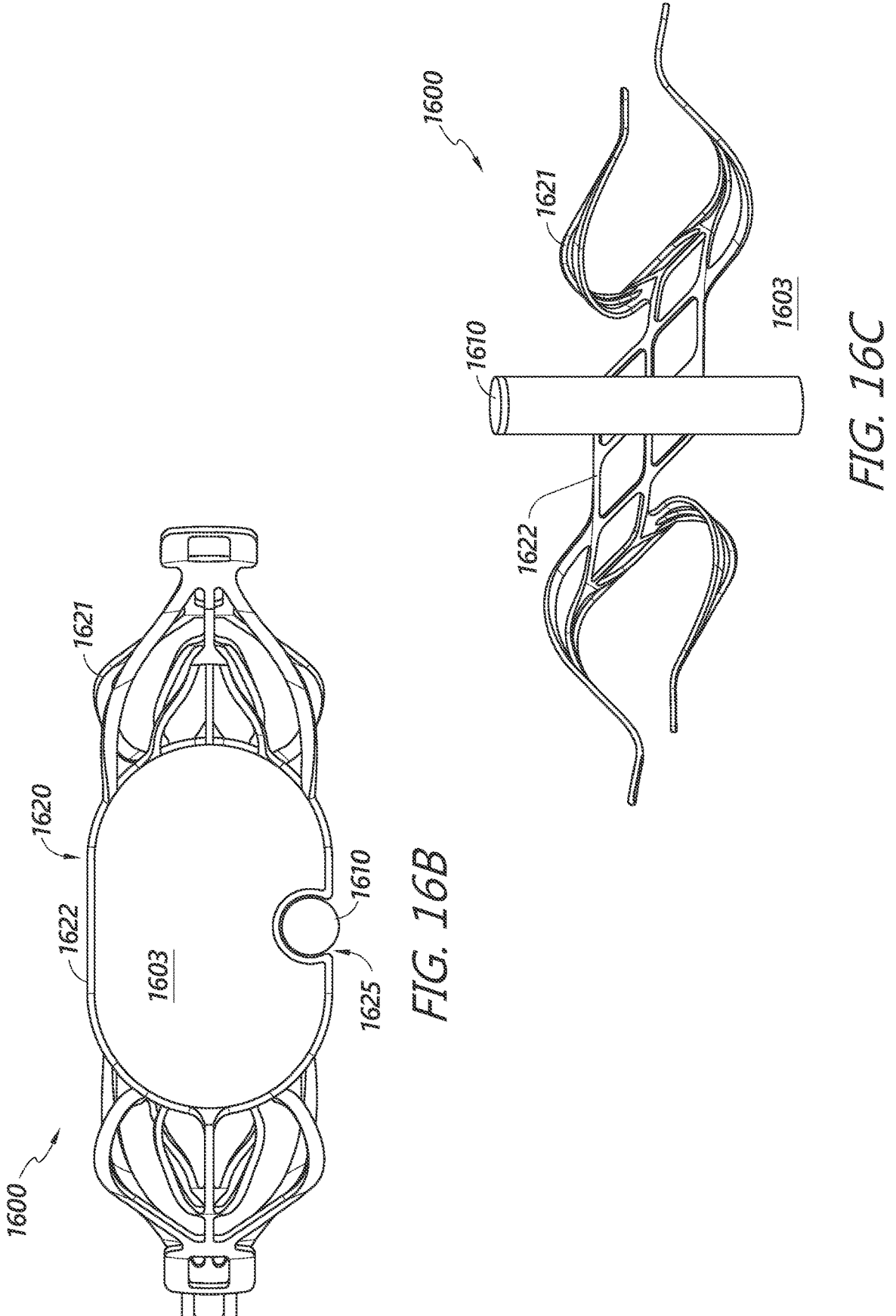

In some implementations, the present disclosure provides sensor implant devices having a sensor attached to a shunt structure such that the sensor lies at least partially in the flow path of the shunt structure. FIG. 16A-16C illustrate a sensor implant device 1600 having a sensor 1610 integrated therewith, such as a pressure sensor as described herein. In the embodiment illustrated in FIGS. 16A 16-C, the sensor 1610 is attached to, or otherwise integrated with, a flow path barrel or conduit portion 1622 of a shunt structure 1620, such that the sensor 1610 is disposed within or near the flow path channel associated with the barrel/conduit 1622.

FIG. 16A is a perspective view of the sensor implant device 1600. In the embodiment illustrated in FIG. 16A, the sensor 1610 has an elongate cylindrical shape. However, it should be understood that sensors in accordance with embodiments of the present disclosure may have any form, shape, configuration and/or orientation. In some embodiments, the sensor 1610 includes a first sensor element 1612 at a first end of the sensor 1610 that is disposed on a first side 1616 of a tissue wall 1601 and the shunt structures 1620 when implanted in a patient, such as in a wall separating the coronary sinus from the left atrium. For example, the sensor 1612 may be positioned to be exposed within the left atrium, which may be represented by the side or region 1616 in the illustrated diagram. The sensor 1610 may further comprise a second sensor 1613 disposed on an opposite side of the sensor 1610. For example, the sensor 1613 may be configured and positioned to be exposed in a chamber or area associated with an opposite side of the tissue wall 1601 and/or shunt structure 1620, such as within the coronary sinus. With respect to interatrial shunting, the sensor elements 1612, 1613 may be disposed or positioned in perspective atria, wherein one sensor element provides pressure readings associate with the left atrium and the other provides pressure readings associate with the right atrium, as described in detail above. Using two sensor elements as shown in FIG. 16A may allow for measurement of differential pressure drop across the shunt structure 1620.

With the sensor 1610 disposed or attached in or near the flow path channel of the shunt structure 1620, the sensor 1610 may be configured to provide sensor readings that can be used to indirectly measure flow across or through the shunt structures 1620 based at least in part on fluid momentum associated with fluid contacting the sensor element(s). Furthermore, the sensor(s) may generate readings relating to velocity of flow through the shunt, wherein such readings may be used to determine or indicate undesirable occlusion or closing-off of the shunt flow path. In certain embodiments, pressure waveforms generated using the sensor(s) may be used to generate and/or maintain a waveform profile relating to the pressure readings. Changes in the pressure reading profile may indicate health complications and may therefore be used to trigger alerts or notifications, which may be relied upon to alter drug or other therapies. In some embodiments, the pressure readings from the sensor(s) are analyzed to determine average, diastolic, and/or systolic pressure data points.

In the embodiments of FIGS. 16A-16C, the sensor 1610 is mounted or attached at or near the orifice or channel of the shunt structure 1620, rather than to one or more arm members, as described above. The sensor 1610 may be built into, or otherwise integrated with, the shunt structure 1620, or may be otherwise attached or associated therewith. Although FIGS. 16A-16C illustrate the sensor 1610 attached or integrated with the barrel/conduit portion 1622 of the shunt structure 1620 on an outside surface thereof, it should be understood that in some embodiments the sensor 1610 may be disposed, attached, or otherwise integrated with the barrel/conduit portion 1622 on an inside surface thereof. With respect to the illustrated embodiment, the sensor 1610 may fit within a pocket/receptacle feature 1625 of the barrel/conduit 1622. In some embodiments, the sensor 1610 comprises or is associated with one or more projections 1627 configured or designed to hold or secure the sensor 1610 to the shunt structure 1620.

FIG. 16B shows a front view of the sensor implant device 1600 in accordance with one or more embodiments. FIG. 16B shows the sensor 1610 nested in a pocket/receptacle feature 1625 associated with the barrel portion 1622 of the shunt structure 1620. FIG. 16C shows a bottom or top view of the sensor implant device 1600, showing the sensor 1610 disposed in the flow path 1603 of the shunt structure. In some embodiments, the sensor 1610 is sutured to the shunt structure. In some embodiments, the sensor 1610 is held within a sock or pouch that is sutured or otherwise attached to the shunt structure 1620.

Figure 17:
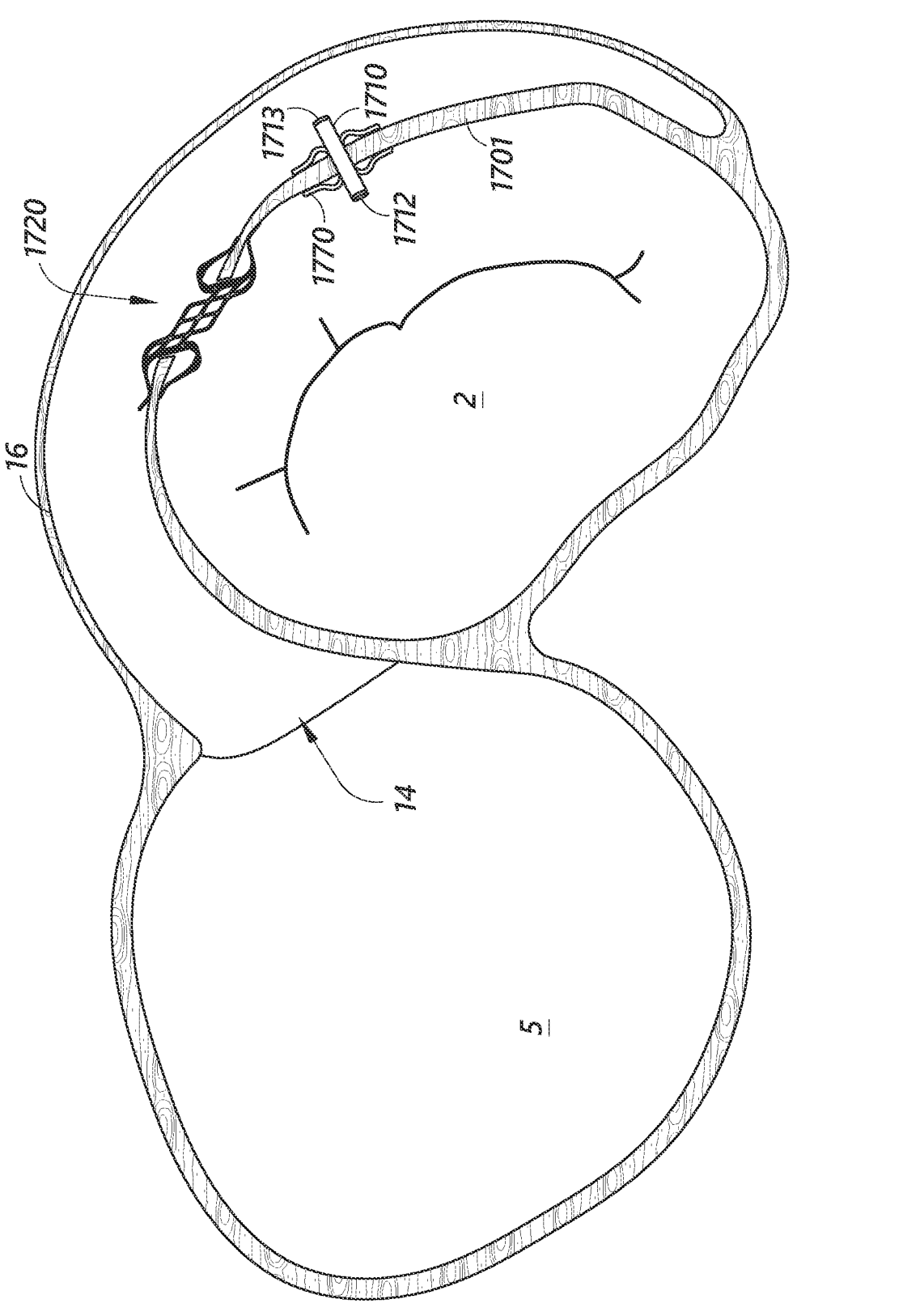
FIG. 17 illustrates a sensor device implanted in a tissue wall in accordance with one or more embodiments.

In some embodiments, a pressure sensor device may be implanted through the wall separating the left atrium from the coronary sinus. FIG. 17 shows a sensor device 1710 implanted in the wall 1701 separating left atrium 2 from the coronary sinus 16. In some embodiments, the sensor device 7010 may be implanted in the tissue 1701 as part of the procedure to implant a shunt structure 1720 in the same wall or area as the sensor device 7010, as shown. The sensor device 1710 may be carried in the same delivery catheter used to deliver the shunt structure 1720 or may be delivered using a separate catheter. In some embodiments, the sensor 1710 is deployed in the same procedure in which the shunt structure 7020 is deployed.

Figure 18:
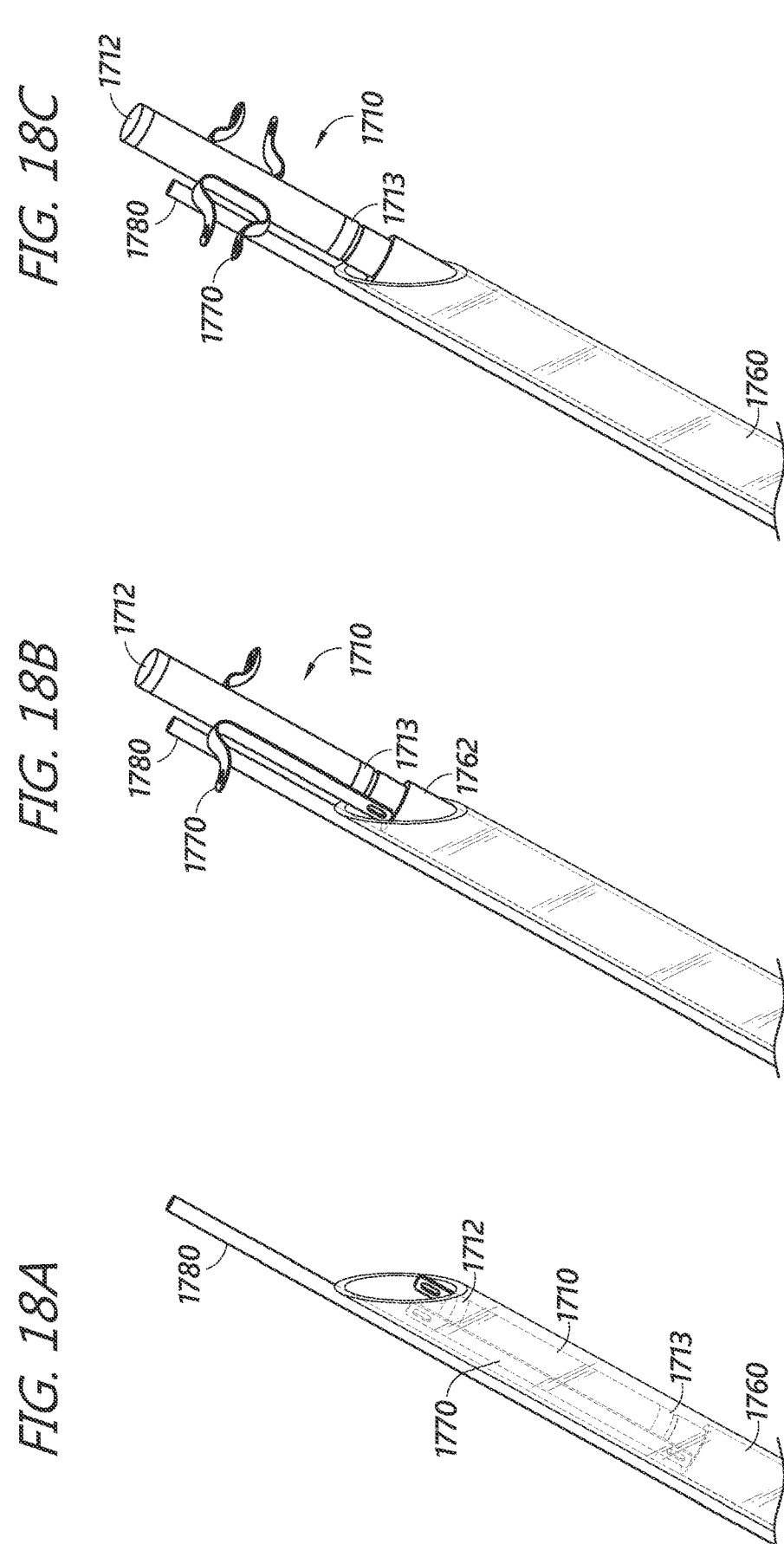
FIGS. 18A-18C illustrate a delivery catheter assembly in accordance with one or more embodiments.

FIGS. 18A-18C illustrate deployment from a delivery catheter 1760 of a sensor device 1710 configured to be implanted in a tissue wall in accordance with one or more embodiments. The sensor device 1710 may include certain wall anchor features 1770. In a delivery configuration, the anchor feature(s) 1770 may be in a straightened or extended configuration, as shown in FIG. 8A. As the sensor device 1710 is deployed from the delivery catheter 1760, the tissue anchor feature 1770 may be configured to extend outward and provide compressive force on a target tissue wall, such as the wall separating left atrium from the coronary sinus. The sensor device 1710, as shown, includes a sensor element at each end of the sensor, namely the sensor element 1712 and the sensor element 7013. The sensor device 1710 may be deployed from the delivery catheter 1760 using a pusher device 1762, as shown in FIG. 18B. The anchor feature(s) 1770 may be used to anchor the sensor device 1710 adjacent to and/or near an implanted shunt structure, as shown in FIG. 17.

Using both pressure sensors 1712, 1713, the sensor device of 1710 may be configured to detect pressure readings that may be used to determine pressure differentials between the left atrium and the coronary sinus. Because pressure in the coronary sinus may be related to pressure in the right atrium, readings of pressure on the sensor element disposed in the coronary sinus may be used to determine sensor measurements relating to right atrial pressure. With the orientation and disposition shown in FIG. 17, the sensor elements 1712 and 1713 may have little or no flow passing by the sensor elements, such that the pressure readings associated therewith are not substantially influenced by flow velocity. The sensor device 7010 may be deployed with the aid of a guide wire 1780, which may be delivered to the right atrium through the inferior vena cava or superior vena cava, and further through the coronary sinus to the target delivery site. Access to the right atrium may be via jugular or femoral access. For example, with jugular access, access to the right atrium may be via the superior vena cava, whereas procedures involving femoral access may provide access to the right atrium via the inferior vena cava.

In some embodiments, the distal tip of the sensor 1710 comprises or is connected to a screw point or other tissue piercing feature (not shown) that may be used to drive the sensor 1710 through the tissue wall separating the left atrium 2 from the coronary sinus 16. Such tissue-piercing functionality may reduce or obviate the need for tissue dilation or piercing separately for the sensor 1710. The sensor 1710 may further comprise a jacket or covering made with lubricious anti-thrombus-forming material. Such covering may be used to house the guide wire 1780 and/or anchor features 1770.

Figure 19:
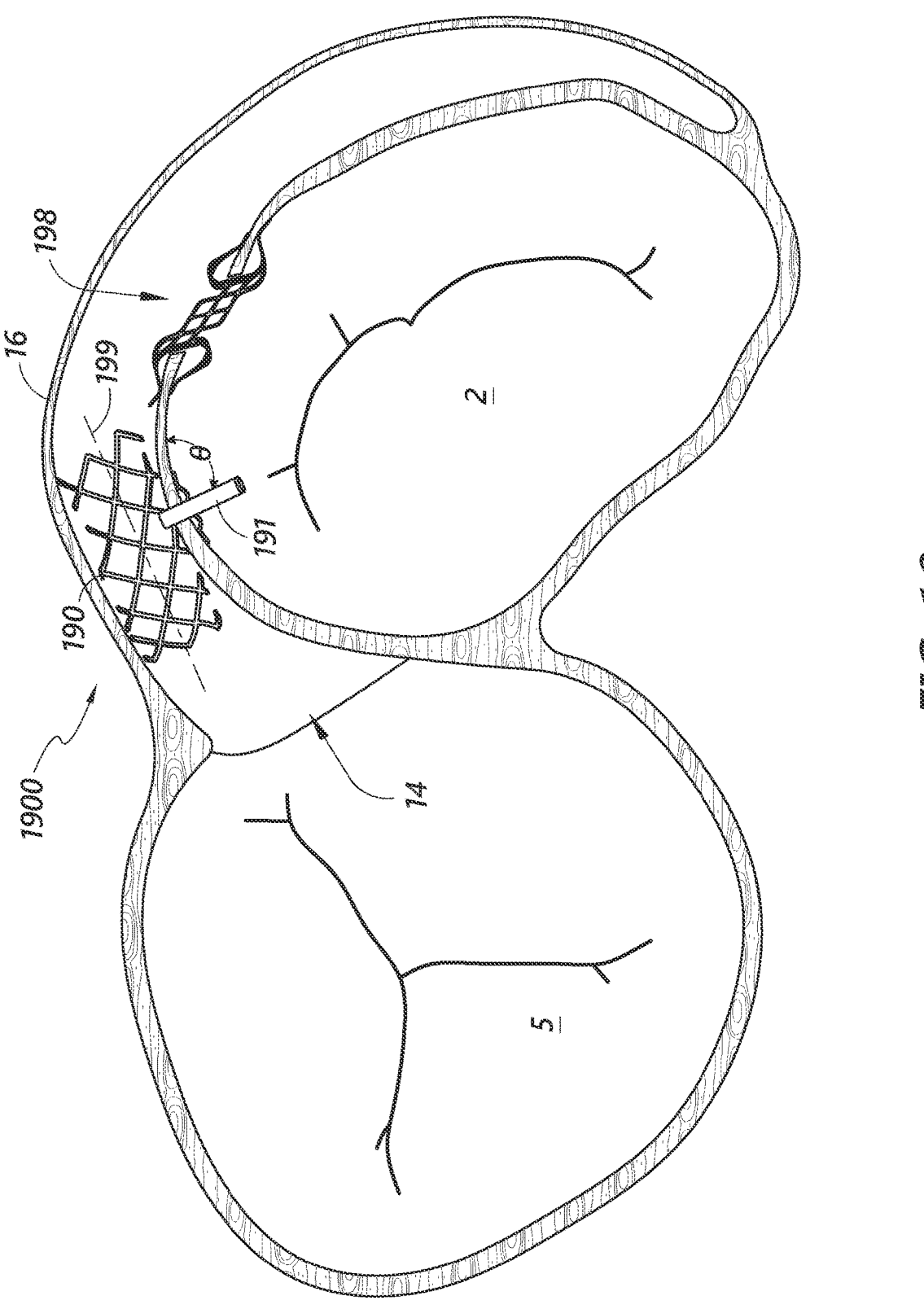
FIG. 19 illustrates a sensor implant device including a stent structure in accordance with one or more embodiments.

FIG. 19 illustrates a sensor implant device 1900 including a stent structure 190, which is integrated with or attached to a sensor 191, as shown. The stent structure 190 may advantageously be implemented in the coronary sinus, wherein at least a portion of the sensor implant device 1900 is configured to pass through the wall between the left atrium 2 and the coronary sinus 16. In some embodiments, the sensor 191 is mounted to the stent structure 190 using any suitable or desirable mounting or attachment means or mechanism, including a clip, tab, suture, screw, or other anchor or attachment means or mechanism. The stent structure 190 may serve to anchor the sensor 191 in the coronary sinus. In some configurations, the sensor 191, as attached or integrated with the stent structure 190, is configured to be positioned or configured such that it is secured relative to the stent structure 190 at an angle, as illustrated. In some embodiments, the sensor is positioned at a substantially right angle with respect to a longitudinal axis 199 of the stent structure 190, such that the sensor 191 Jets out into the left atrium 2. The stent structure 190 may advantageously provide a relatively solid anchoring point for the sensor 191, such that the sensor 191 does not move substantially after implantation thereof and disposition in the left atrium 2.

Figure 20:
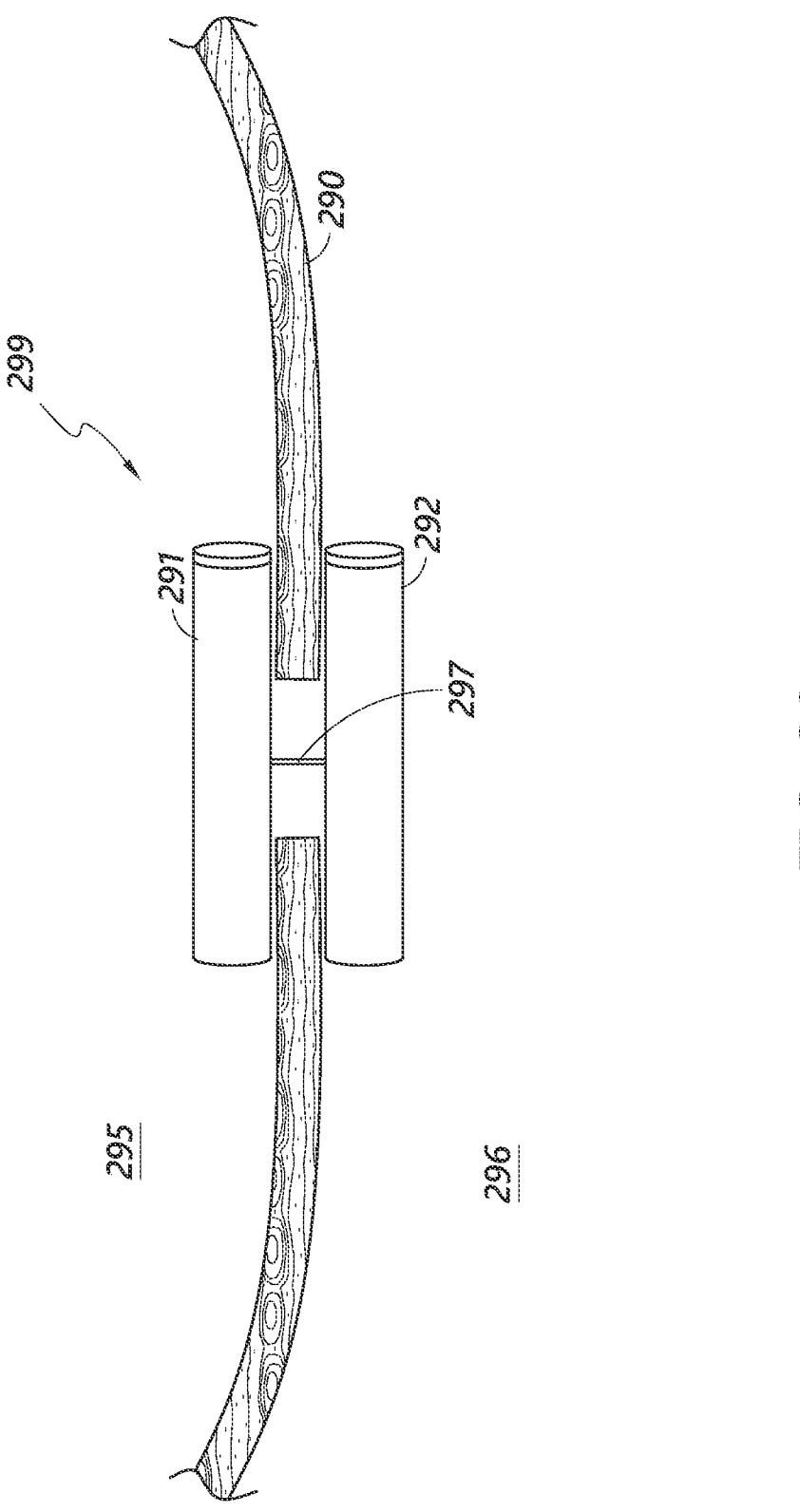
FIG. 20 illustrates a sensor implant device including two sensors in accordance with one or more embodiments.

FIG. 20 illustrates a sensor implant device 299 including two sensors 291, 292, which may be pressure sensors or other types of sensors. The sensors are configured to be implanted on opposite sides of the tissue wall 290. For example, the sensors 291, 292 may be implanted and positioned on opposite sides of the wall separating the left atrium from the coronary sinus, as described in detail herein. The sensors 291, 292 may be secured to one another by an attachment means 297, which may comprise one or more rigid and/or flexible members, such as a strap, bar, suture, arm, or the like. In some embodiments, the attachment member 297 may be configured to be tightened to a desirable tension between the sensors 291, 92, such that the sensors are secured and held against the tissue wall 290. Each of the sensors 291, 292 may be configured to measure a physiological parameter, such as fluid pressure, or any other parameter, in its respective chamber or area of implantation. For example, the sensor 291 may be configured to measure one or more parameters associated with the chamber or area 295 on one side of the tissue wall 290, whereas the sensor 290 to may be configured to measure one or more parameters on the opposite side 296 of the tissue wall 290, as shown. With multiple sensors in multiple chambers/vessels, the implant device 299 may provide for differential parameter (e.g., pressure) measurements and/or other differential or comparative parameter analysis.

Sensor and Shunt Implantation Using Common Guidewire

Figure 21A:
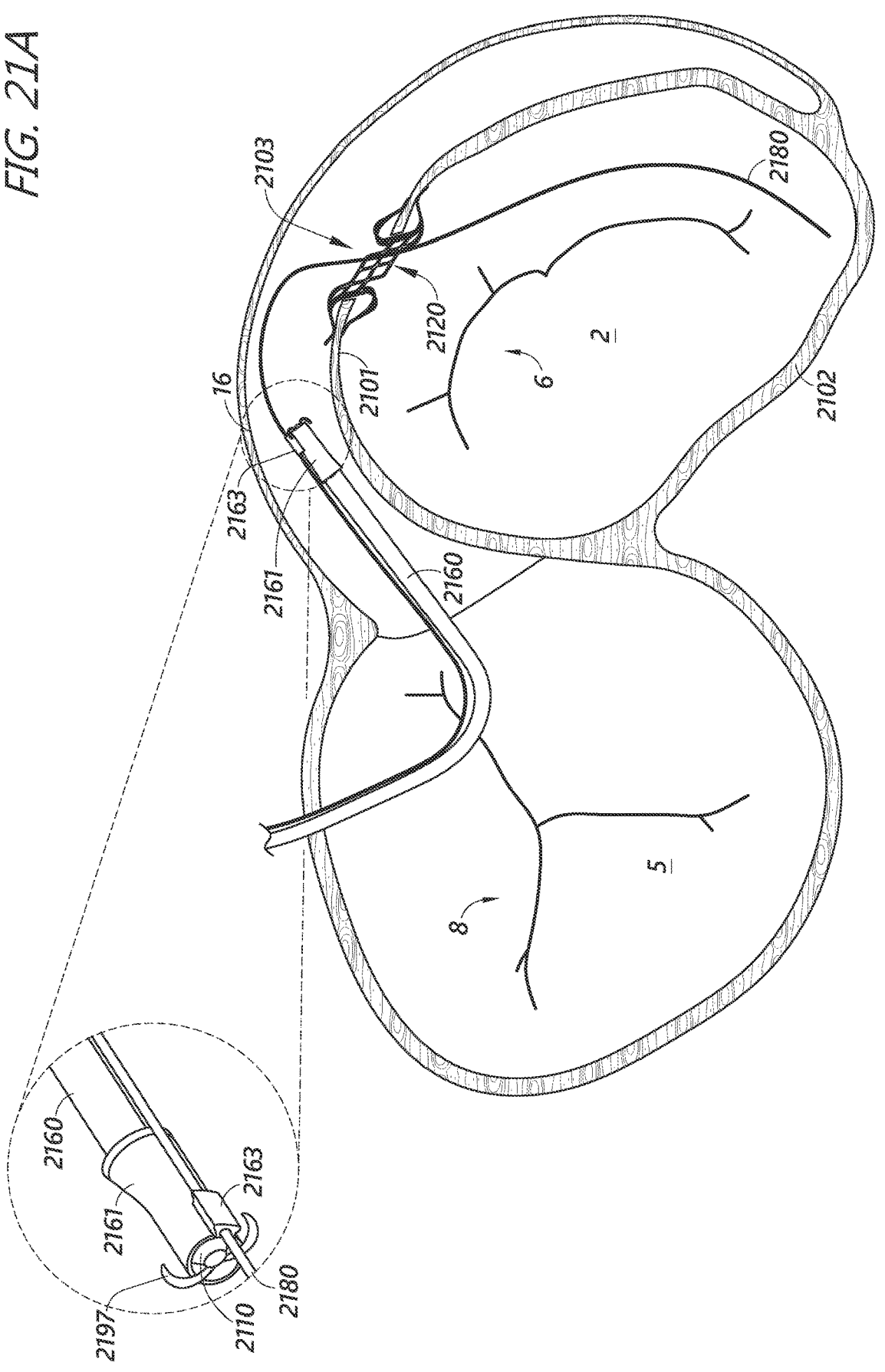
FIGS. 21A-21D illustrate stages of a process for implanting a pressure sensor or other type of sensor in an atrium or other region of the heart in accordance with one or more embodiments.

In some implementations, procedures for implanting a sensor device, such as a pressure sensor device, in an atrium, coronary sinus, or other chamber or region of the heart or body of a patient may be incorporated with a procedure to implant a separate shunt structure. FIGS. 21A-21D illustrate stages of a process for implanting a pressure sensor or other type of sensor in an atrium or other region of the heart. FIG. 21A shows a guidewire 2180 that has been introduced to the left atrium 2 of the heart through a coronary sinus access opening 2103 in a wall 2101 separating the left atrium 2 from the coronary sinus 16. In some embodiments, the guidewire 2180 may have been introduced into the left atrium 2 in connection with a procedure for implanting a shunt structure 2120 in the wall 2101 to provide shunting between the left atrium 2 and the coronary sinus 16. That is, when implanting the shunt structure 2120, the procedure may involve advancing the guidewire further through the opening 2103 to a location within the left atrium 2 where a sensor device is desired to be implanted.

After implantation of the shunt structure 2120 and positioning of the guidewire 2180, the process may involve advancing a delivery catheter 2160 over the guidewire 2180, the delivery catheter 2160 carrying a sensor device. The delivery catheter 2160 may be a different catheter than was used to deliver the implanted shunt structure 2120 or may be the same catheter used to deliver the shunt structure 2120. In some embodiments, the delivery catheter comprises a distal end portion 2161 having a rapid-exchange slot or feature 2163, which may be configured to engage the guidewire 2180, such that the delivery catheter 2160 may be guided or advanced along the path defined by the guidewire 2180. The guidewire slot or engagement feature 2163 can be used to transition the guidewire 2180 to the delivery catheter system 2160. As shown, the slot or engagement feature 2163 may provide a side-running guide for advancement of the delivery catheter 2160. The use of a side-running guidewire engagement feature, as shown in FIG. 21A, may advantageously allow for the delivery of a solid-body sensor device 2110 within a lumen or cavity of the delivery catheter 2160, such as at least partially within the end portion 2161.

Figure 21B:
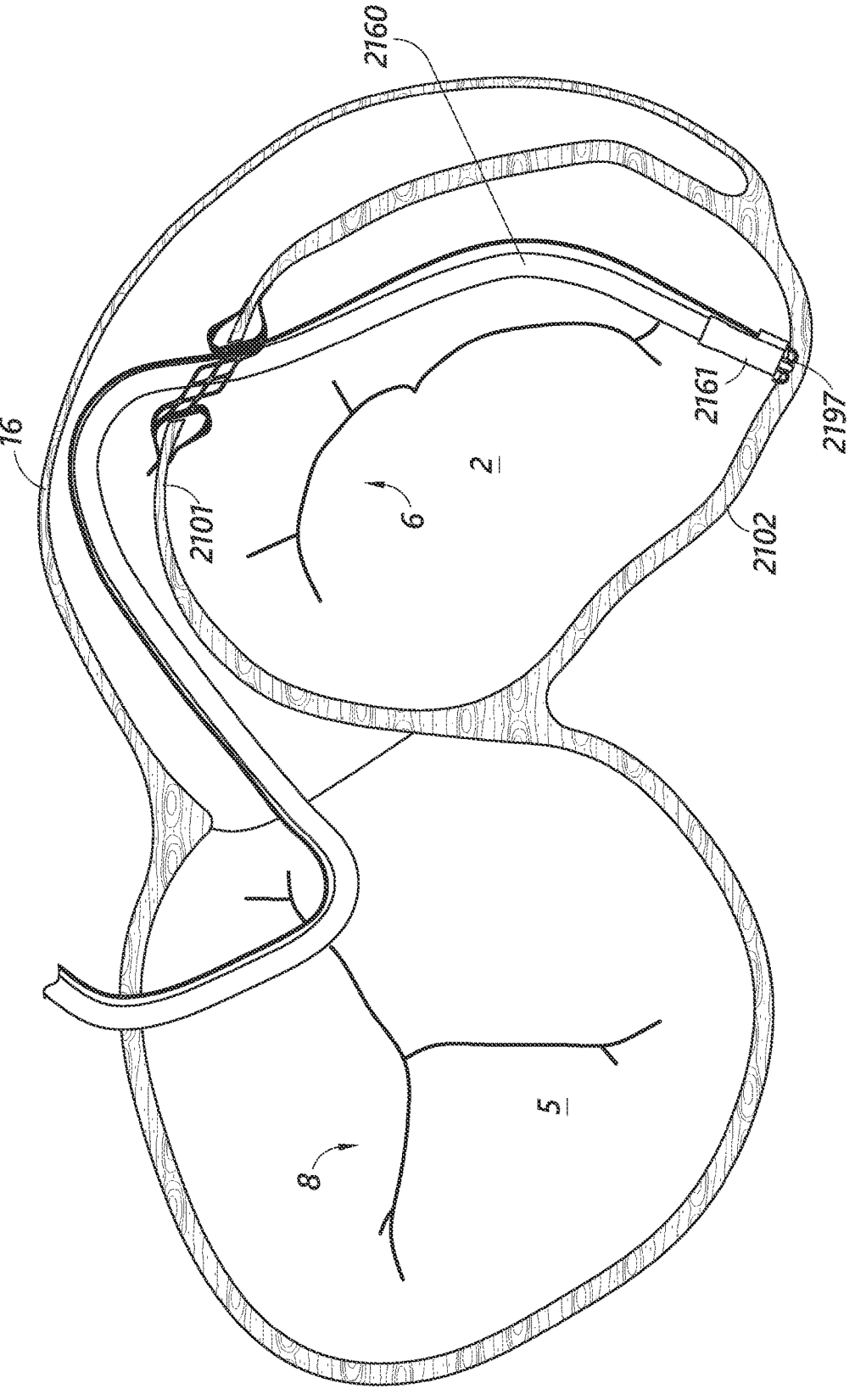

FIG. 21B shows the delivery catheter 2160, and in particular the distal end portion 2161, advanced to the target sensor implantation site at a wall portion 2102 of the atrium 2. The sensor 2110 (see FIG. 21C) may be implanted using tissue anchor features 2197 that may be attached to or integrated with the sensor 2110. Therefore, as shown in FIG. 21B, by applying force with the delivery catheter 2160 to puncture or engage the anchor features 2197 in the tissue 2102, the anchor features 2197 may become embedded or secured into the tissue 2102.

Figure 21C:
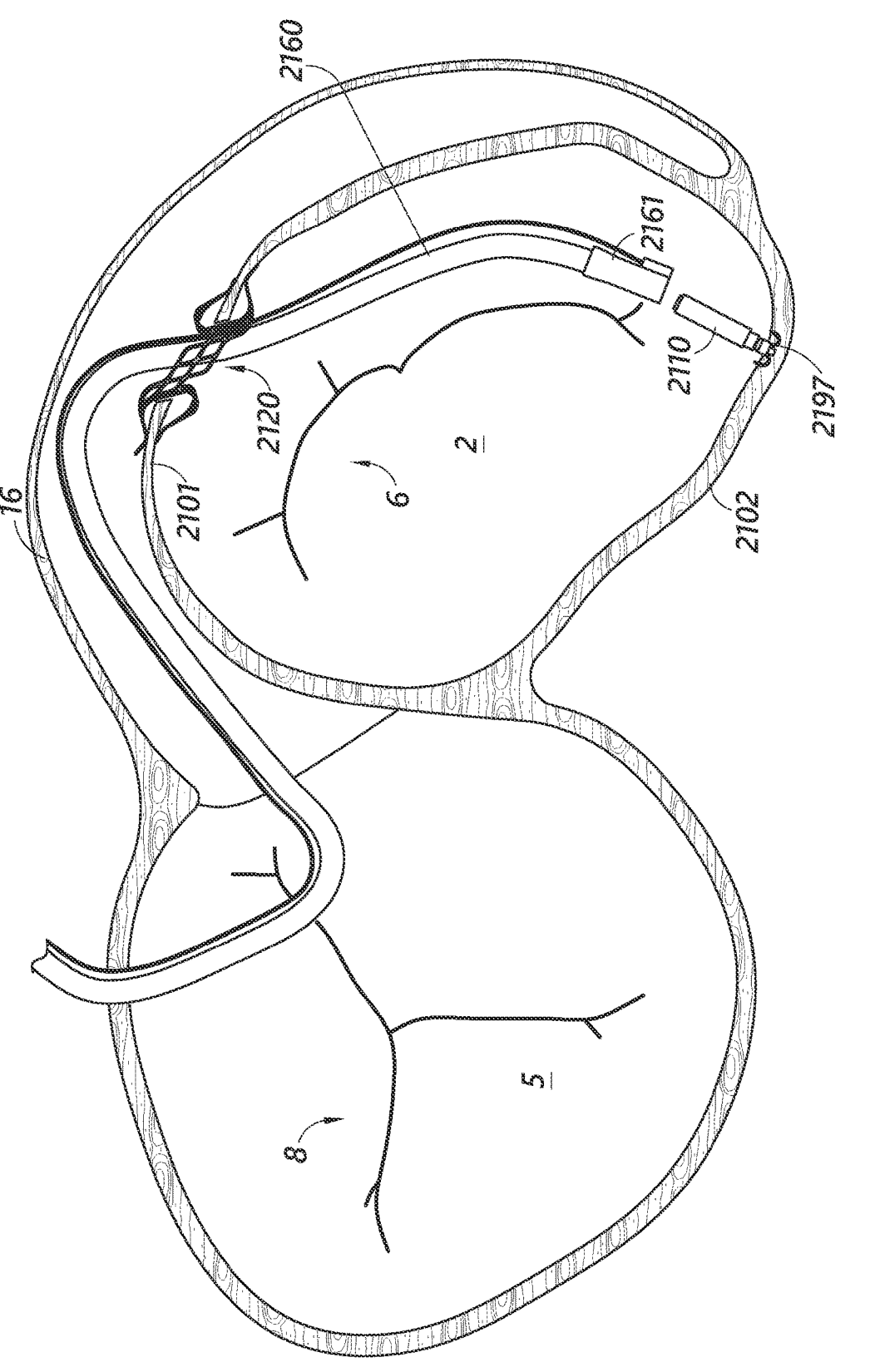
Figure 21D:
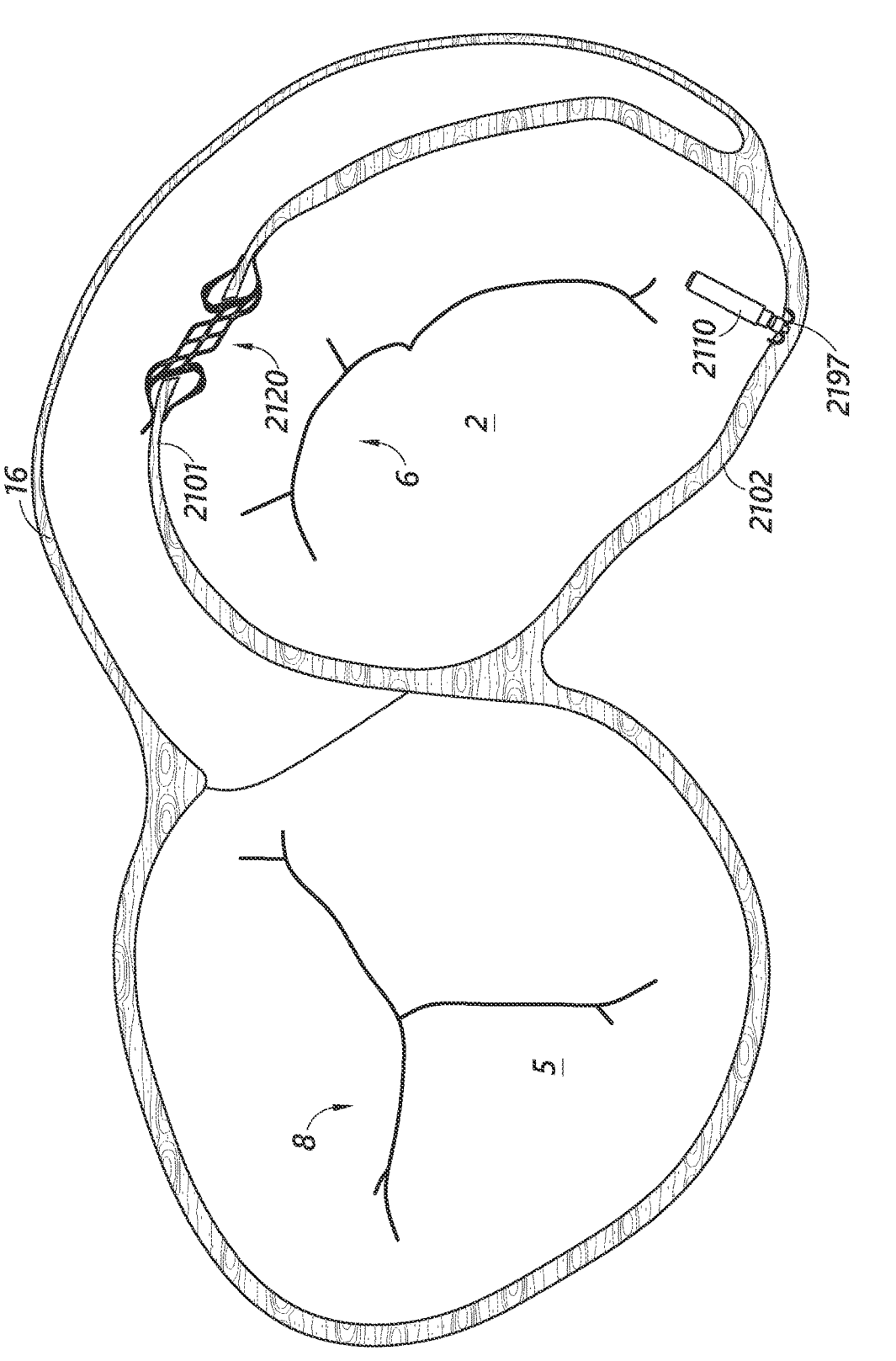

After the tissue anchor(s) 2197 have been embedded in the tissue 2102, as shown in FIG. 21C, the process may involve releasing the sensor 2110 from the delivery catheter 2160 and/or distal end portion 2161. The delivery catheter 2160 may then be withdrawn from the cardiac anatomy, leaving the sensor 2110 implanted at the target location, as well as the shunt structure 2120 in its separate implantation location, as shown in FIG. 21D. Therefore, the process illustrated in FIGS. 21A-21D may allow for implantation of a shunt structure and a separate pressure sensor at separate locations of an atrium or other cardiac region using a single guidewire and atrium access opening, which may reduce risks of damage to the cardiac anatomy and/or provide a more efficient mechanism for implantation of such devices.

Figure 22:
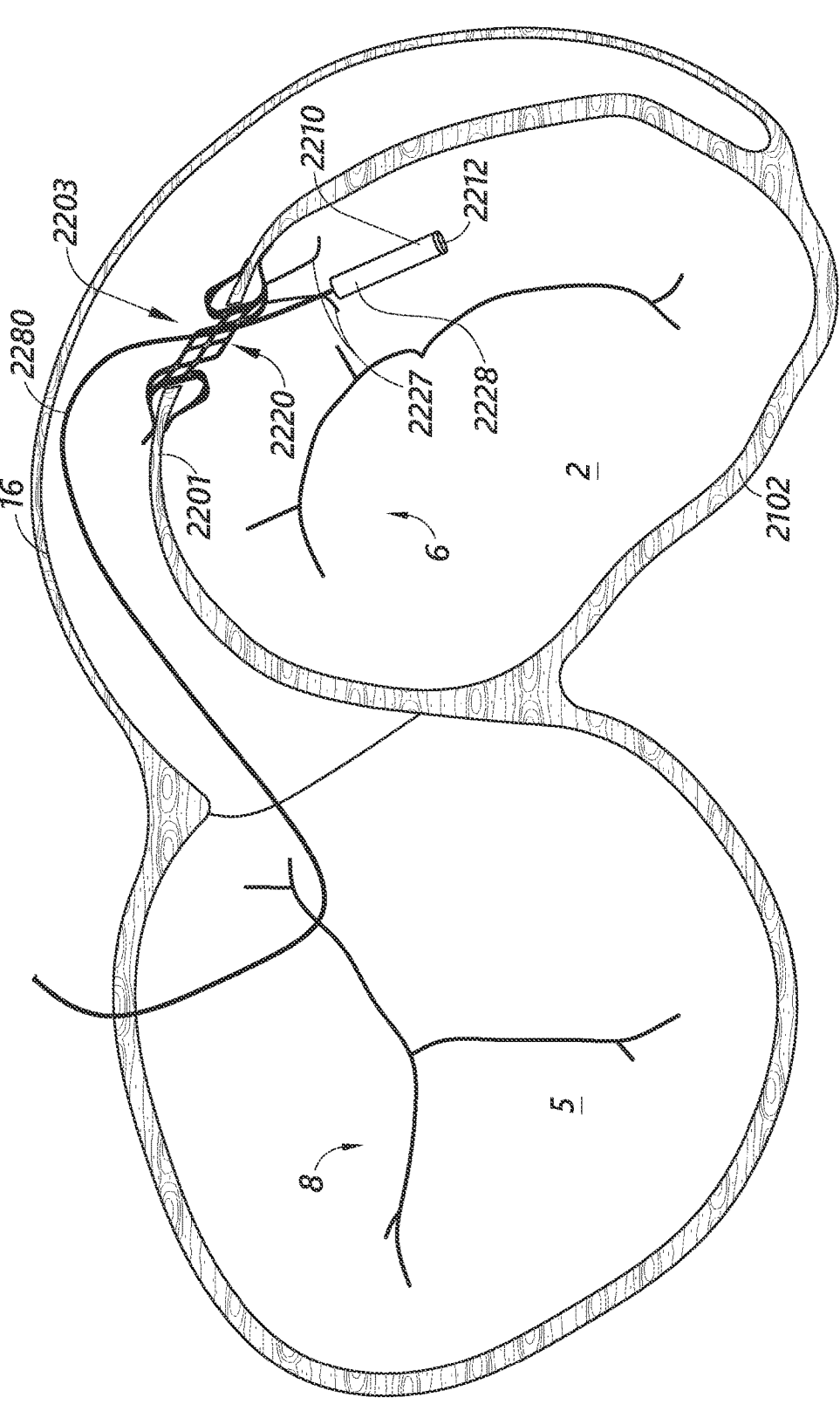
FIGS. 22 and 23 illustrates stages of a process for docking a sensor device on a shunt structure in accordance with one or more embodiments.
Figure 23:
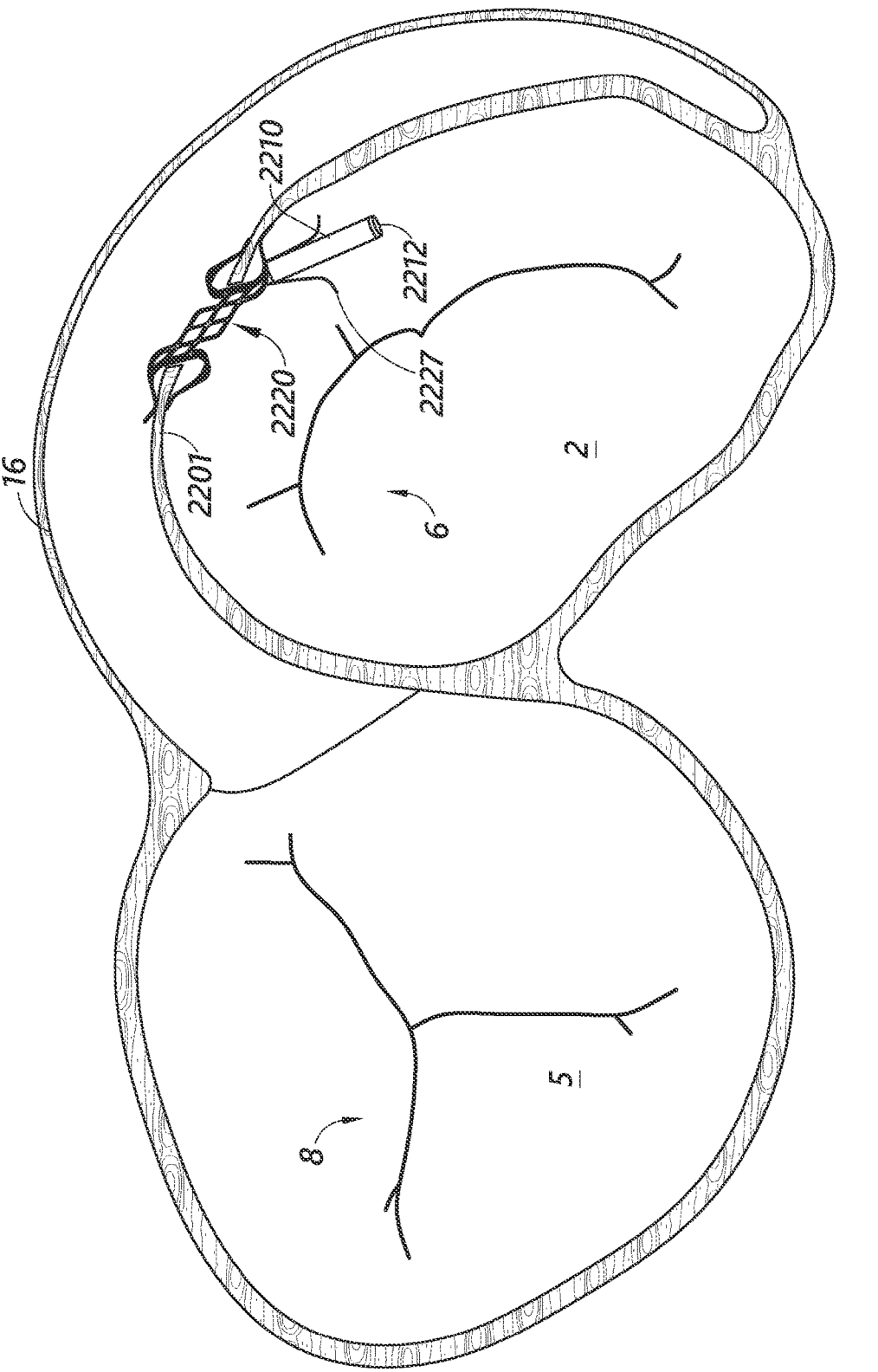

In some embodiments, a sensor device may be docked on a shunt structure or other implant device, such that the sensor device is secured in a desired location to provide sensor readings. For example, in a common procedure, a shunt structure may be implanted in cardiac tissue, after which a sensor may be docked on the shunting structure as part of the same procedure. FIGS. 22 and 23 illustrates a process for docking a sensor device 2210 on a shunt structure 2220 in accordance with one or more embodiments. As shown in FIG. 22, embodiments of the present disclosure may involve implanting a shunt structure 2220 in tissue 2201 of a heart, such as in a wall separating the left atrium 2 from the coronary sinus 16, as well as a sensor device 2210 comprising a transducer or sensor element 2212.

In some embodiments, the sensor 2210 may be attached to the distal end of a guidewire 2280 prior to implantation of the shunt structure 2220. For example, the guidewire 2220 may be placed initially within the atrium 2. Thereafter, the shunt structure 2220 may be implanted in the tissue wall 2201, after which withdrawal of the guidewire may cause the sensor 2210 to become engaged in the anchor features 2227, as shown in FIG. 23. The engagement between the sensor device 2210 and the anchor features 2227 may comprise a compression-fit or snap mechanism, or the like. By delivering the sensor device 2010 and the shunt structure 2220 at different times, the profile for delivery of such devices may be reduced. The sensor 2210 may be configured to attach to the anchor features 2227 via a coupling feature 2228 of any suitable or desirable size, shape, form, or configuration.

In some embodiments, the process may involve advancing the guidewire 2280 through an access 2203 in the tissue wall 2201 in connection with implantation of the shunt structure 2220. The guidewire 2280 may be advanced into the left atrium 2 past the anchor feature(s) 2227 associated with the shunt structure 2220. For example, as shown, the anchor features 2227 may be associated with (e.g., integrated with or attached to) an arm portion or other portion of the shunt structure 2220.

The guidewire 2280 may allow for simplified location of the access 2203, such that the delivery catheter may be relatively easily advanced along the guidewire into the atrium 2 or another target location. The process may further involve subsequently advancing the delivery catheter including a sensor device 2210 having at least one sensor element 2212 into the target chamber (e.g., left atrium). The sensor 2210 may advantageously be advanced past the anchor features 2227, wherein the sensor device 2210 may be anchored into the anchor features 2227 by pulling back on the sensor to clamp or fix the sensor device 2210 in engagement with the anchor features 2227, as shown in FIG. 23. In some embodiments, the sensor device 2210 is attached to or integrated with corresponding mating features for engaging with the anchor features 2227.

The procedure illustrated in FIGS. 22 and 23 may provide significant time savings by not requiring the guidewire 2280 to be withdrawn and/or replacing with a subsequent guidewire. Such time and resource savings may be particularly relevant with respect to access to the left atrium to the coronary sinus 16, as shown and described herein. The guidewire 2280 may attach mechanically to the sensor 2210. For example, a coupling feature 2228 associated with a sensor device 2210 may serve to attach the sensor device 2010 guidewire 2280.

Figure 25:
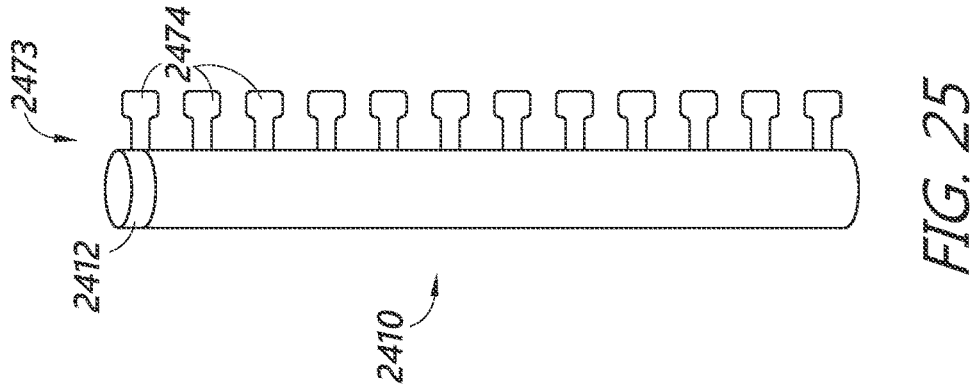
FIG. 25 illustrates a sensor device including an attachment rack feature including in accordance with one or more embodiments.
Figure 24:
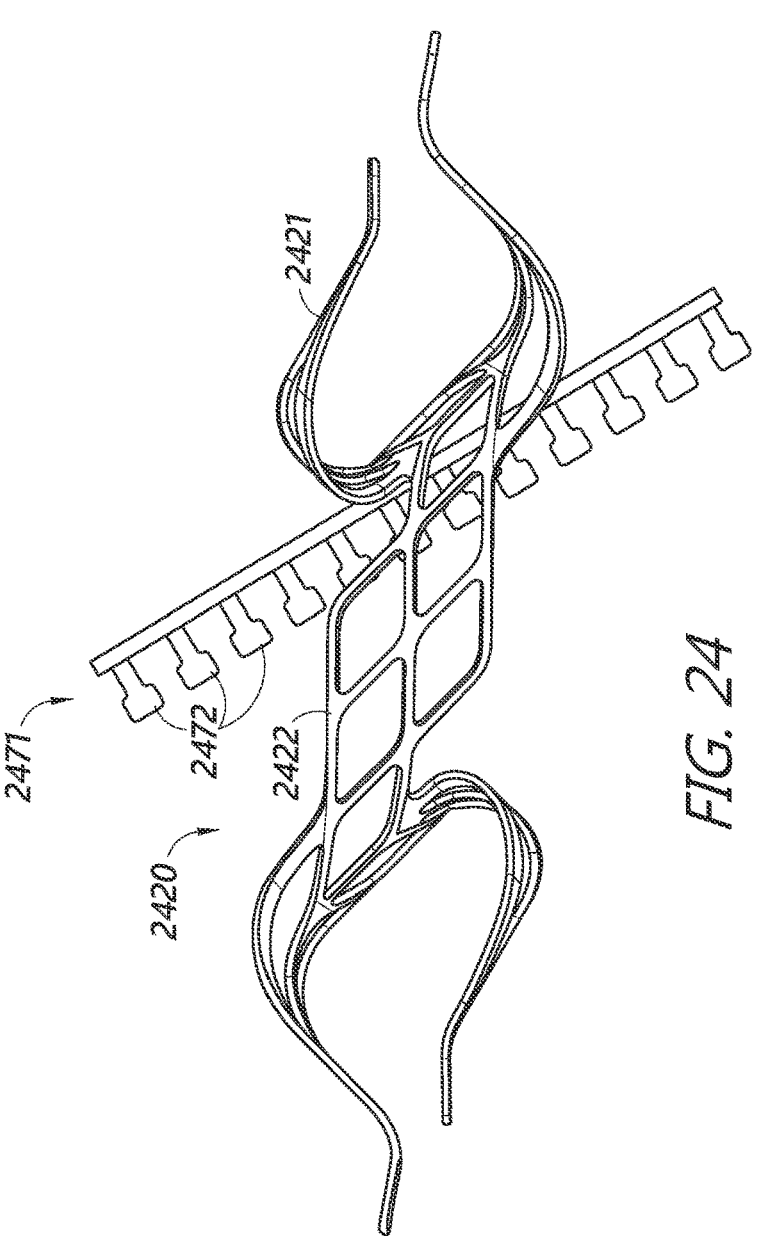
FIG. 24 illustrates a shunt structure having a sensor attachment rack feature in accordance with one or more embodiments.

Any type of attachment features for attaching a shunt structure to a sensor device may be used in accordance with embodiments of the present disclosure. FIG. 24 illustrates a shunt structure 2420 having a sensor attachment rack feature 2471. The attachment rack 2471 comprises a plurality of teeth, protrusions, gears, or other engagement features for mating with corresponding features associated with a sensor device. FIG. 25 shows a sensor device 2410 including an attachment rack feature 2473 including a plurality of teeth 2474, which may be configured and/or dimensioned to engage with the corresponding teeth 2472 of the shunt structure 2420.

Figure 26:
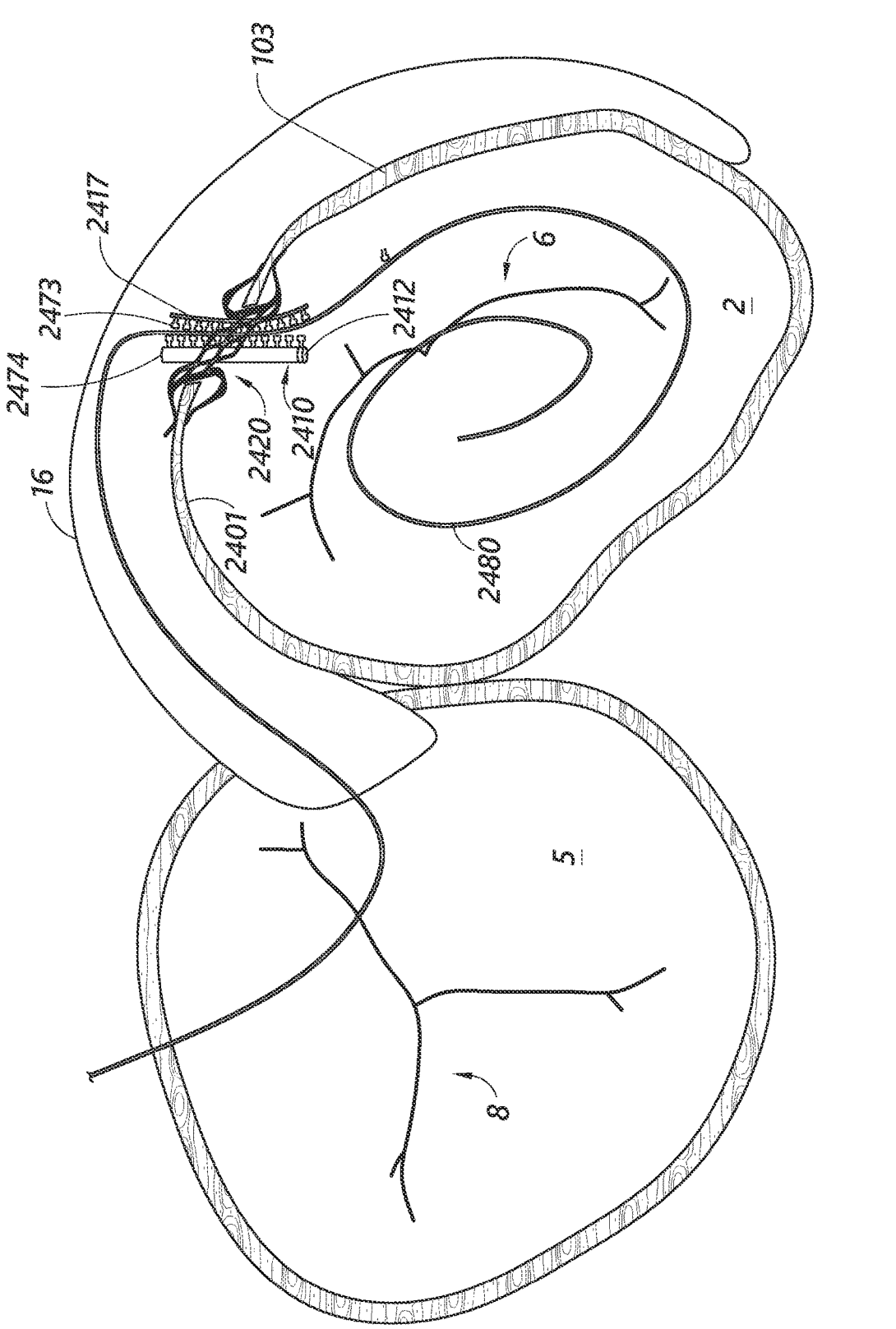
FIG. 26 illustrates a process for attaching the sensor device of FIG. 25 to the shunt structure of FIG. 24 in accordance with one or more embodiments.

FIG. 26 illustrates a process for attaching the sensor device 2410 of FIG. 25 to the shunt structure 2420 of FIG. 24 described above. For example, a guidewire 2480 may be advanced to the left atrium or other target chamber, vessel, or location. The guidewire 2480 may be used to implant the shunt structure 2420 in a tissue wall 2401 of the atrium, such as a wall separating the left atrium 2 from the coronary sinus 16. With the shunt structure positioned as shown in FIG. 26, the guidewire 2480 may be left in place, and may be used to hold open or otherwise interfere in some manner with the rack attachment feature 2472 of the shunt structure. The guidewire 2480 may further be used to deliver the sensor device 2410, including the engagement/attachment feature 2473 to the location where the shunt structure 2420 is implanted. The guidewire 2480 may subsequently be removed, allowing the mating teeth of the shunt structure 2420 and the sense device 2410 to engage or snap into locking engagement with one another to thereby secure the sensor device 2410 to the shunt structure 2420. Although use of the guidewire 2480 or interfere with the mating between the shunt structure 2420 and the sensor device 2410 is described, in some embodiments no such guidewire interference is implemented. For example, the sensor device 2410 may simply be advanced to the location of the shunt structure 2420 and pressure applied to engage the attachment features 2473 of the sensor device one 410 with the corresponding features 2471 of the shunt structure 2420.

Sensor Suspended in LA Using Radial Anchor(s)

Figure 27:
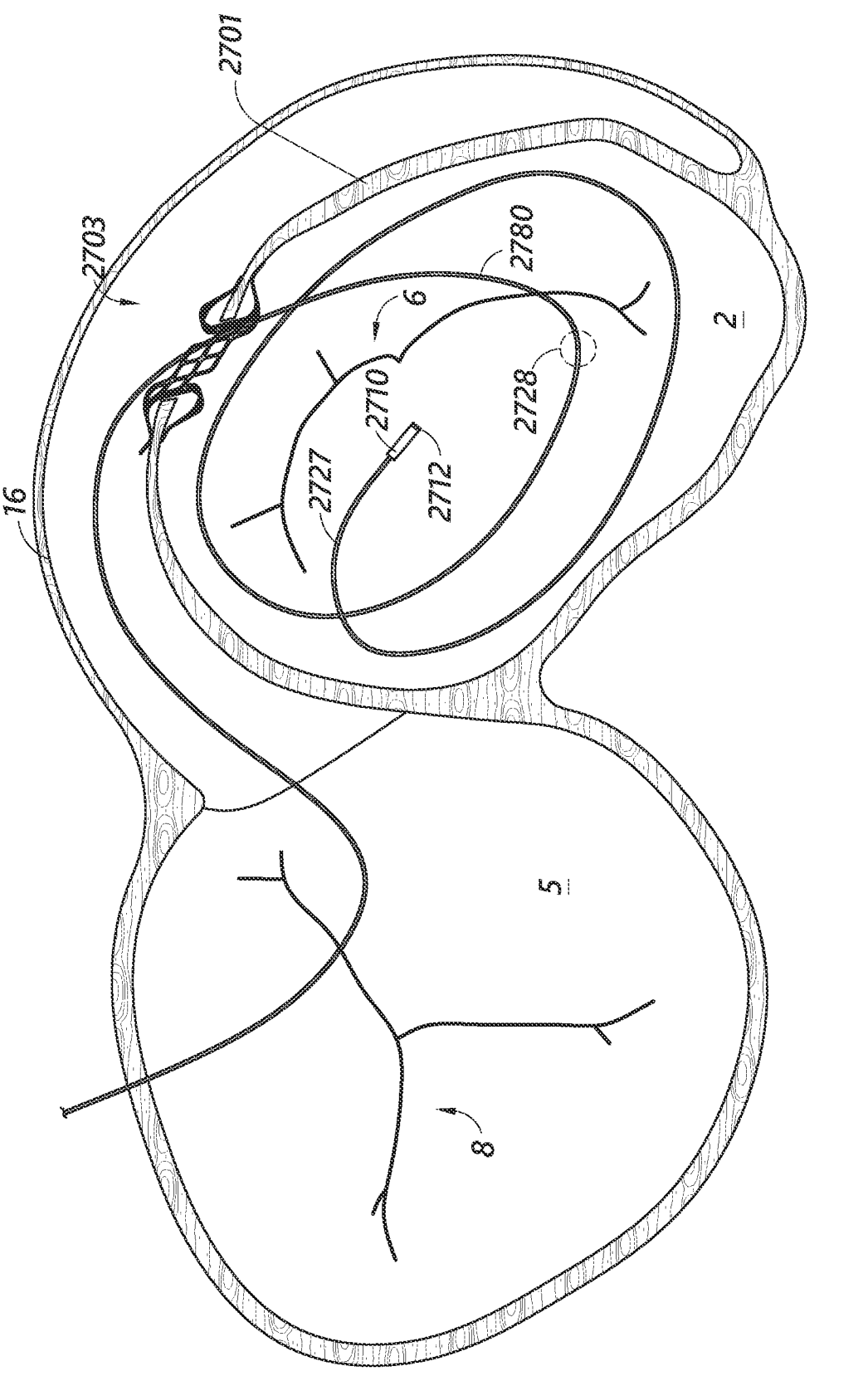
FIG. 27 illustrates a sensor device configured to be suspended in a heart chamber in accordance with one or more embodiments.

In some embodiments, a sensor device, such as a pressure sensor device, may be implanted in atrium or other chamber of the heart using one or more radially-expanding anchor features or coils. FIG. 27 illustrates a sensor device 2710 suspended in the left atrium 2 of the heart. Although certain embodiments are disclosed herein context of the left atrium, it should be understood that sensors in accordance with the present disclosure may be implanted in the right atrium or other chamber of the heart or body. The sensor 2710 is mounted or attached to a relatively large radially-expanding anchor system comprising a radially expanding wire 2727. The wire 2727 may be configured to contact at least a portion of the inner wall of the atrium 2 when expanded. In some embodiments, the wire 2727 is configured to exert outward radial force against the walls of the atrium to thereby suspend the sensor device 2710 in a central portion of the atrium. Furthermore, the wire 2727 may be at least partially flexible/elastic to allow for contracting and/or expanding in response to contraction and expansion of the atrium in connection with cardiac cycles. Although not illustrated in FIG. 27, in some embodiments, a shunt structure in accordance with embodiments the present disclosure may be implanted in the wall of the atrium 2, such as in the walls of the left atrium from the coronary sinus, in the same procedure used to dispose the sensor device 2710 in the atrium 2.

According to some implementations, the process for implanting the sensor device 2710 in the atrium 2 may involve accessing the atrium through the coronary sinus 16, as described in connection with other embodiments described herein. Access to the left atrium 2 may be made via a hole or opening in the wall 2701 separating the left atrium 2 from the coronary sinus 16. The sensor device 2710 and associated anchor wire 2727 may be delivered to the atrium to using a guidewire 2780, which may be attached to or integrated with the anchor wire 2727. In some embodiments, a detachable joint feature 2728 may allow for detachment of the anchor wire 2727 from the guidewire 2780 after deployment thereof.

Figure 28B:
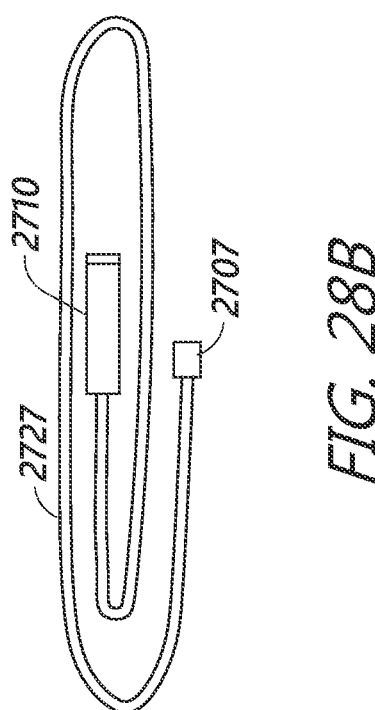
FIGS. 28A and 28B illustrate a top view of a sensor device in accordance with one or more embodiments.
Figure 28A:
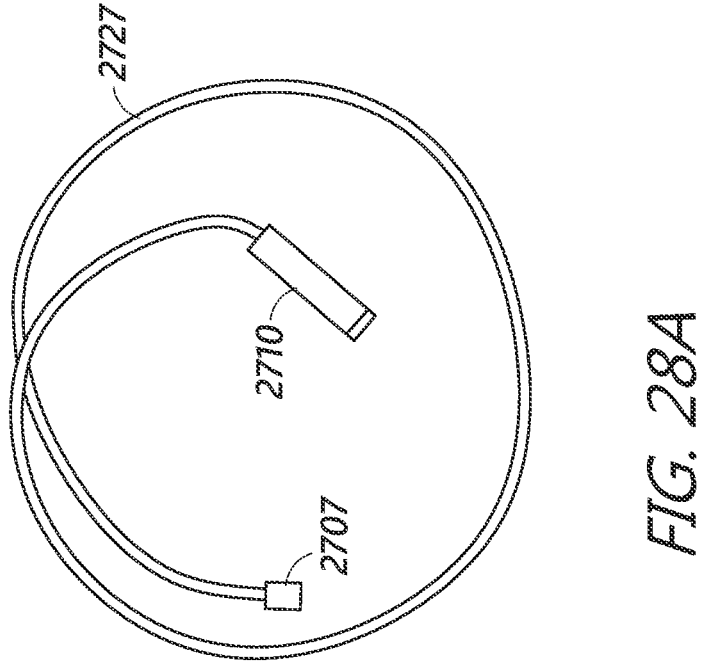

FIG. 28 illustrates an isolated top view of the sensor device 2710 and associated radially-expanding wire anchor 2727 after detachment from the guidewire 2780. In some embodiments, the anchor wire 2727 includes a proximal joint portion 2707, which may be configured to attach and/or detach from the guidewire 2780. FIG. 28B shows the sensor device 2710 and associated anchor wire 2727 in a collapsed state, which may correspond to a delivery state for advancement of the sensor device 2710 and anchor 2727 in a delivery catheter in connection with a transcatheter procedure.

The sensor device 2710 may be advanced to the atrium to over the guidewire. For example, after deploying the guidewire in connection with a shunt structure implantation procedure, before taking out the guidewire, the sensor device 2710 and/or anchor wire 2727 may be advanced to the atrium 2 and released, wherein spring tension of the anchor wire 2727 maintains the sensor device 2710 in a desired position, after which the guidewire 2780 may be detached from the anchor wire 2727 and withdrawn.

Figure 29:
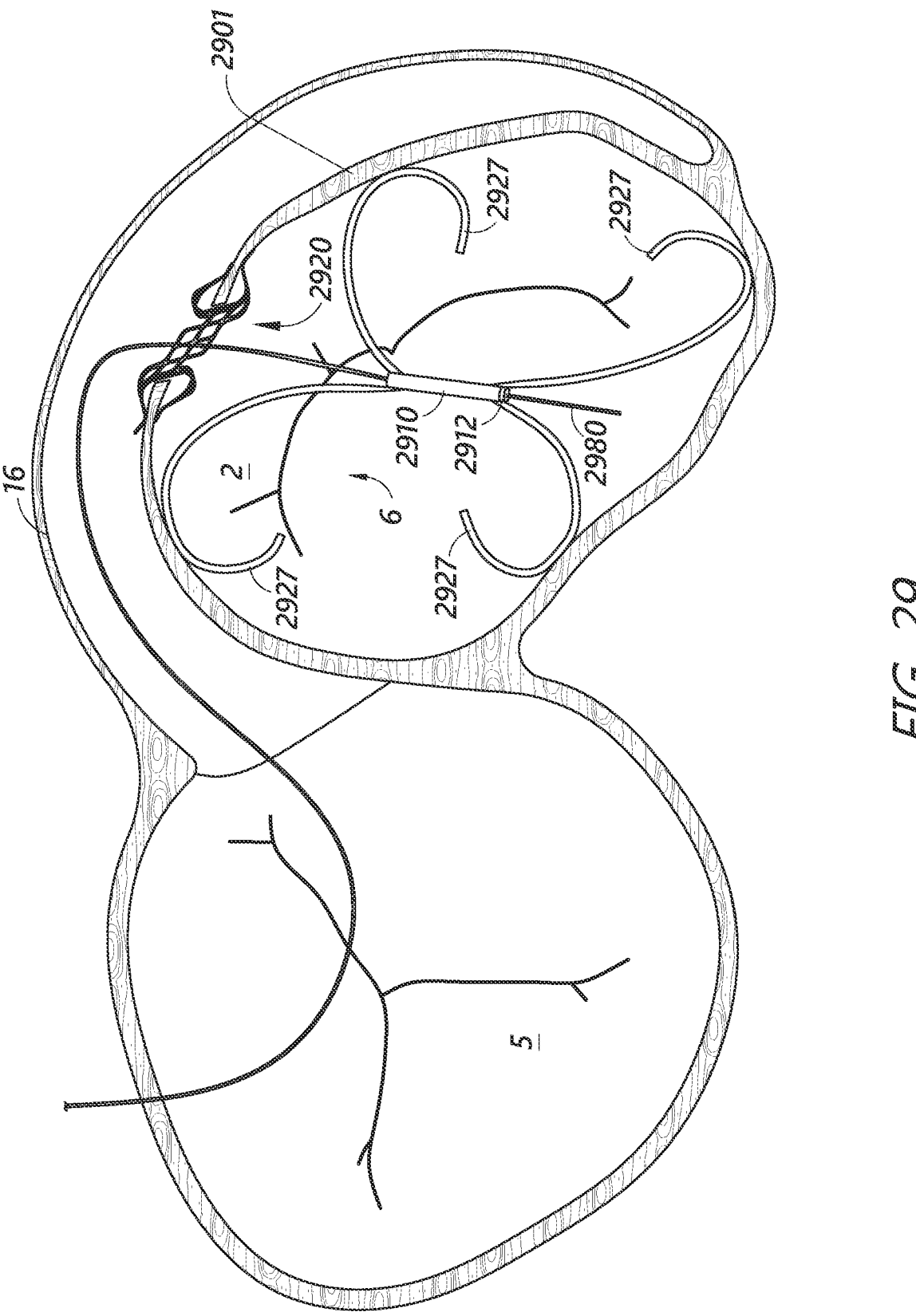
FIG. 29 illustrates a sensor device configured to be suspended in a heart chamber in accordance with one or more embodiments.

FIG. 29 illustrates an alternate embodiment in which a sensor device 2910 is suspended in the atrium or other chamber of the heart using a plurality of anchor arms 2927, as illustrated. The sensor device 2910 and associated anchor arms 2927 may be implanted in a similar manner as described above was respect to FIGS. 27 and 28, such as through the use of the guidewire 2980 in connection with implantation of a shunt structure 2920, as shown. Embodiments of FIGS. 27-29 may advantageously allow for implantation of a pressure sensor device in accordance with embodiments the present disclosure substantially without requiring anchoring of the pressure sensor device into biological tissue. For example, no barbs or other puncturing means may be necessary for embedding the wire anchor 2727 or anchor features 2927 in the atrial tissue.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including." "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X. Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third." etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A sensor implant device comprising:
    a shunt structure comprising a flow path conduit and a plurality of arms configured to secure the shunt structure to a tissue wall;
    a pressure sensor device comprising:
        one or more sensor elements;
        an antenna;
        control circuitry electrically coupled to the one or more sensor elements and the antenna; and
        a housing that houses the control circuitry; and
    a sensor attachment component integrally formed with one of the plurality of arms of the shunt structure, wherein the pressure sensor device is attached to the sensor attachment component.

2. The sensor implant device of claim 1, wherein the sensor attachment component is a support extension extending from the one of the plurality of arms, and the pressure sensor device is attached to the support extension.

3. The sensor implant device of claim 2, wherein the support extension has one or more retention features that wrap at least partially around the pressure sensor device.

4. The sensor implant device of claim 2, wherein the support extension and the housing of the pressure sensor device are a unitary form.

5. The sensor implant device of claim 1, wherein the housing has a cylindrical form with a proximal end portion and a distal end portion, and the one or more sensor elements comprises a first sensor element disposed at the proximal end and a second sensor element disposed at the distal end.

6. The sensor implant device of claim 1, wherein the housing has a cylindrical form, the antenna comprises a cylindrical ferrite core and a conductive wire coil wrapped around the ferrite core, and the antenna is housed within the housing.

7. The sensor implant device of claim 1, wherein the antenna is electrically coupled to the control circuitry via a tether.

8. The sensor implant device of claim 7, wherein the antenna is a flat spiral antenna.

9. The sensor implant device of claim 7, wherein the antenna is disposed at least partially within a hermetically-sealed flexible membrane.

10. The sensor implant device of claim 1, wherein the antenna is wrapped around the flow path conduit of the shunt structure.

11. The sensor implant device of claim 10, wherein the one or more sensor elements extends away from the antenna along a dimension parallel to a flow path axis through the flow path conduit.

12. The sensor implant device of claim 1, wherein the pressure sensor device projects away from a longitudinal axis of the shunt structure.

13. The sensor implant device of claim 1, wherein the shunt structure includes a plurality of interconnected struts forming cells therebetween.

14. The sensor implant device of claim 1, wherein the flow path conduit of the shunt structure is configured to be positioned in a tissue wall between a coronary sinus and a left atrium.

15. The sensor implant device of claim 14, wherein the pressure sensor device is configured to be positioned in the coronary sinus or the left atrium.

16. The sensor implant device of claim 14, wherein the housing and the one or more sensor elements of the pressure sensor device is positioned in the left atrium, and the antenna is tethered to the pressure sensor device and is positioned in the coronary sinus.

17. The sensor implant device of claim 1, wherein the support extension is a continuous extension from the one of the plurality of arms of the shunt structure.

18. The sensor implant device of claim 17, wherein the shunt structure and the support extension are made out of a memory metal.

19. The sensor implant device of claim 1, wherein the sensor attachment component has one or more retention features that at least partially encase the pressure sensor device.

20. A sensor implant device comprising:
    a shunt structure comprising a flow path conduit, a plurality of arms configured to secure the shunt structure to a tissue wall, and a support extension extending from and integrally formed with one of the plurality of arms; and
    a pressure sensor device attached to the support extension extending from the one of the plurality of arms of the shunt structure, the pressure sensor device comprising:
        one or more sensor elements;
        an antenna;
        control circuitry electrically coupled to the one or more sensor elements and the antenna; and
        a housing that houses the control circuitry.

21. A sensor implant device comprising:
    a shunt structure comprising a flow path conduit and a plurality of arms configured to secure the shunt structure to a tissue wall;
    a pressure sensor device attached to one of the plurality of arms of the shunt structure, the pressure sensor device comprising:
        one or more sensor elements;
        an antenna;
        control circuitry electrically coupled to the one or more sensor elements and the antenna; and
        a housing that houses the control circuitry; and
    a pouch attached to the one of the plurality of arms, the pressure sensor device slidingly disposed within the pouch.

22. The sensor implant device of claim 21, wherein a tension and/or compression of the pouch serves to retain the pressure sensor device in a fixed position within the pouch.

23. The sensor implant device of claim 21, wherein the pouch is a suture-based or cloth-based pouch.

\* \* \* \* \*